United States Patent
Zhang et al.

(10) Patent No.: US 12,426,502 B2
(45) Date of Patent: Sep. 23, 2025

(54) ELECTROLUMINESCENT MATERIALS AND DEVICES

(71) Applicant: BEIJING SUMMER SPROUT TECHNOLOGY CO., LTD., Beijing (CN)

(72) Inventors: Han Zhang, Beijing (CN); Le Wang, Beijing (CN); Junfei Wang, Beijing (CN); Qiang Wang, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 667 days.

(21) Appl. No.: 17/227,615

(22) Filed: Apr. 12, 2021

(65) Prior Publication Data
US 2021/0328153 A1    Oct. 21, 2021

(30) Foreign Application Priority Data
Apr. 13, 2020  (CN) .......................... 202010268985.1

(51) Int. Cl.
*C07D 487/04* (2006.01)
*C07D 487/16* (2006.01)
(Continued)

(52) U.S. Cl.
CPC ....... *H10K 85/6572* (2023.02); *C07D 487/04* (2013.01); *C09K 11/02* (2013.01);
(Continued)

(58) Field of Classification Search
CPC ............. H10K 85/657; H10K 85/6572; C07D 239/72; C07D 239/74; C07D 241/40; C07D 241/42
See application file for complete search history.

(56) References Cited

U.S. PATENT DOCUMENTS 5,703,436 A    12/1997 Forrest et al.
5,707,745 A    1/1998 Forrest et al.
(Continued)

FOREIGN PATENT DOCUMENTS

CN    108391433 A    8/2018
CN    111269239 A    6/2020
(Continued)

OTHER PUBLICATIONS

KR-2015077220-A (Year: 2015).*
(Continued)

*Primary Examiner* — Jennifer A Boyd
*Assistant Examiner* — Rachel Simbana
(74) *Attorney, Agent, or Firm* — Workman Nydegger

(57) ABSTRACT

Provided are an electroluminescent material and device. The electroluminescent material is a compound having an indole- and pyrrole-fused azamacrocycle structure segment which is connected to quinazoline having a substitution on a specific ring, quinoxaline having a substitution on a specific ring, or a similar structure thereof, and can be used as the host material in the electroluminescent device. These novel compounds can obtain a lower driving voltage, effectively improve device efficiency, greatly prolong device lifetime, and provide better device performance. Further provided are an electroluminescent device and a compound formulation.

24 Claims, 1 Drawing Sheet

(51) Int. Cl.
    *C07F 15/00*     (2006.01)
    *C09K 11/02*     (2006.01)
    *C09K 11/06*     (2006.01)
    *H10K 50/11*     (2023.01)
    *H10K 85/30*     (2023.01)
    *H10K 85/60*     (2023.01)
    *H10K 101/10*     (2023.01)

(52) U.S. Cl.
    CPC ............ *C09K 11/06* (2013.01); *H10K 85/342* (2023.02); *C09K 2211/1007* (2013.01); *C09K 2211/1029* (2013.01); *C09K 2211/185* (2013.01); *H10K 50/11* (2023.02); *H10K 2101/10* (2023.02)

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,416 | B2 | 6/2011 | Bottner et al. |
| 2002/0076576 | A1* | 6/2002 | Li ................... H10K 85/00 428/917 |
| 2003/0230980 | A1 | 12/2003 | Forrest et al. |
| 2004/0174116 | A1 | 9/2004 | Lu et al. |
| 2015/0349273 | A1 | 12/2015 | Hung et al. |
| 2016/0359122 | A1 | 12/2016 | Boudreault et al. |
| 2018/0102486 | A1* | 4/2018 | Lee ................ H10K 85/657 |
| 2018/0337340 | A1* | 11/2018 | Moon ............... C07D 487/16 |
| 2021/0167297 | A1 | 6/2021 | Wang et al. |
| 2022/0077404 | A1 | 3/2022 | Zhang et al. |
| 2022/0177502 | A1 | 6/2022 | Wang et al. |
| 2022/0231232 | A1 | 7/2022 | Wang et al. |
| 2022/0274998 | A1 | 9/2022 | Wang et al. |
| 2022/0289681 | A1 | 9/2022 | Wang et al. |

FOREIGN PATENT DOCUMENTS

| | | | |
|---|---|---|---|
| CN | 113527316 | | 10/2021 |
| CN | 113527317 | | 10/2021 |
| CN | 113968873 | | 1/2022 |
| CN | 113968875 | | 1/2022 |
| CN | 114075208 | | 2/2022 |
| CN | 114256430 | | 3/2022 |
| CN | 114835718 | | 8/2022 |
| KR | 2015077220 | A * | 7/2015 |
| KR | 20150077220 | A | 7/2015 |
| KR | 20170066241 | A | 6/2017 |

OTHER PUBLICATIONS

Tang et al., "Organic electroluminescent diodes" Applied Physics Letters, vol. 51 (Sep. 1987) pp. 913-915.
Joyama et al., "Highly efficient organic light-emitting diodes from delayed fluorescence" Nature, vol. 492 (Dec. 13, 2012) pp. 234-238.
Chinese Office Action dated Aug. 25, 2023, issued in Chinese Application No. 202010268985.1 (English Translation provided).
Chinese Search Report dated Apr. 13, 2020, issued in Chinese Application No. 2020102689851(English Translation provided).
Korean Notice of Grant dated Jul. 31, 2023, issued in Korean Application No. 10-2021-0047001, filed Apr. 12, 2021 (English Translation provided).
Korean Office Action dated Dec. 26, 2022, issued in Korean Application No. 10-2021-0047001, filed Apr. 12, 2021 (English Translation provided).

* cited by examiner

ELECTROLUMINESCENT MATERIALS AND DEVICES

CROSS-REFERENCE TO RELATED APPLICATION(S)

This application claims the benefit of and priority to Chinese Patent Application No. CN 202010268985.1, filed Apr. 13, 2020, which is incorporated herein by reference in its entirety.

TECHNICAL FIELD

The present disclosure relates to compounds for organic electronic devices such as organic light-emitting devices. More particularly, the present disclosure relates to a novel compound that has a parent core structure formed of an indole- and pyrrole-fused azamacrocycle that is connected to quinazoline having a substitution on a specific ring, quinoxaline having a substitution on a specific ring, or a similar structure thereof. The present disclosure further relates to an organic electroluminescent device as well as a compound formulation including the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

For the development of phosphorescent OLEDs, the selection of suitable host materials to work with phosphorescent light-emitting materials is an important and extensive research direction.

US20180337340A1 discloses a compound having a structure represented by a formula

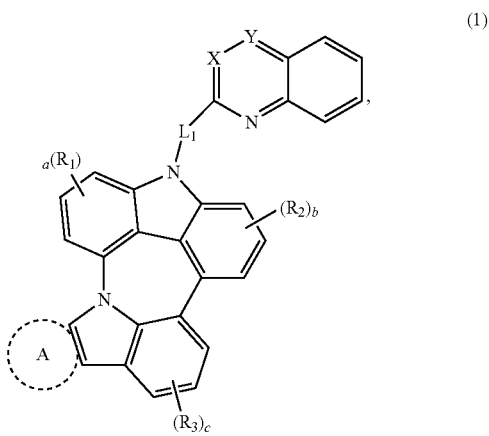

(1)

wherein X and Y, each independently, represent $CR_4$ or N, and the examples of the compound include

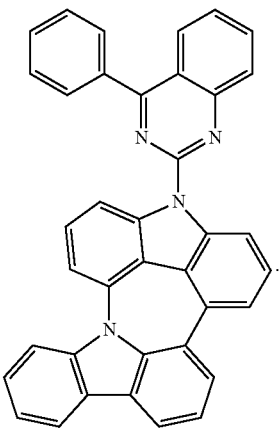

(C-1)

Obviously, the inventors of this application noted the advantages of the compound obtained by joining the fused ring structure of the aza 7-membered ring to a quinazoline structural unit as a phosphorescent host material, but they did not disclose or teach the application of continuing to introduce substituents on the phenylquinazoline structural unit.

At present, many host materials of different structures have been developed, but the related device performance, such as device efficiency, driving voltage, lifetime, etc., is still unsatisfactory, and further research and development is still urgently needed.

SUMMARY

The present disclosure aims to provide a series of compounds having an indole- and pyrrole-fused azamacrocycle structure segment which is connected to quinazoline having a substitution on a specific ring, quinoxaline having a substitution on a specific ring, or a similar structure thereof, to solve at least part of the above-mentioned problems. These compounds may be used as host materials in organic electroluminescent devices. These novel compounds can obtain a lower driving voltage, effectively improve the device efficiency, greatly prolong the device lifetime, and provide better device performance.

According to an embodiment of the present disclosure, disclosed is a compound having a structure of H-L-E, wherein H has a structure represented by Formula 1:

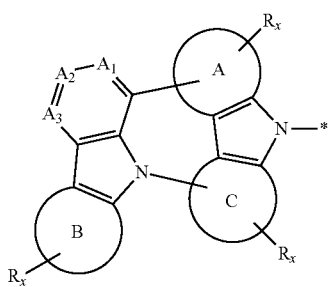

Formula 1 wherein in Formula 1, $A_1$, $A_2$, and $A_3$ are, at each occurrence identically or differently, selected from N or CR, and ring A, ring B, and ring C are, at each occurrence identically or differently, selected from a carbon ring having 5 to 18 carbon atoms or a heterocyclic ring having 3 to 18 carbon atoms;

$R_x$ represents, at each occurrence identically or differently, mono-substitution, multiple substitutions or non-substitution;

wherein E has a structure represented by Formula 2:

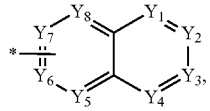

Formula 2 wherein $Y_1$ to $Y_4$ are, at each occurrence identically or differently, selected from N, $CR_y$ or $CR_z$, any two of $Y_5$ to $Y_8$ are selected from N, the other two of $Y_5$ to $Y_8$ are respectively selected from C or $CR_y$, and at least one of $Y_1$ to $Y_4$ is selected from $CR_z$;

L is selected from a single bond, substituted or unsubstituted arylene having 6 to 30 carbon atoms, substituted or unsubstituted heteroarylene having 3 to 30 carbon atoms, and combinations thereof, wherein R, $R_x$, and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

wherein $R_z$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof, wherein adjacent substituents R, $R_x$ can be optionally joined to form a ring;

wherein adjacent substituents $R_y$ can be optionally joined to form a ring.

According to another embodiment of the present disclosure, further disclosed is an electroluminescent device, comprising an anode, a cathode, and an organic layer disposed between the anode and the cathode, wherein the organic layer includes the compound having a structure of H-L-E described in the above embodiment.

According to another embodiment of the present disclosure, further disclosed is a compound formulation, comprising the compound having a structure of H-L-E described in the above embodiment.

The novel compounds disclosed by the present disclosure have an indole- and pyrrole-fused azamacrocycle structure segment which is connected to quinazoline having a substitution on a specific ring, quinoxaline having a substitution on a specific ring or a similar structure thereof, and can be used as the host material in the electroluminescent device. These novel compounds can obtain a lower driving voltage, effectively improve device efficiency, greatly prolong device lifetime, and provide better device performance.

DETAILED DESCRIPTION

Figure 1:
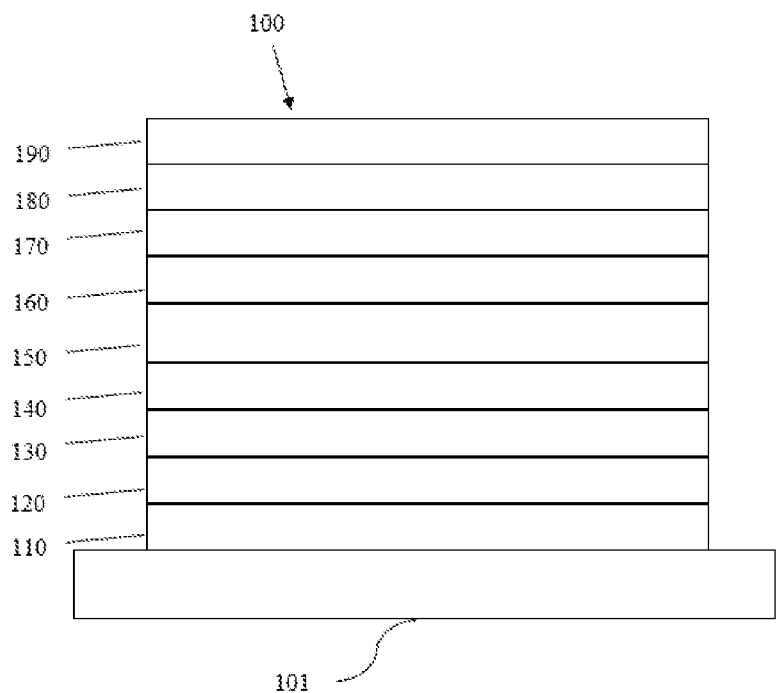
FIG. 1 is a schematic diagram of an organic light-emitting apparatus that may include a compound and a compound formulation disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
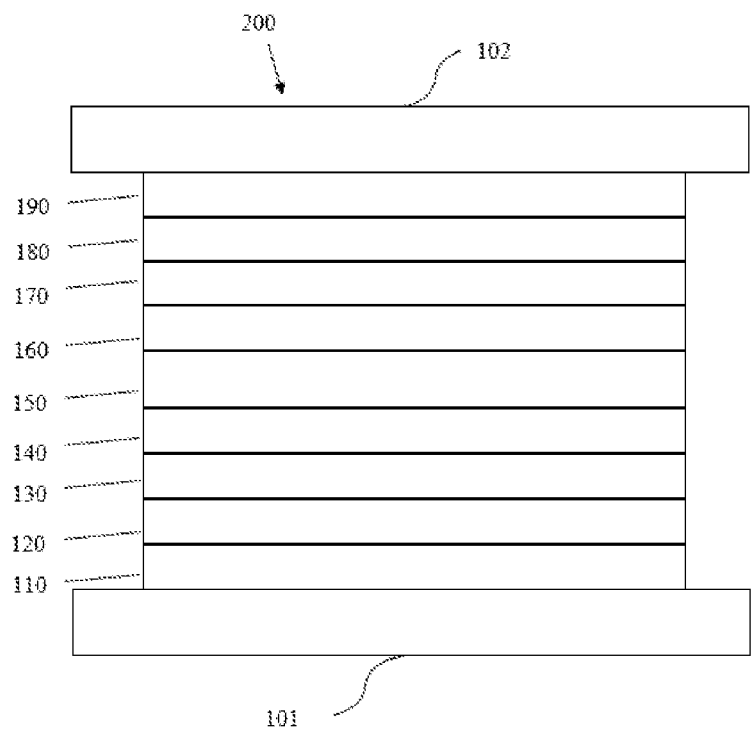
FIG. 2 is a schematic diagram of another organic light-emitting apparatus that may include a compound and a compound formulation disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing 2 to 15 carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyll-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing 2 to 15 carbon atoms. Additionally, the alkynyl group may be optionally substituted.

Aryl or aromatic group—as used herein includes noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein includes aromatic and non-aromatic cyclic groups. Heteroaromatic also means heteroaryl. Preferred non-aromatic heterocyclic groups are those containing 3 to 7 ring atoms which include at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein includes noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted arylalkyl, substituted alkoxy, substituted aryloxy, substituted alkenyl, substituted aryl, substituted heteroaryl, substituted alkylsilyl, substituted arylsilyl, substituted amine, substituted acyl, substituted carbonyl, substituted carboxylic acid group, substituted ester group, substituted sulfinyl, substituted sulfonyl and substituted phosphino is used, it means that any group of alkyl, cycloalkyl, heteroalkyl, arylalkyl, alkoxy, aryloxy, alkenyl, aryl, heteroaryl, alkylsilyl, arylsilyl, amine, acyl, carbonyl, carboxylic acid group, ester group, sulfinyl, sulfonyl and phosphino may be substituted with one or more groups selected from the group consisting of deuterium, a halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted arylalkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a cyano group, an isocyano group, a sulfanyl group, a sulfinyl group, a sulfonyl group and a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in the present disclosure, the hydrogen atoms can be partially or fully replaced by deuterium. Other atoms such as carbon and nitrogen can also be replaced by their other stable isotopes. The replacement by other stable isotopes in the compounds may be preferred due to its enhancements of device efficiency and stability.

In the compounds mentioned in the present disclosure, multiple substitutions refer to a range that includes a double substitution, up to the maximum available substitutions. When a substitution in the compounds mentioned in the present disclosure represents multiple substitutions (including di, tri, tetra substitutions etc.), that means the substituent may exist at a plurality of available substitution positions on its linking structure, the substituents present at a plurality of available substitution positions may be the same structure or different structures.

In the compounds mentioned in the present disclosure, adjacent substituents in the compounds cannot connect to form a ring unless otherwise explicitly defined, for example, adjacent substituents can be optionally joined to form a ring. In the compounds mentioned in the present disclosure, adjacent substituents can be optionally joined to form a ring, including both the case where adjacent substituents can be joined to form a ring, and the case where adjacent substituents are not joined to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

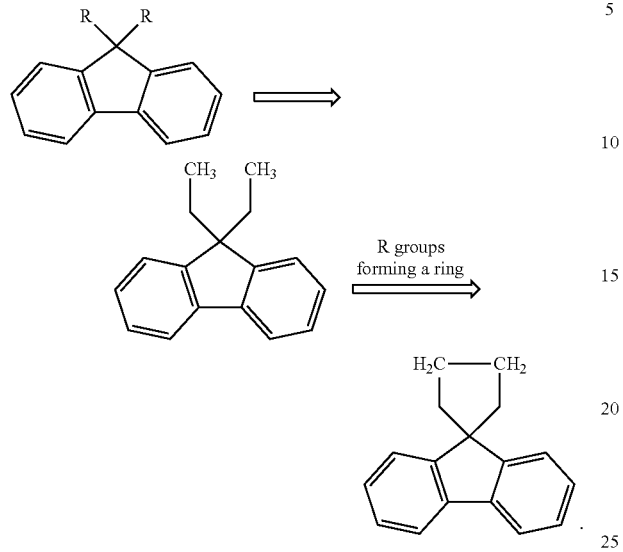

The expression that adjacent substituents can be optionally joined to form a ring is also intended to mean that two substituents bonded to carbon atoms which are directly bonded to each other are joined to each other via a chemical bond to form a ring, which can be exemplified by the following formula.

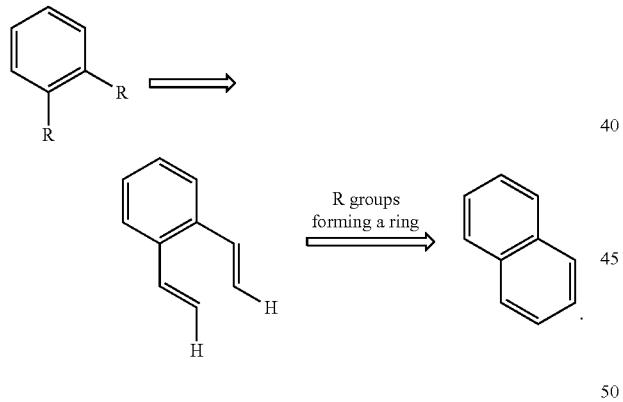

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

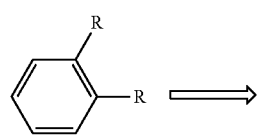

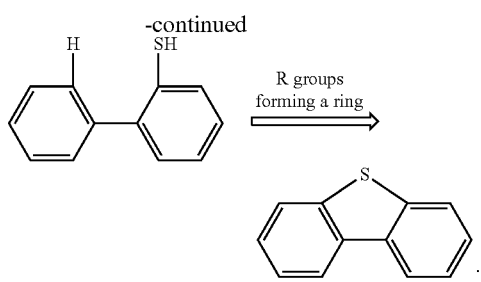

According to an embodiment of the present disclosure, disclosed is a compound having a structure of H-L-E, wherein H has a structure represented by Formula 1:

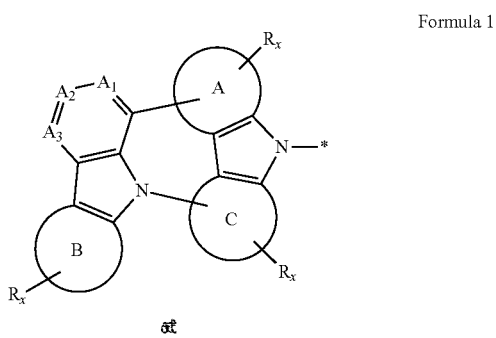

Formula 1 wherein in Formula 1, $A_1$, $A_2$, and $A_3$ are, at each occurrence identically or differently, selected from N or CR, and ring A, ring B, and ring C are, at each occurrence identically or differently, selected from a carbon ring having 5 to 18 carbon atoms or a heterocyclic ring having 3 to 18 carbon atoms;
$R_x$ represents, at each occurrence identically or differently, mono-substitution, multiple substitutions or non-substitution;
wherein E has a structure represented by Formula 2:

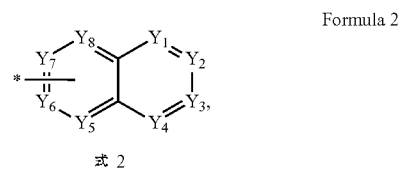

Formula 2 wherein $Y_1$ to $Y_4$ are, at each occurrence identically or differently, selected from N, $CR_y$ or $CR_z$, any two of $Y_5$ to $Y_8$ are selected from N, the other two of $Y_5$ to $Y_8$ are respectively selected from C or $CR_y$, and at least one of $Y_1$ to $Y_4$ is selected from $CR_z$;
L is selected from a single bond, substituted or unsubstituted arylene having 6 to 30 carbon atoms, substituted or unsubstituted heteroarylene having 3 to 30 carbon atoms, and combinations thereof;
wherein R, $R_x$, and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

wherein $R_z$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

wherein adjacent substituents R, $R_x$ can be optionally joined to form a ring;

wherein adjacent substituents $R_y$ can be optionally joined to form a ring.

In this embodiment, "*" in Formula 1 represents a position where the structure represented by Formula 1 is connected to the L, and the "*" in Formula 2 represents a position where the structure represented by Formula 2 is connected to the L.

In this embodiment, the expression that adjacent substituents R, $R_x$ can be optionally joined to form a ring is intended to mean that adjacent substituents R can be optionally joined to form a ring; also intended to mean that when a plurality of $R_x$ are present on the ring A, adjacent substituents $R_x$ can be optionally joined to form a ring; also intended to mean that when a plurality of $R_x$ are present on the ring B, adjacent substituents $R_x$ can be optionally joined to form a ring; also intended to mean that when a plurality of $R_x$ are present on the ring C, adjacent substituents $R_x$ can be optionally joined to form a ring; and also intended to mean that adjacent substituents R and $R_x$ can be optionally joined to form a ring. It is obvious that for those skilled in the art, adjacent substituents R, $R_x$ may not be joined to form a ring. In this case, adjacent substituents R are not joined to form a ring, and/or adjacent substituents $R_x$ are not joined to form a ring, and/or adjacent substituents R and $R_x$ are also not joined to form a ring.

In the present disclosure, the expression that adjacent substituents $R_y$ can be optionally joined to form a ring is intended to mean that any two adjacent $R_y$ can be joined to form a ring. Obviously, adjacent $R_y$ may not be joined to form a ring.

According to an embodiment of the present disclosure, wherein in Formula 1, the ring A, ring B, and ring C are, at each occurrence identically or differently, selected from a five-membered carbon ring, an aromatic ring having 6 to 18 carbon atoms or a heteroaromatic ring having 3 to 18 carbon atoms.

According to an embodiment of the present disclosure, wherein in Formula 1, the ring A, ring B, and ring C are, at each occurrence identically or differently, selected from a five-membered carbon ring, a benzene ring, a five-membered heteroaromatic ring or a six-membered heteroaromatic ring.

According to an embodiment of the present disclosure, wherein H has a structure represented by Formula 1-a:

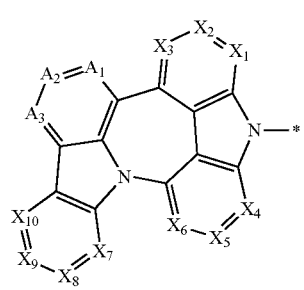

Formula 1-a wherein $A_1$ to $A_3$ are, at each occurrence identically or differently, selected from N or CR, and $X_1$ to $X_{10}$ are, at each occurrence identically or differently, selected from N or $CR_x$;

wherein R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

wherein adjacent substituents R, $R_x$ can be optionally joined to form a ring.

In this embodiment, the expression that adjacent substituents R, $R_x$ can be optionally joined to form a ring is intended to mean that adjacent substituents R can be optionally joined to form a ring; also intended to mean that adjacent substituents $R_x$ in $X_1$ to $X_3$ can be optionally joined to form a ring; also intended to mean that adjacent substituents $R_x$ in $X_4$ to $X_6$ can be optionally joined to form a ring; also intended to mean that adjacent substituents $R_x$ in $X_7$ to $X_{10}$ can be optionally joined to form a ring; and also intended to mean that adjacent substituents $R_x$ or adjacent substituents R and $R_x$ can be optionally joined to form a ring, for example, adjacent substituents in $A_1$ and $X_3$, and/or $A_3$ and $X_{10}$, and/or $X_6$ and $X_7$ can be optionally joined to form a ring. It is obvious that for those skilled in the art, adjacent substituents R, $R_x$ may not be joined to form a ring. In this case, adjacent substituents R are not joined to form a ring, and/or adjacent substituents $R_x$ are not joined to form a ring, and/or adjacent substituents R and $R_x$ are also not joined to form a ring.

According to an embodiment of the present disclosure, wherein R and $R_x$ are, at each occurrence identically or differently, selected from the group consisting of hydrogen, deuterium, halogen, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a sulfanyl group, and combinations thereof;

wherein adjacent substituents R, $R_x$ can be optionally joined to form a ring.

In this embodiment, the expression that adjacent substituents R, $R_x$ can be optionally joined to form a ring is intended to mean that adjacent substituents R can be optionally joined to form a ring; also intended to mean that adjacent substituents $R_x$ in $X_1$ to $X_3$ can be optionally joined to form a ring; also intended to mean that adjacent substituents $R_x$ in $X_4$ to $X_6$ can be optionally joined to form a ring; also intended to mean that adjacent substituents $R_x$ in $X_7$ to $X_{10}$ can be optionally joined to form a ring; and also intended to mean that adjacent substituents $R_x$ or adjacent substituents R and $R_x$ can be optionally joined to form a ring, for example, adjacent substituents in $A_1$ and $X_3$, and/or $A_3$ and $X_{10}$, and/or $X_6$ and $X_7$ can be optionally joined to form a ring. It is obvious that for those skilled in the art, adjacent substituents R, $R_x$ may not be joined to form a ring. In this case, adjacent substituents R are not joined to form a ring, and/or adjacent substituents $R_x$ are not joined to form a ring, and/or adjacent substituents R and $R_x$ are also not joined to form a ring.

According to an embodiment of the present disclosure, wherein in Formula 1-a, at least one of R and $R_x$ is selected from deuterium, substituted or unsubstituted aryl having 6 to 30 carbon atoms, or substituted or unsubstituted heteroaryl having 3 to 30 carbon atoms.

According to an embodiment of the present disclosure, wherein in Formula 1-a, at least one of R and $R_x$ is selected from deuterium, phenyl, biphenyl, or pyridyl.

According to an embodiment of the present disclosure, wherein in Formula 1-a, for adjacent substituents R in $A_1$ to $A_3$, adjacent substituents $R_x$ in $X_1$ to $X_3$, adjacent substituents $R_x$ in $X_4$ to $X_6$, and adjacent substituents $R_x$ in $X_7$ to $X_{10}$, at least one group of these groups of adjacent substituents is joined to form a ring.

In this embodiment, the expression that at least one group of these groups of adjacent substituents is joined to form a ring is intended to mean that for groups of adjacent substituents present in Formula 1-a, for example, two adjacent substituents R in $A_1$ and $A_2$, two adjacent substituents R in $A_2$ and $A_3$, two adjacent substituents $R_x$ in $X_1$ and $X_2$, two adjacent substituents $R_x$ in $X_2$ and $X_3$, two adjacent substituents $R_x$ in $X_4$ and $X_5$, two adjacent substituents $R_x$ in $X_5$ and $X_6$, two adjacent substituents $R_x$ in $X_7$ and $X_8$, two adjacent substituents $R_x$ in $X_8$ and $X_9$, and two adjacent substituents $R_x$ in $X_9$ and $X_{10}$, at least one group of these groups of substituents is joined to form a ring.

According to an embodiment of the present disclosure, wherein H is selected from the group consisting of the following structures:

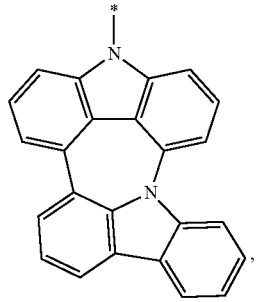

H-1

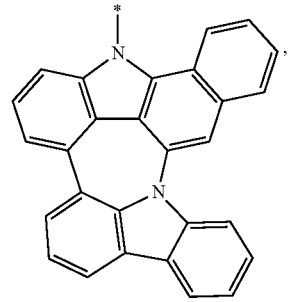

H-2

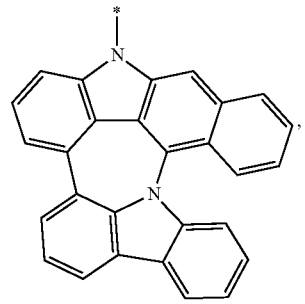

H-3

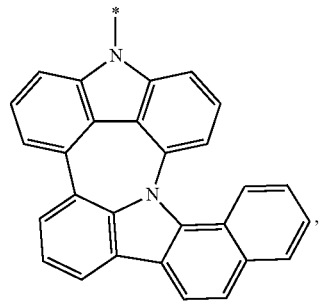

H-4

-continued
H-5
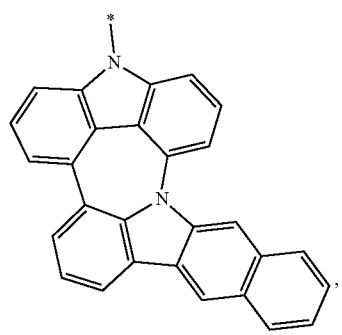
H-6
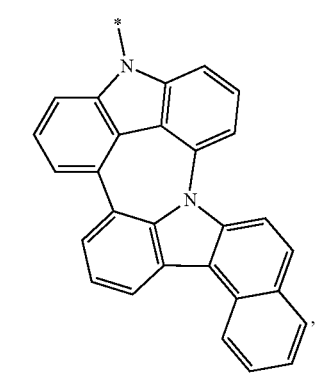
H-7
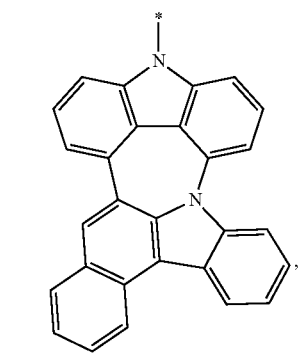
H-8
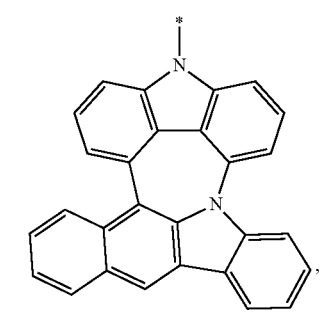
-continued
H-9
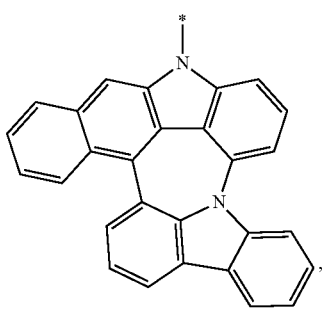
H-10
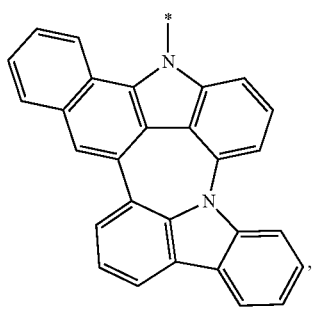
H-11
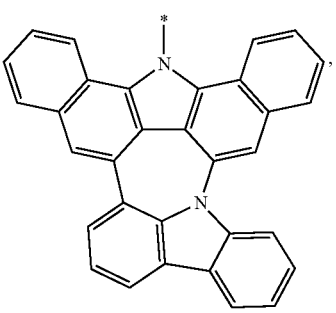
H-12
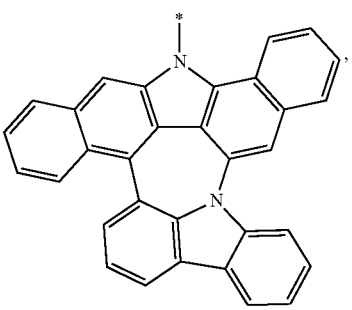
H-13
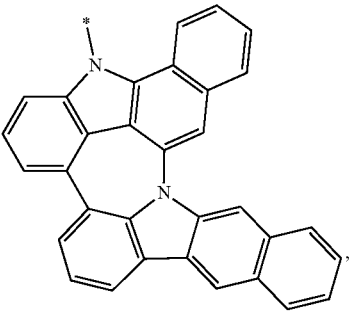

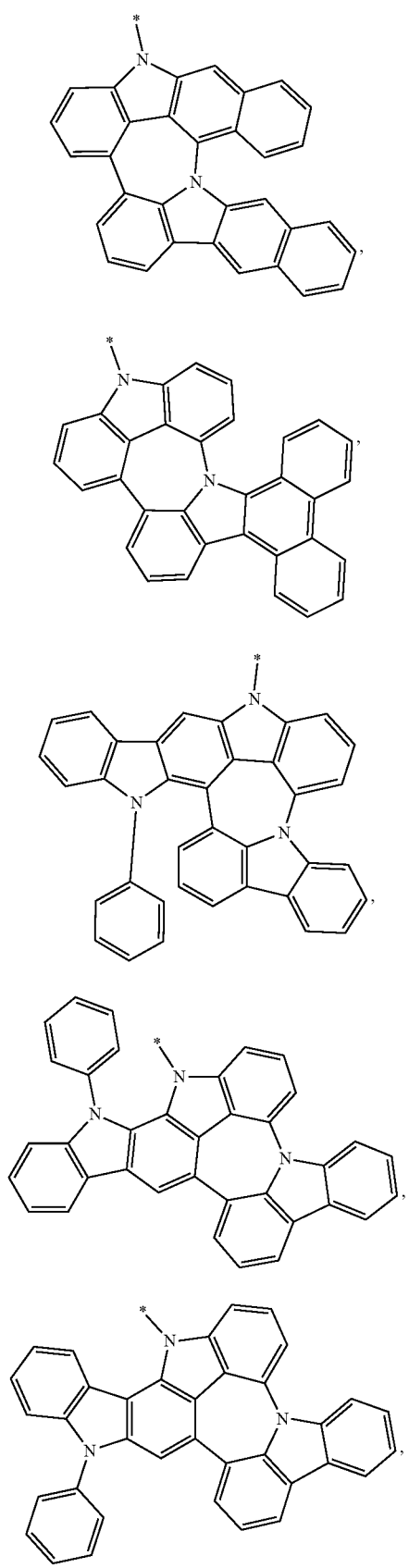
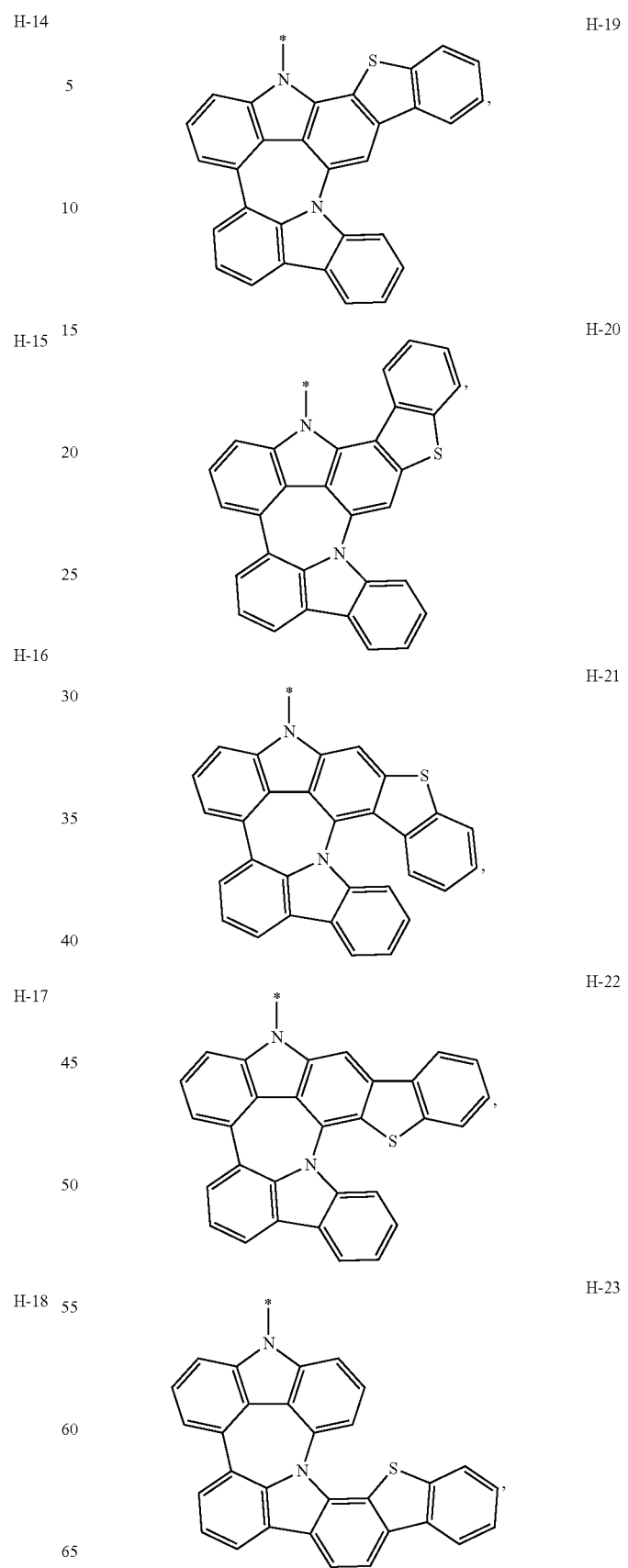

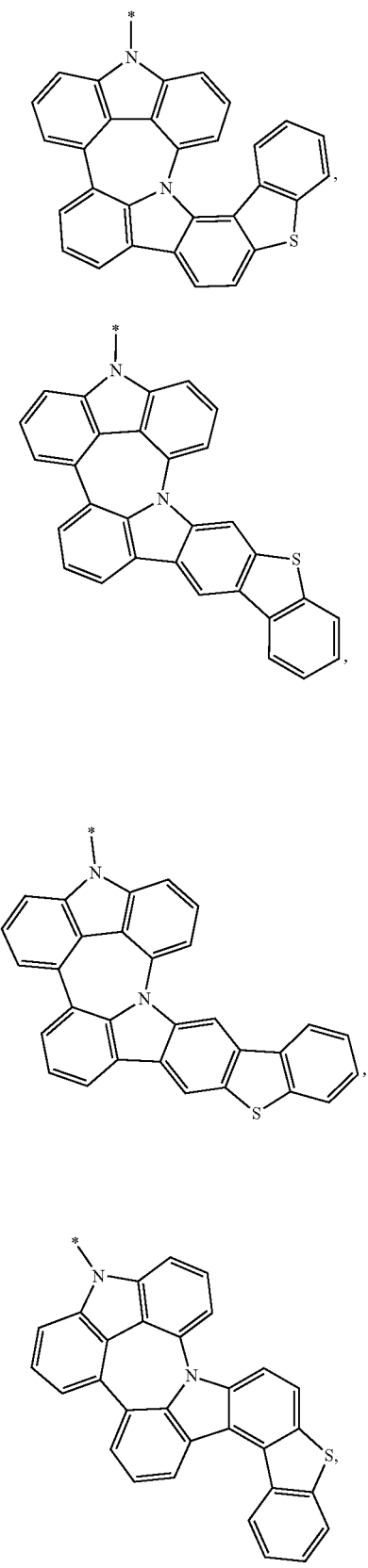
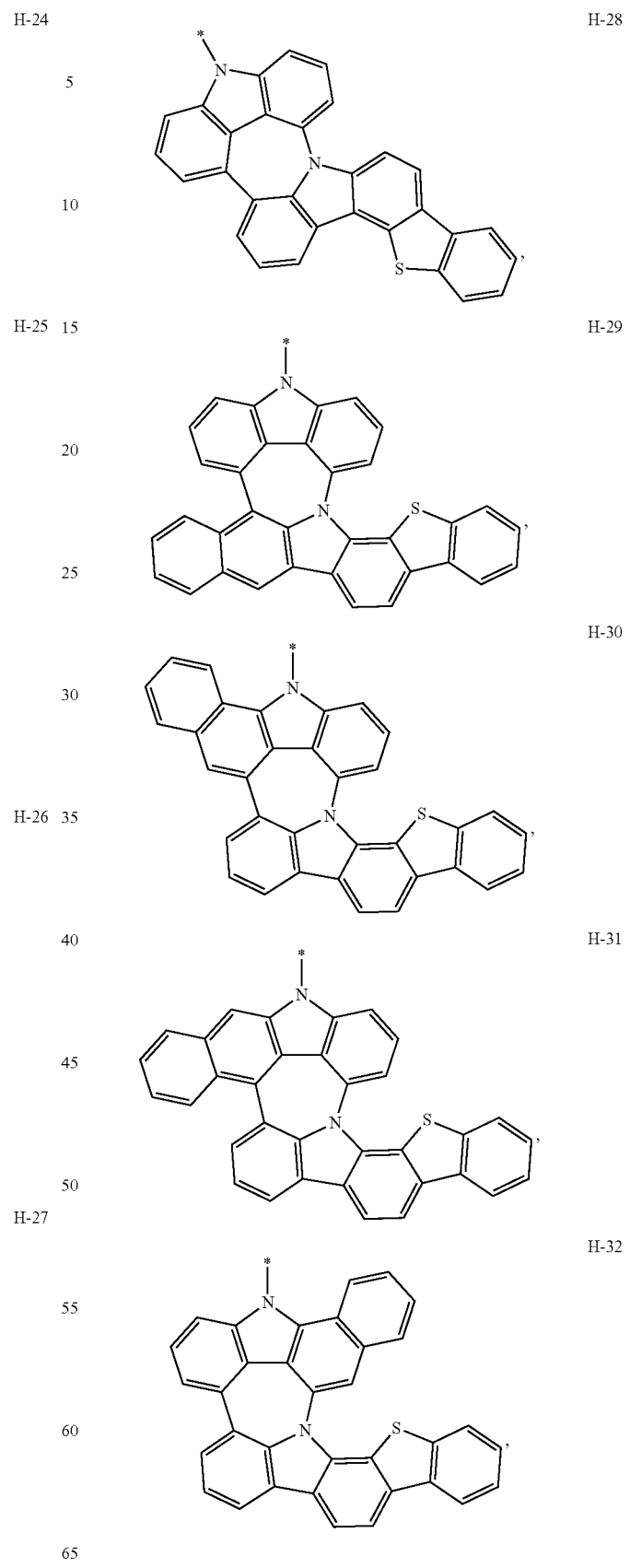

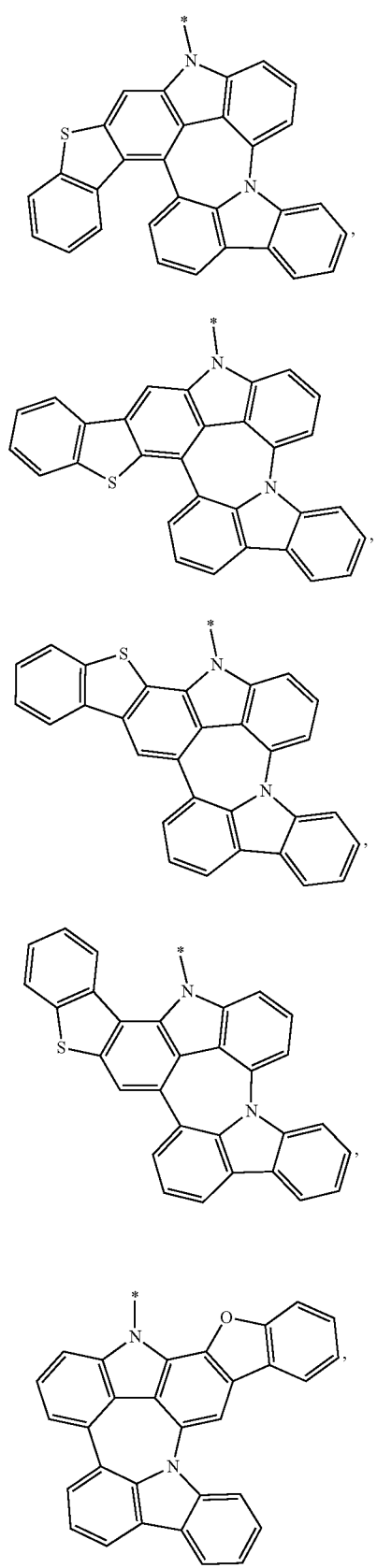
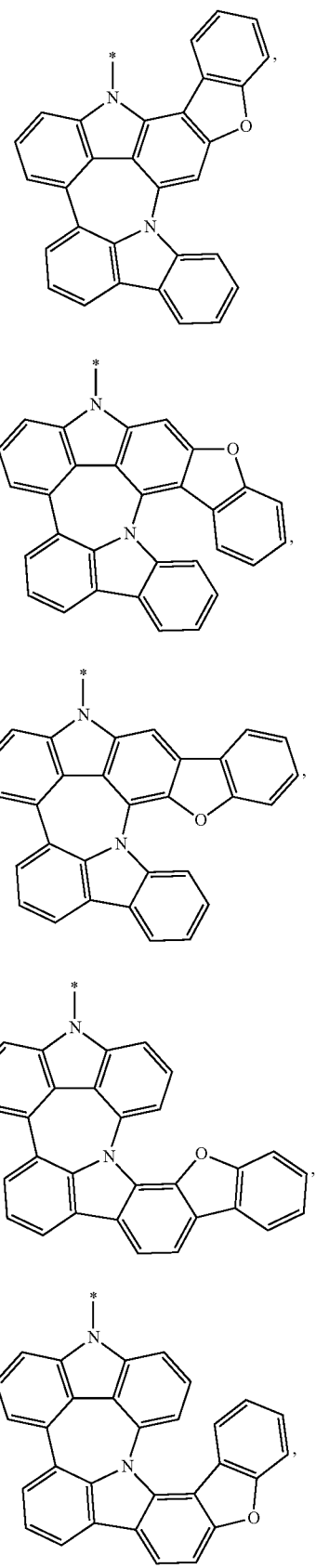

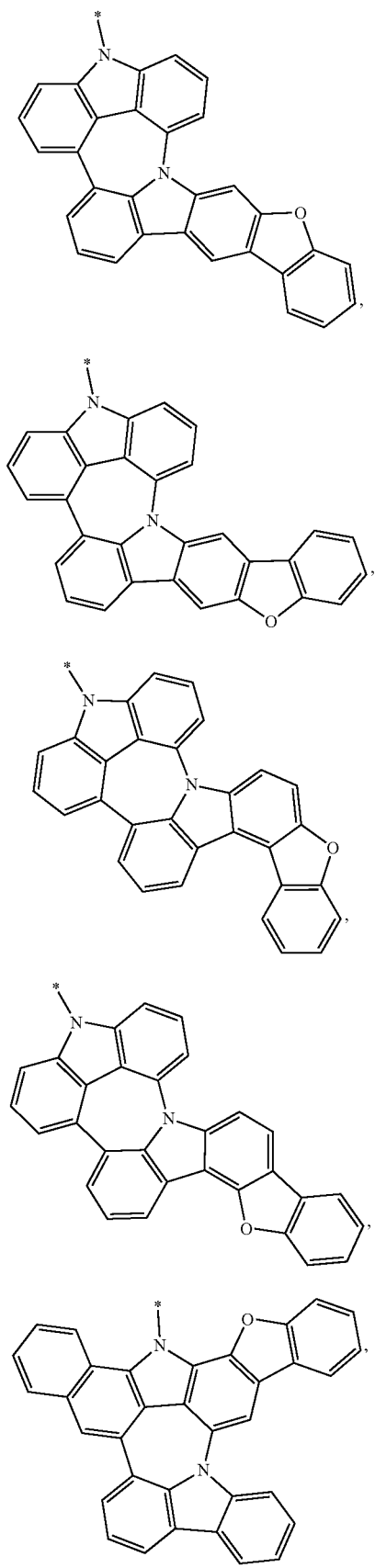
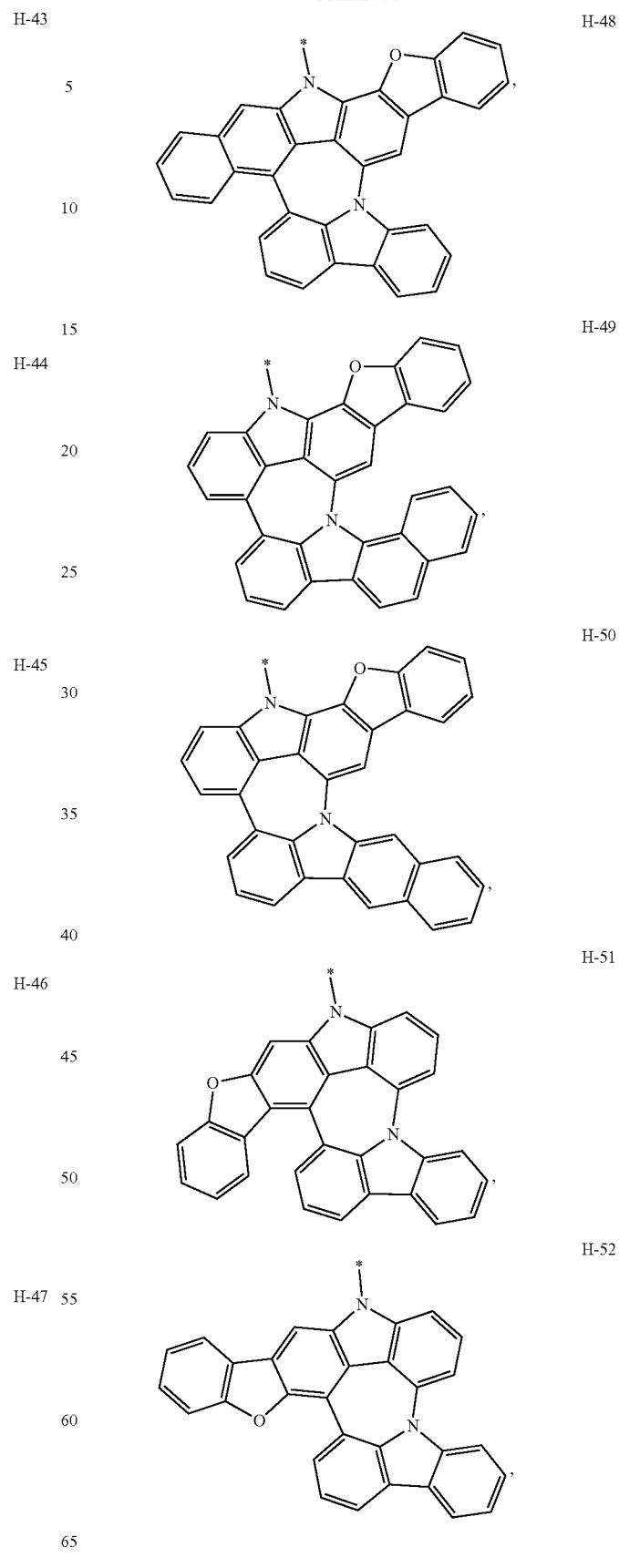

-continued
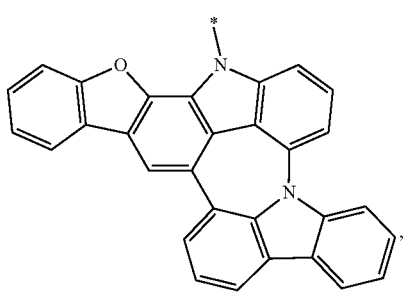
H-53
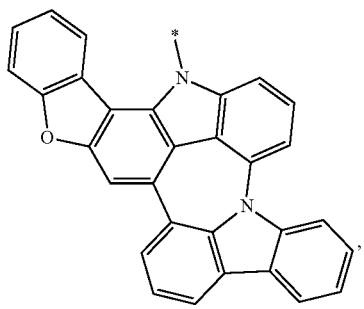
H-54
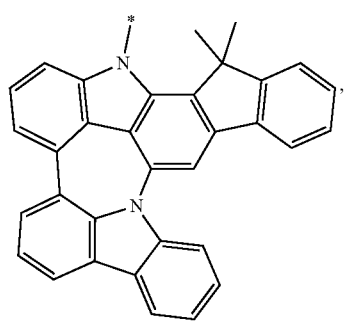
H-55
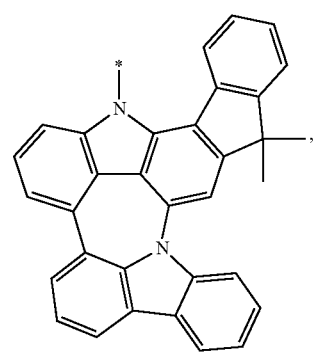
H-56
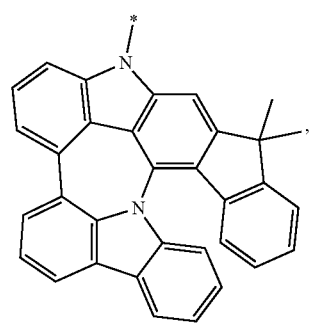
H-57
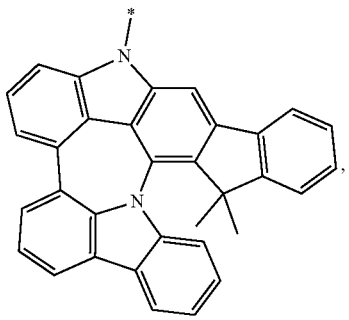
H-58
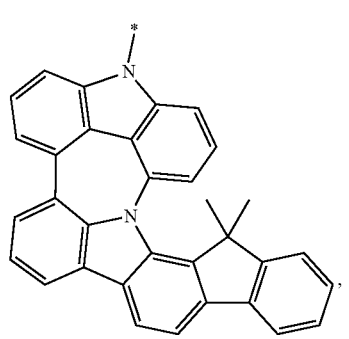
H-59
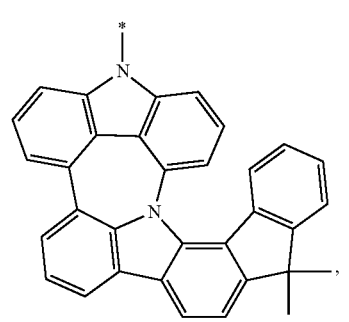
H-60
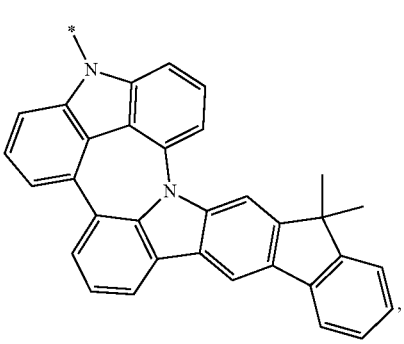
H-61
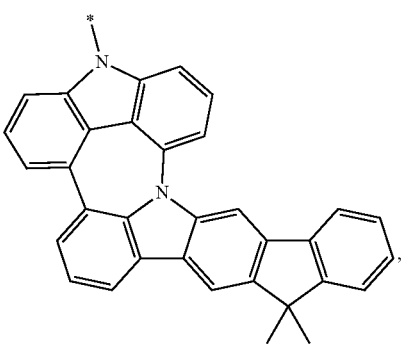
H-62

H-63
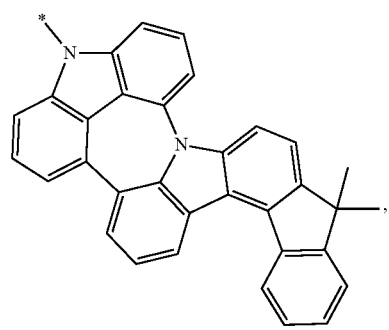
H-64
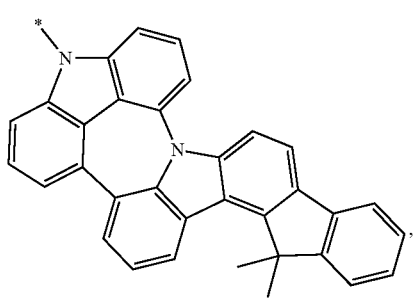
H-65
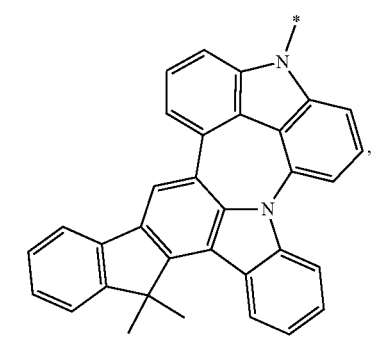
H-66
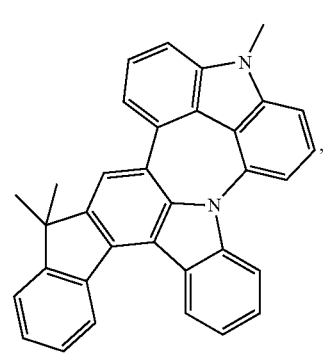
H-67
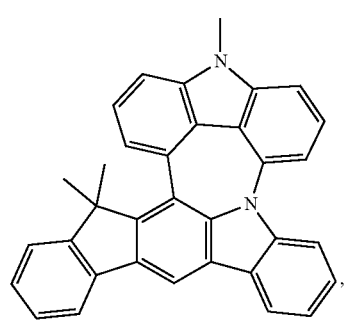
H-68
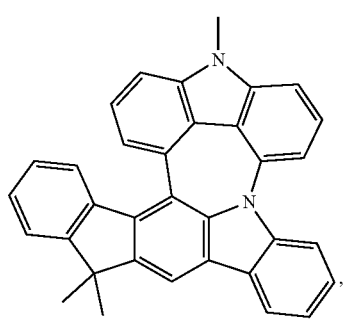
H-69
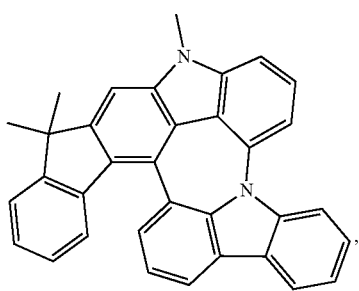
H-70
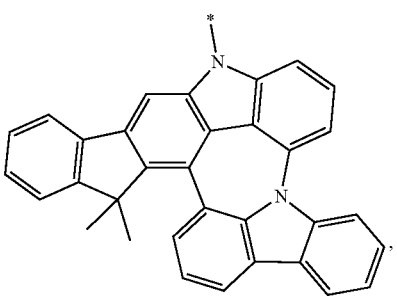
H-71
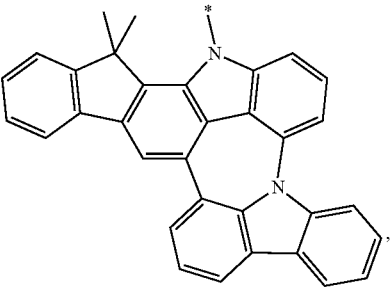
H-72
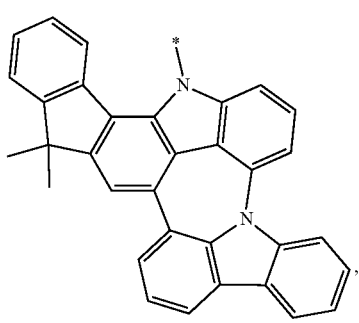

-continued
H-73
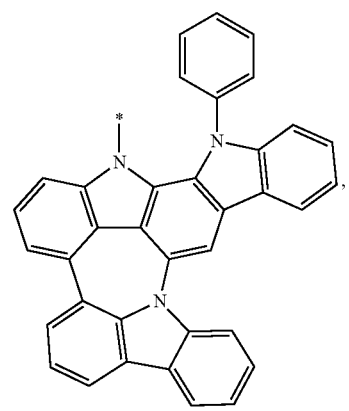
H-74
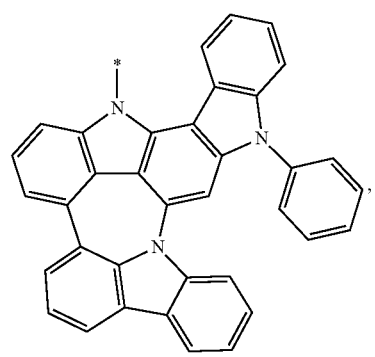
H-75
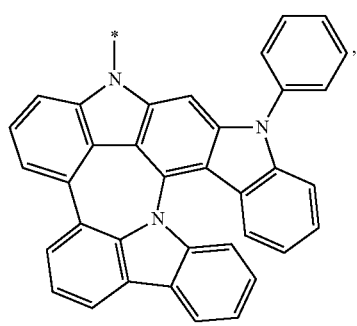
H-76
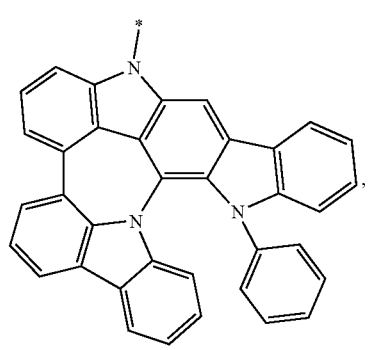
-continued
H-77
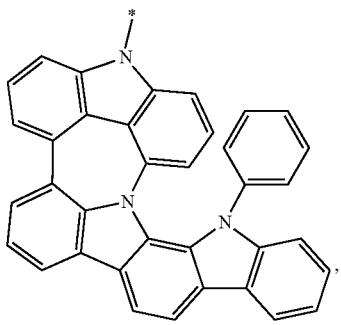
H-78
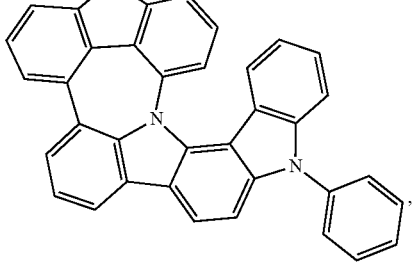
H-79
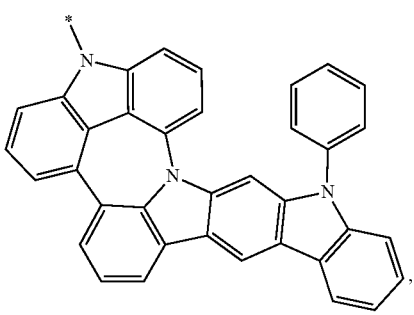
H-80
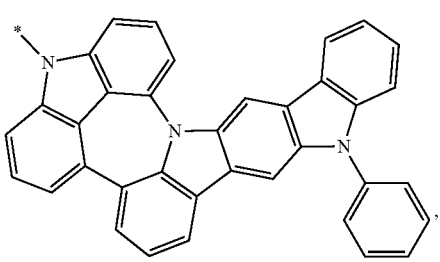
H-81
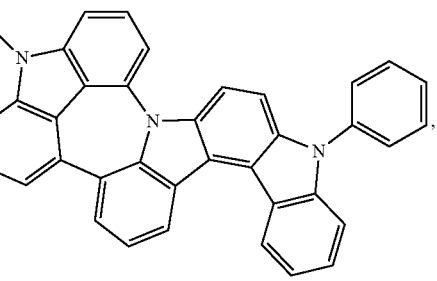

-continued
H-82
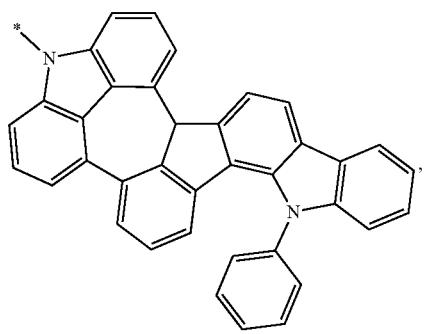
H-83
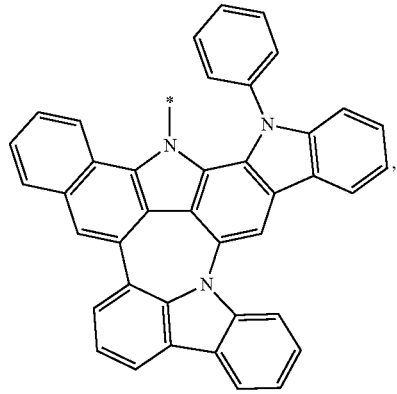
H-84
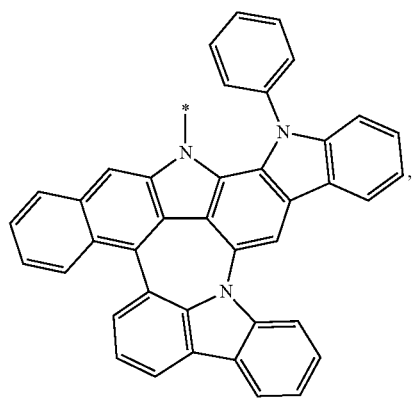
H-85
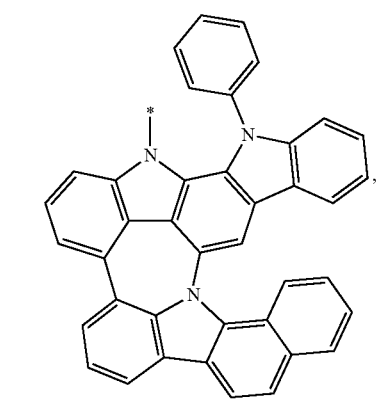
-continued
H-86
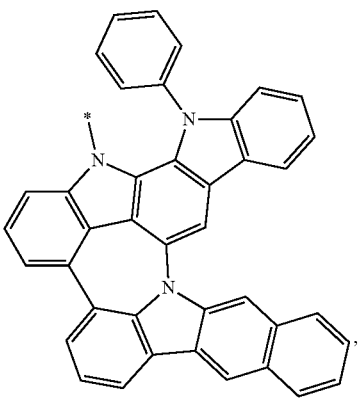
H-87
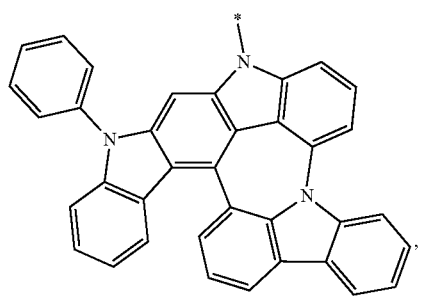
H-88
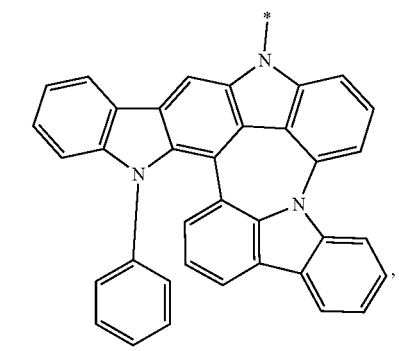
H-89
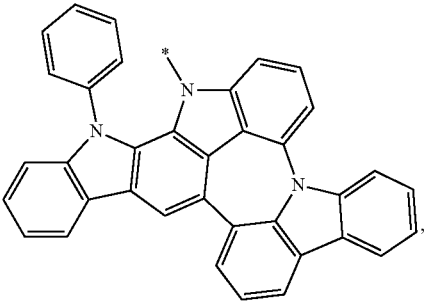

-continued
H-90
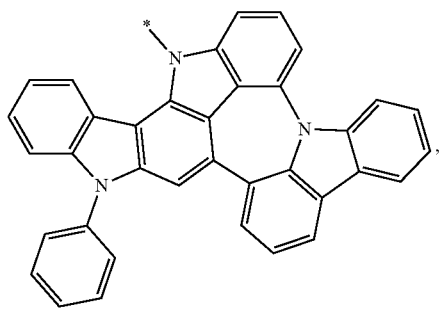
H-91
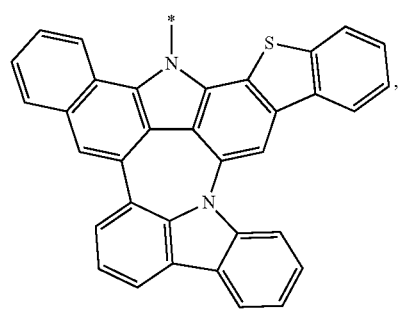
H-92
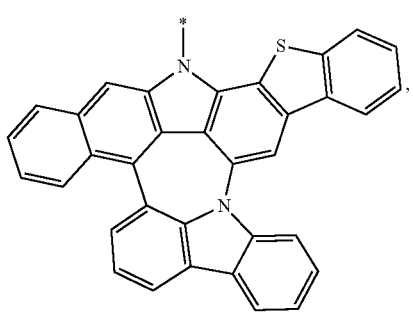
H-93
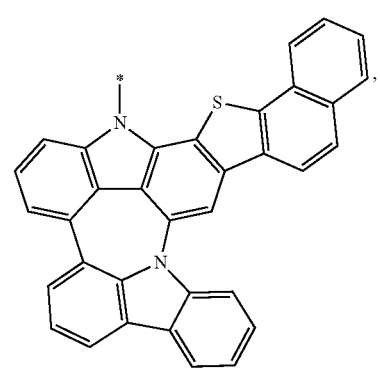
H-94
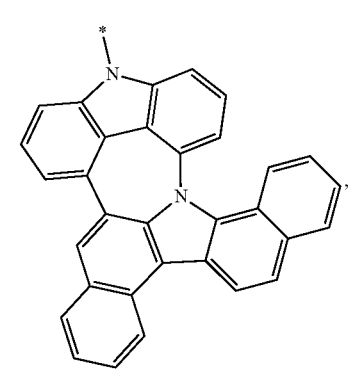
-continued
H-95
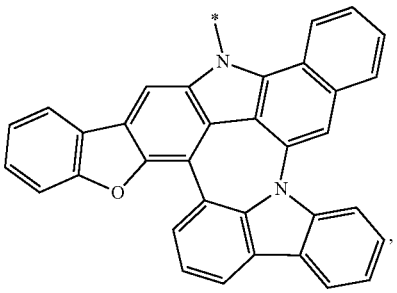
H-96
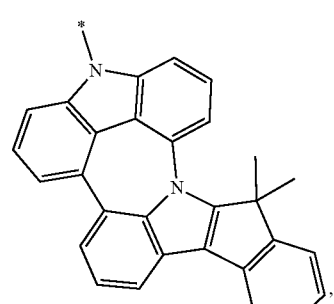
H-97
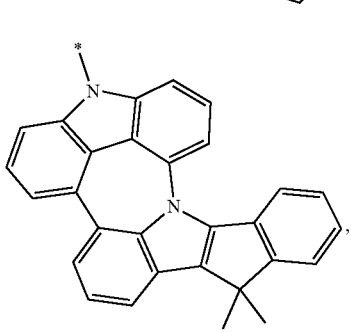
H-98
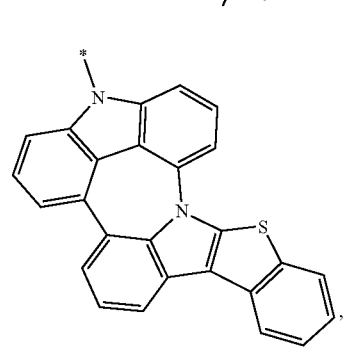
H-99
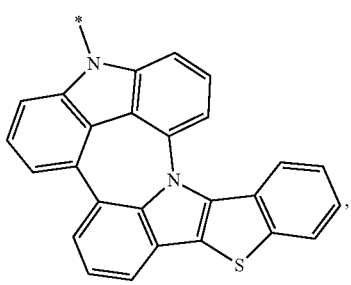

H-100
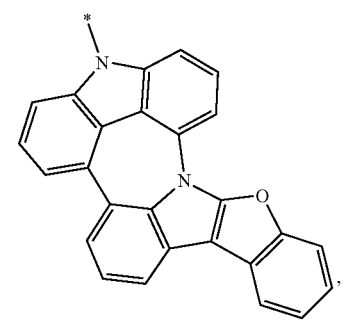
H-101
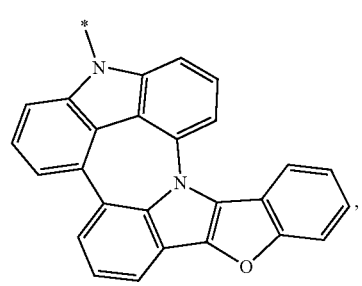
H-102
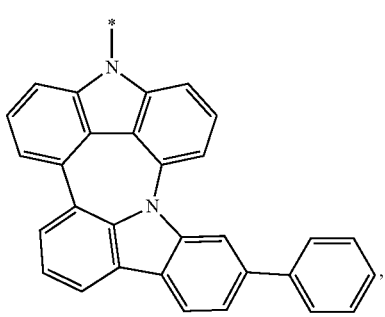
H-103
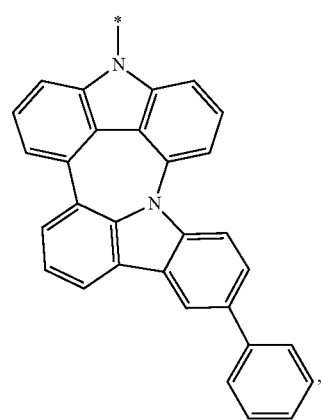
H-104
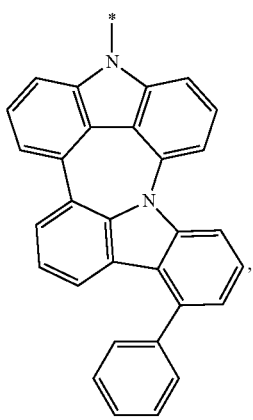
H-105
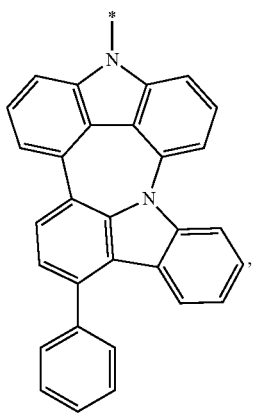
H-106
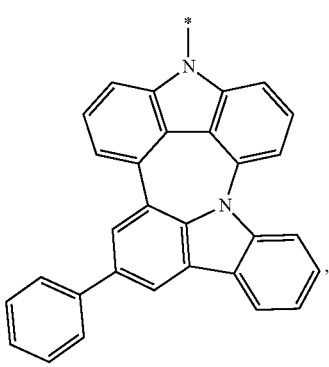
H-107
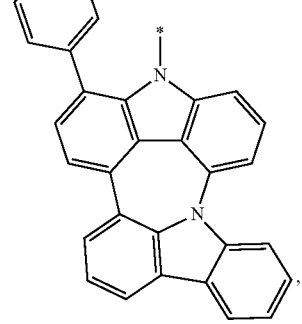

H-108
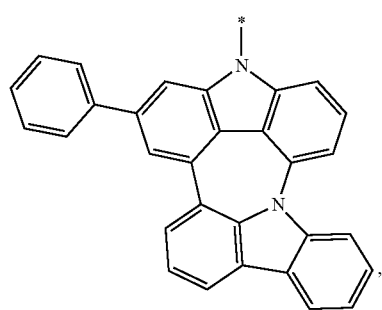
H-109
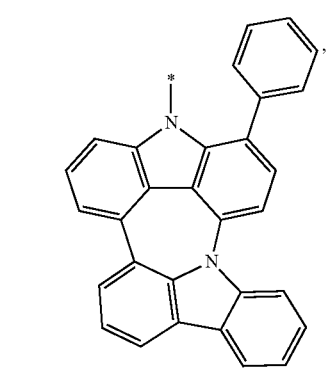
H-110
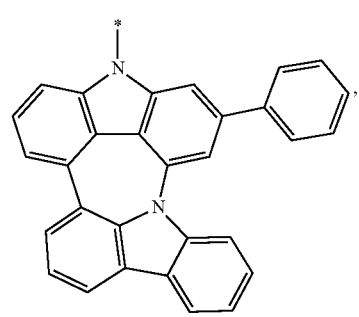
H-111
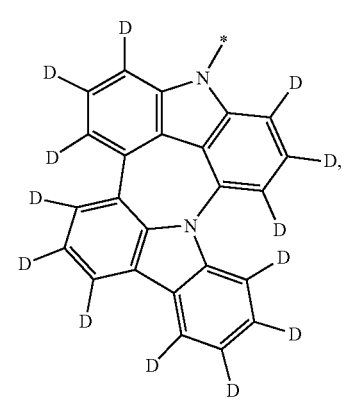
H-112
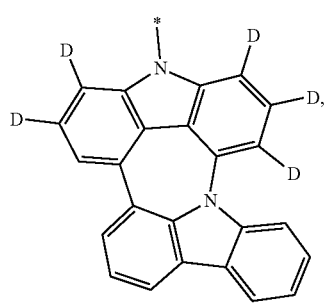
H-113
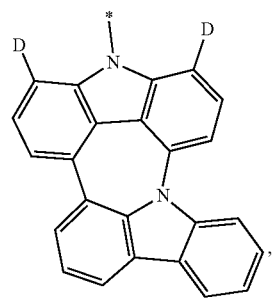
H-114
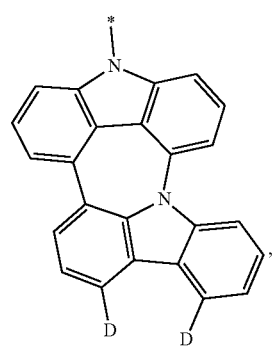
H-115
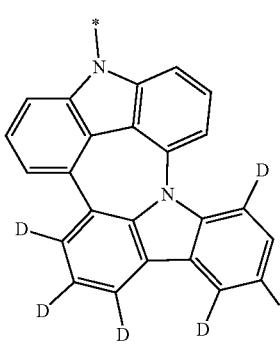
H-116
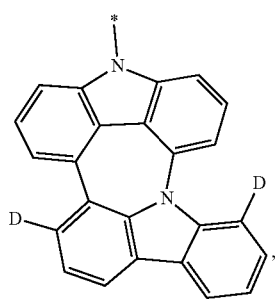

-continued

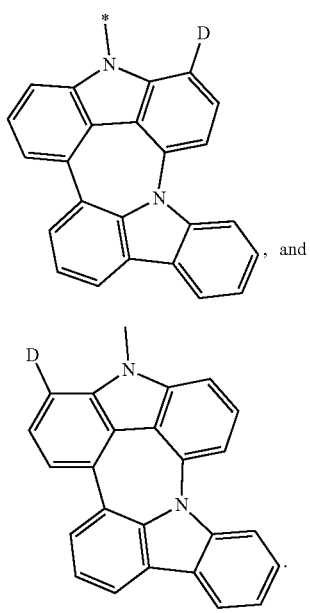

H-117

, and

H-118

According to an embodiment of the present disclosure, wherein hydrogens in the above structures H-1 to H-118 may be partially or fully substituted by deuterium.

According to an embodiment of the present disclosure, wherein the E has a structure represented by Formula 2-a, Formula 2-b or Formula 2-c:

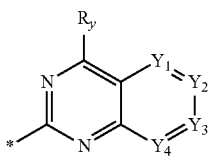

Formula 2-a

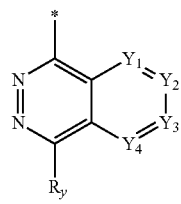

Formula 2-b

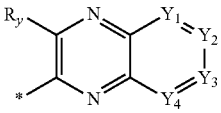

Formula 2-c wherein $Y_1$ to $Y_4$ are, at each occurrence identically or differently, selected from $CR_y$ or $CR_z$, and at least one of $Y_1$ to $Y_4$ is selected from $CR_z$;

wherein $R_y$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

wherein $R_z$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof, wherein adjacent substituents $R_y$ can be optionally joined to form a ring.

According to an embodiment of the present disclosure, wherein in Formula 2-a, Formula 2-b or Formula 2-c, one of $Y_1$ to $Y_4$ is selected from $CR_z$, and the other of $Y_1$ to $Y_4$ are each independently selected from $CR_y$.

According to an embodiment of the present disclosure, wherein in Formula 2-a, Formula 2-b or Formula 2-c, two of $Y_1$ to $Y_4$ are selected from $CR_z$, and the other of $Y_1$ to $Y_4$ are each independently selected from $CR_y$.

According to an embodiment of the present disclosure, wherein in Formula 2-a, Formula 2-b or Formula 2-c, $Y_1$ to $Y_4$ are, at each occurrence identically or differently, selected from $CR_y$ or $CR_z$, and at least one of $Y_1$ to $Y_4$ is selected from $CR_z$;

wherein the $R_z$ is, at each occurrence identically or differently, selected from deuterium, substituted or unsubstituted aryl having 6 to 18 carbon atoms, substituted or unsubstituted heteroaryl having 3 to 18 carbon atoms, or combinations thereof;

the $R_y$ is, at each occurrence identically or differently, selected from the group consisting of: hydrogen, deuterium, halogen, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, and combinations thereof.

According to an embodiment of the present disclosure, wherein in Formula 2-a, Formula 2-b or Formula 2-c, $Y_1$ to $Y_4$ are, at each occurrence identically or differently, selected from $CR_y$ or $CR_z$, and at least one of $Y_1$ to $Y_4$ is selected from $CR_z$;

wherein the $R_z$ is, at each occurrence identically or differently, selected from deuterium, phenyl, biphenyl, naphthyl, or combinations thereof;

the $R_y$ is, at each occurrence identically or differently, selected from the group consisting of: hydrogen, deuterium, fluorine, phenyl, biphenyl, naphthyl, and combinations thereof.

According to an embodiment of the present disclosure, wherein in the structures represented by Formula 2-a to Formula 2-c, the $R_y$ connected to the aza six-membered ring is selected from deuterium, substituted or unsubstituted aryl having 6 to 30 carbon atoms, or substituted or unsubstituted heteroaryl having 3 to 30 carbon atoms.

According to an embodiment of the present disclosure, wherein in the structure represented by Formula 2-a to Formula 2-f, the $R_y$ connected to the aza six-membered ring is selected from deuterium, phenyl, biphenyl, naphthyl, 4-cyanophenyl, dibenzofuryl, dibenzothienyl, triphenylene, carbazolyl, 9-phenylcarbazolyl, 9,9-dimethylfluorenyl, pyridyl or phenylpyridyl.

According to an embodiment of the present disclosure, wherein the E is selected from the group consisting of the following structures:

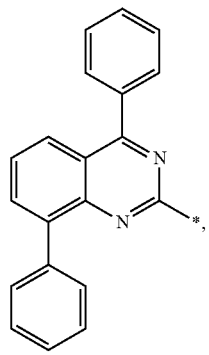

E-1

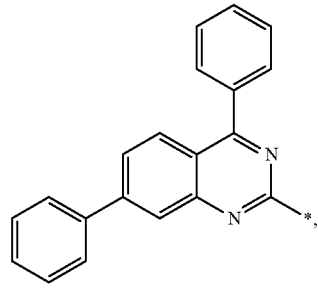

E-2

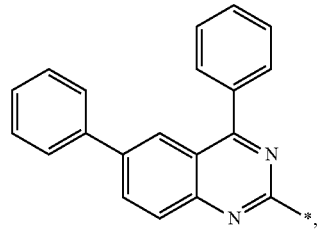

E-3

-continued

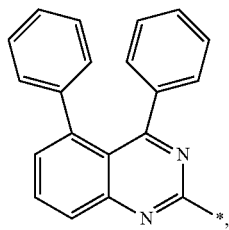

E-4

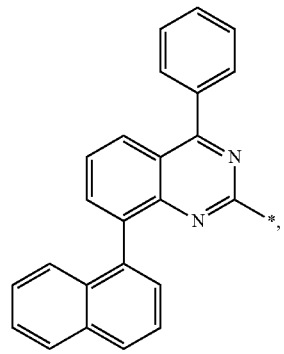

E-5

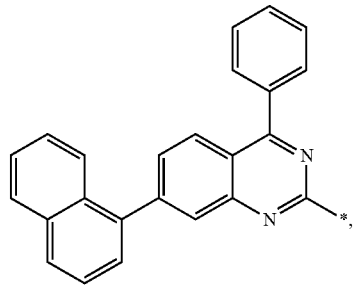

E-6

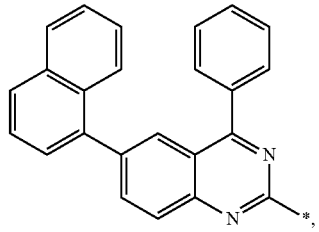

E-7

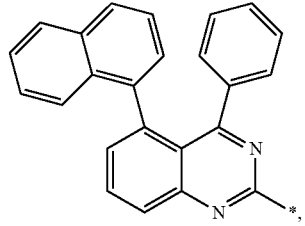

E-8

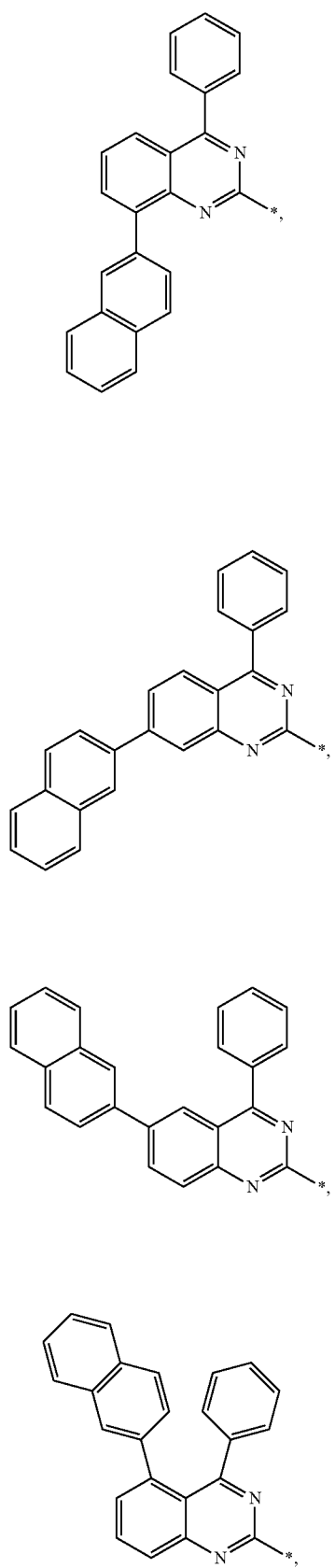
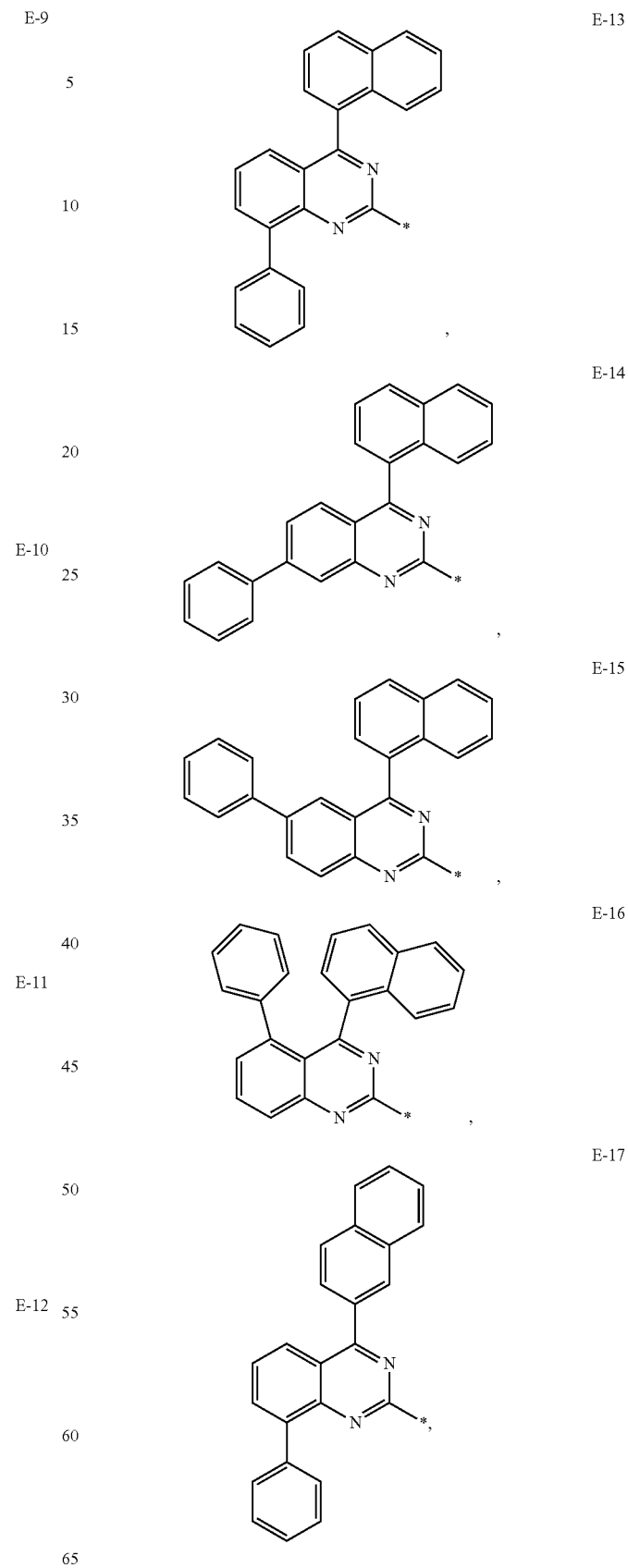

-continued
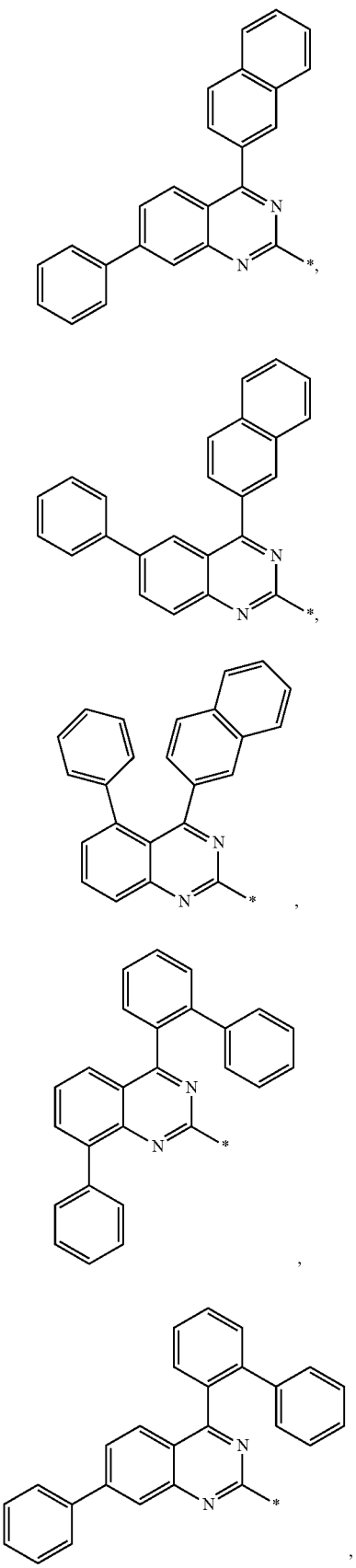
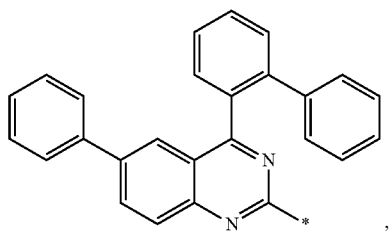
E-23
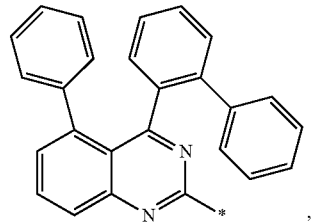
E-24
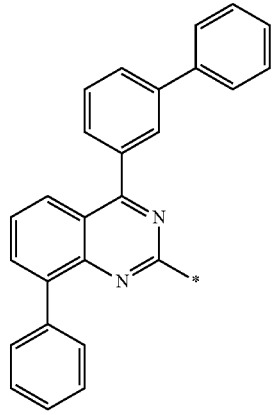
E-25
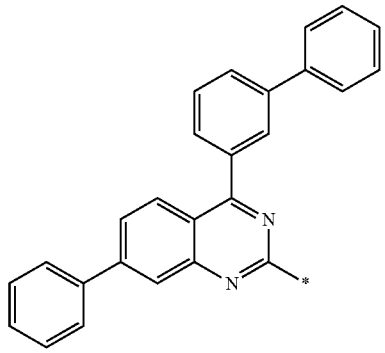
E-26
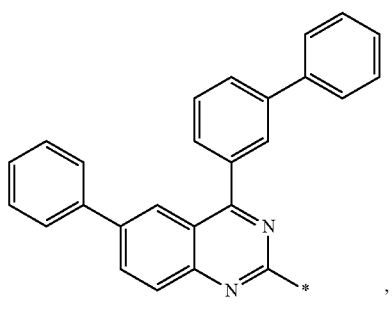
E-27

-continued

E-28

E-29

E-30

E-31

E-32

E-33

E-34

E-35

E-36

E-37
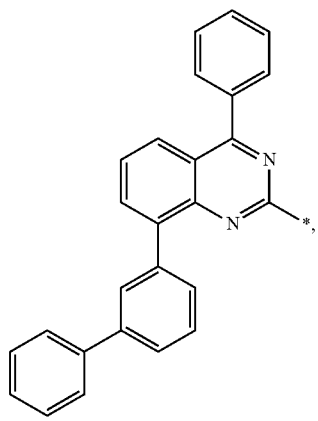
E-38
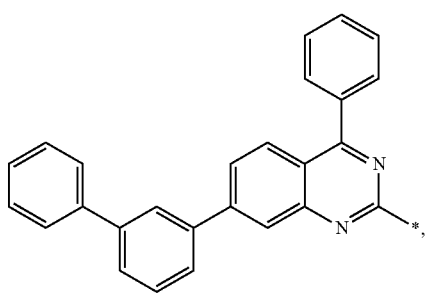
E-39
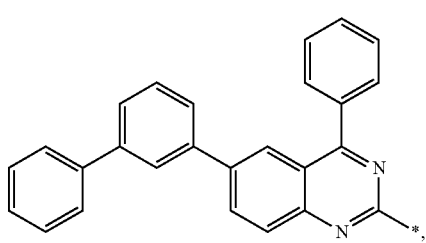
E-40
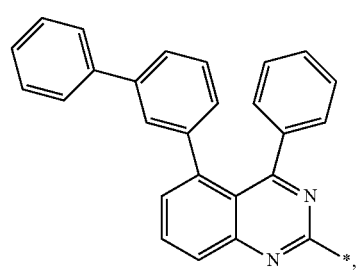
E-41
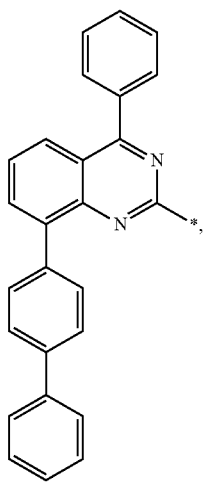
E-42
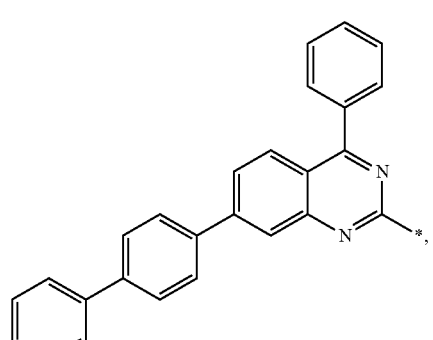
E-43
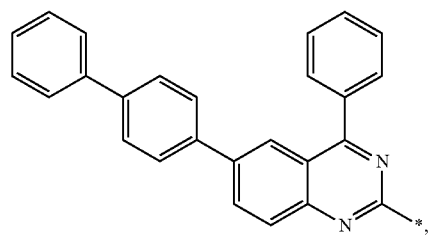
E-44
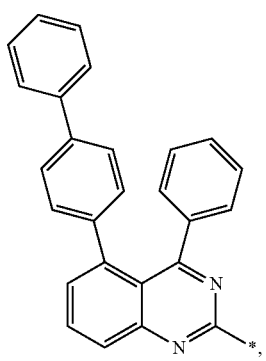

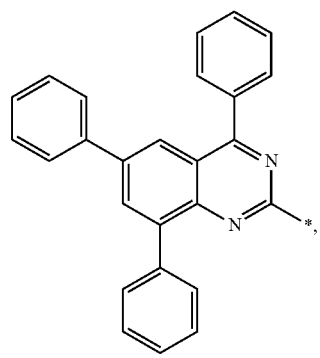
E-45
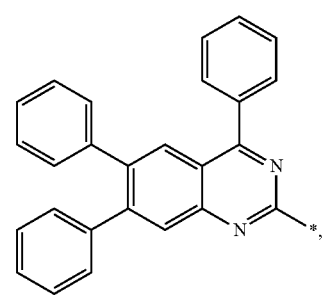
E-46
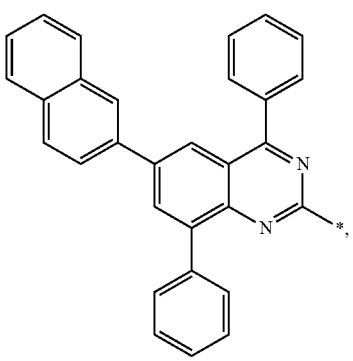
E-47
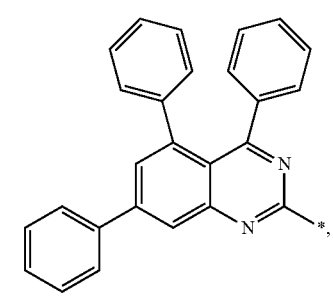
E-48
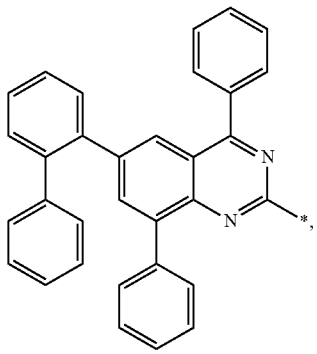
E-49
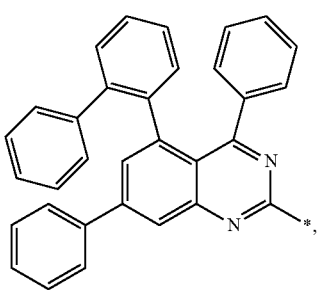
E-50
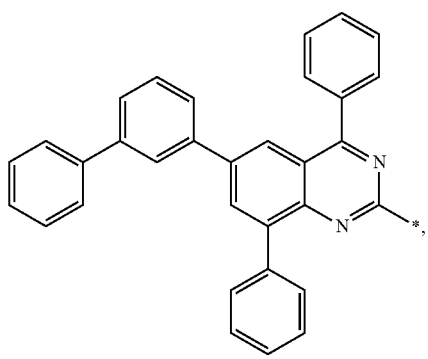
E-51
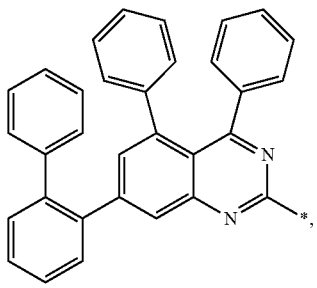
E-52
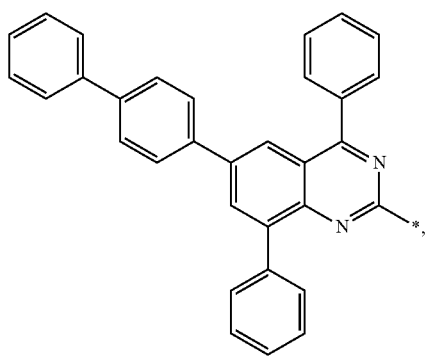
E-53

E-54
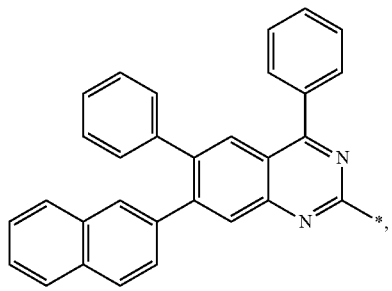
E-55
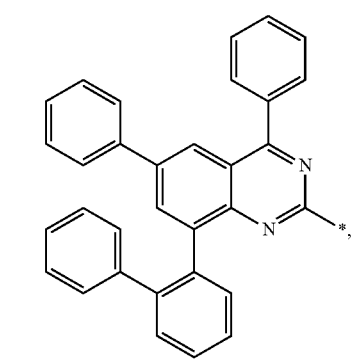
E-56
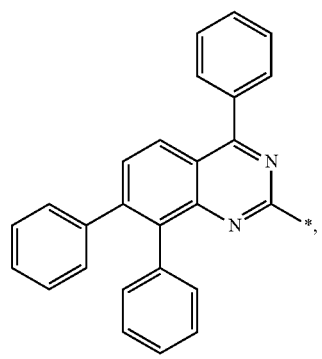
E-57
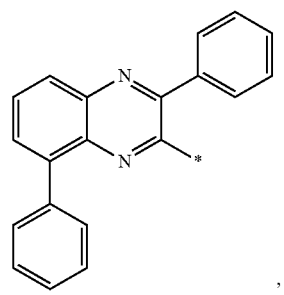
E-58
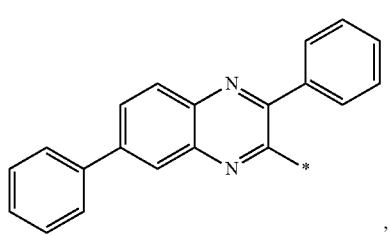
E-59
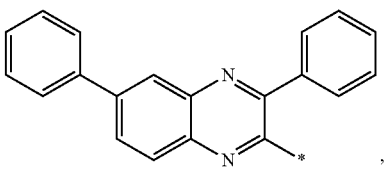
E-60
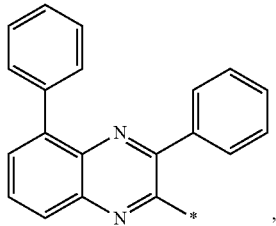
E-61
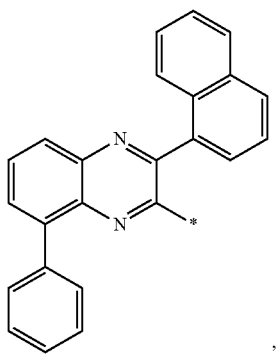
E-62
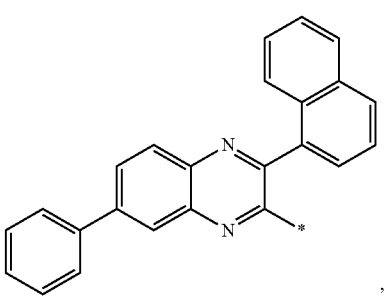
E-63
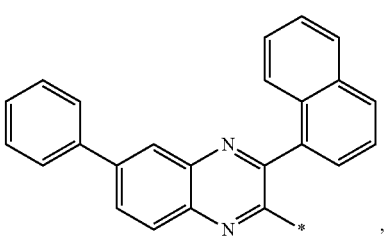
E-64
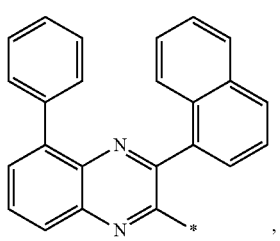

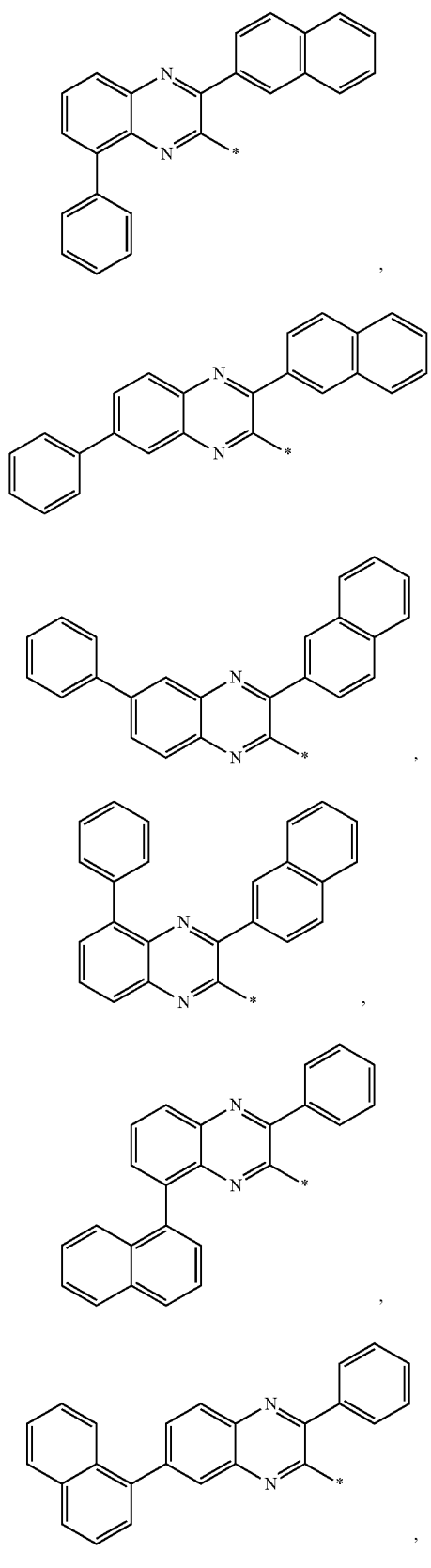
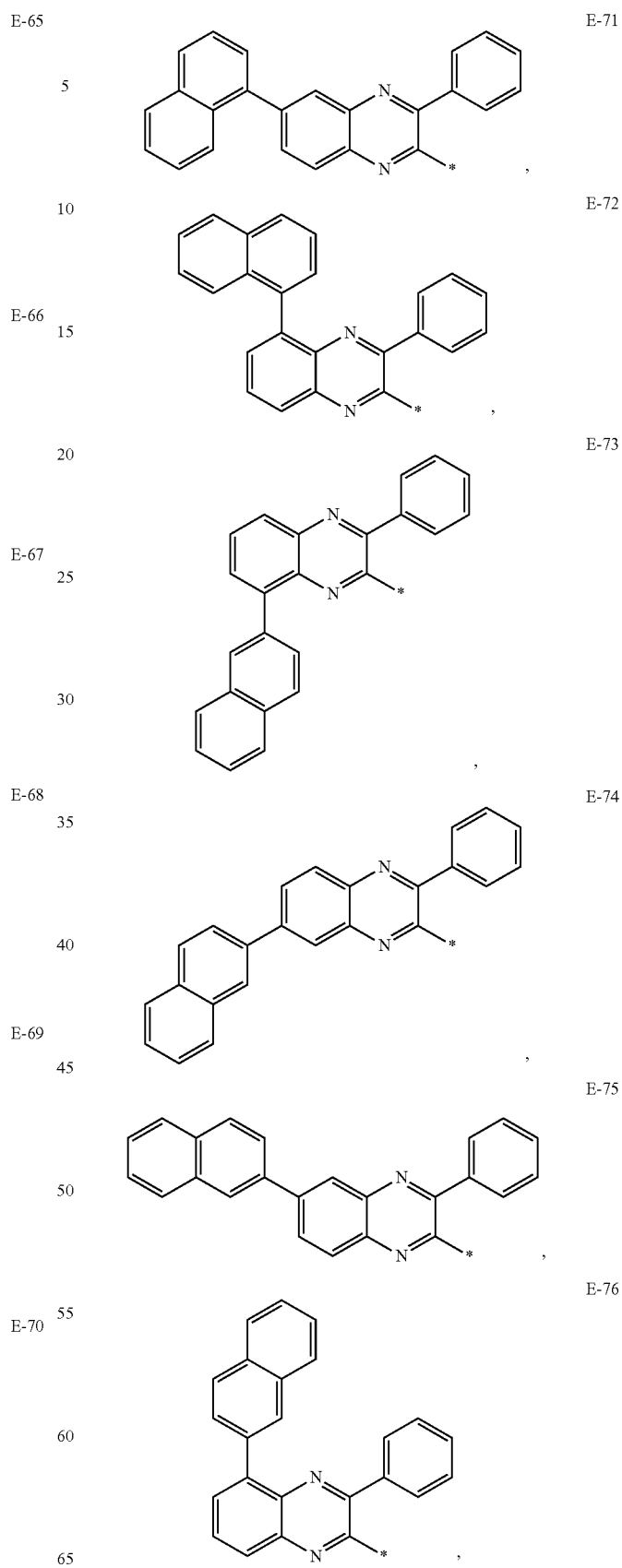

-continued

E-77

E-78

E-79

E-80

E-81

E-82

E-83

E-84

E-85

E-86

E-87
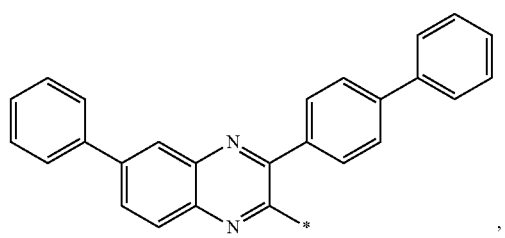
E-88
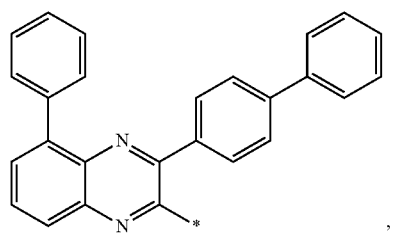
E-89
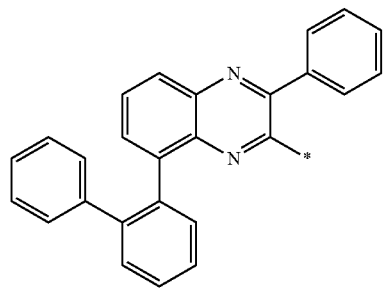
E-90
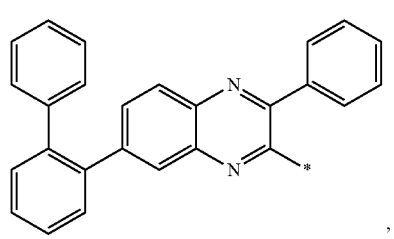
E-91
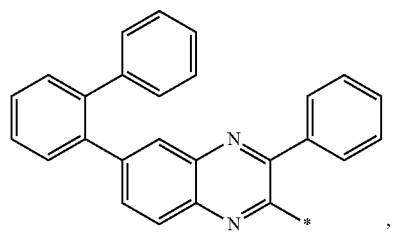
E-92
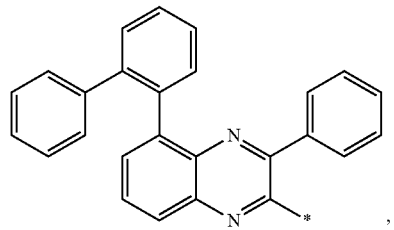
E-93
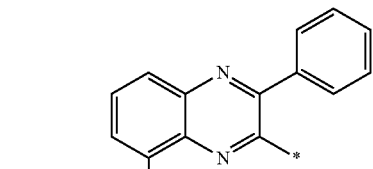
E-94
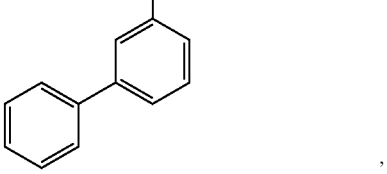
E-95
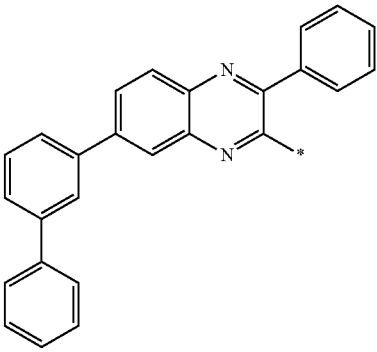
E-96
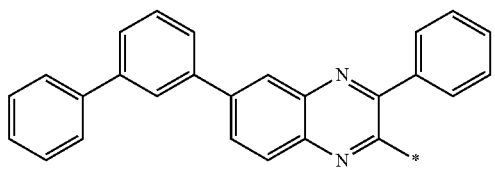
E-97
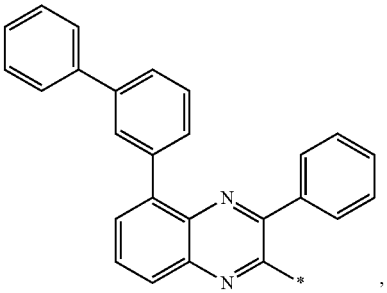
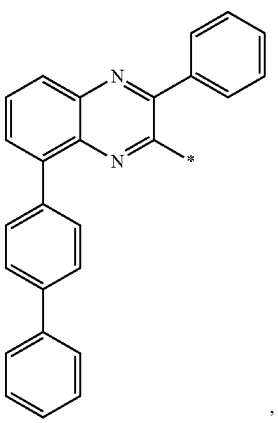

E-98
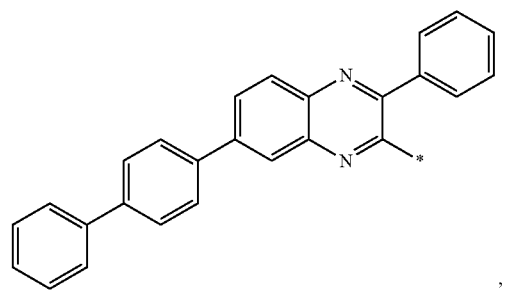
E-99
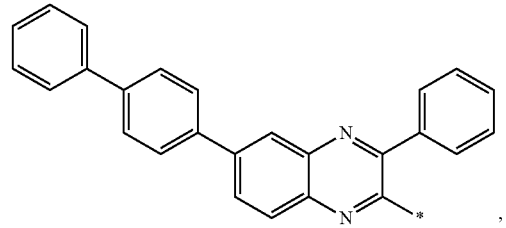
E-100
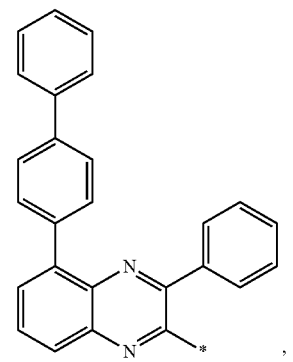
E-101
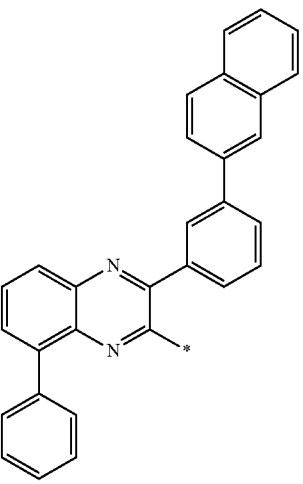
E-102
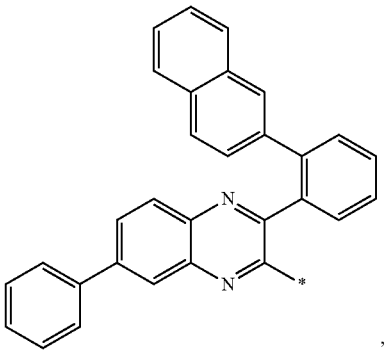
E-103
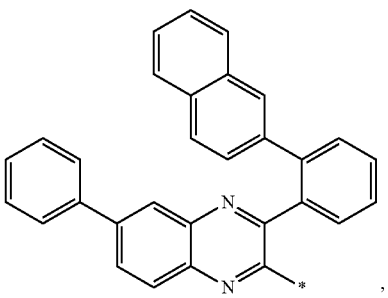
E-104
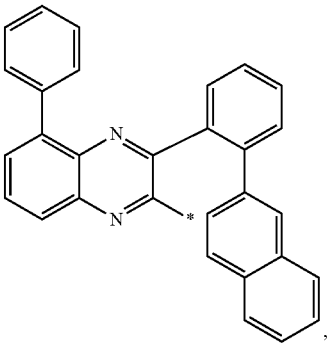
E-105
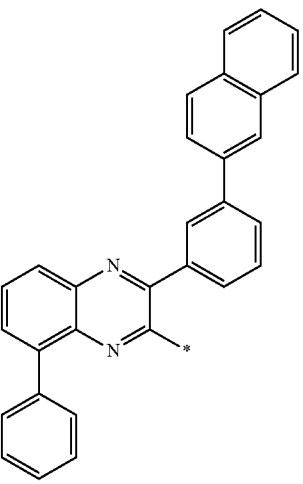

E-106
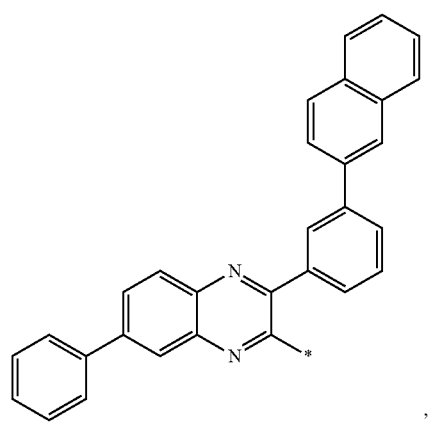
E-107
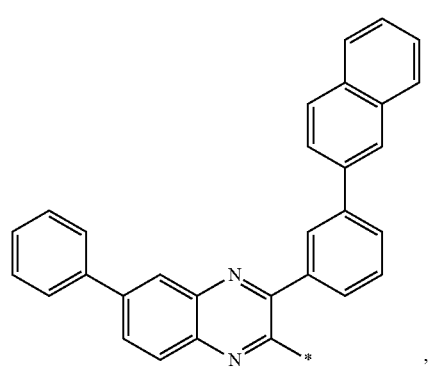
E-108
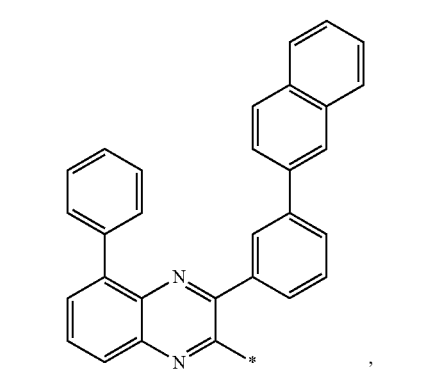
E-109
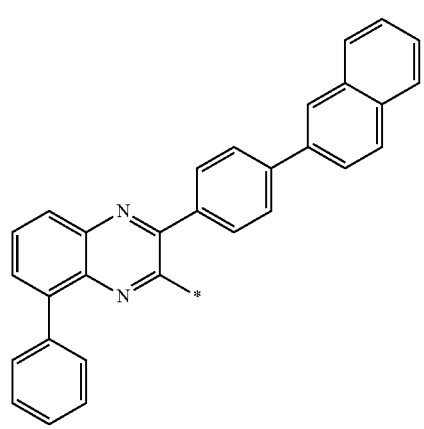
E-110
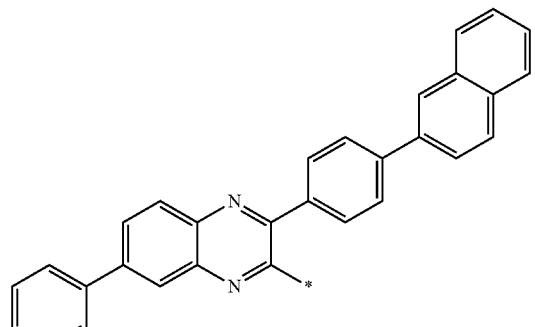
E-111
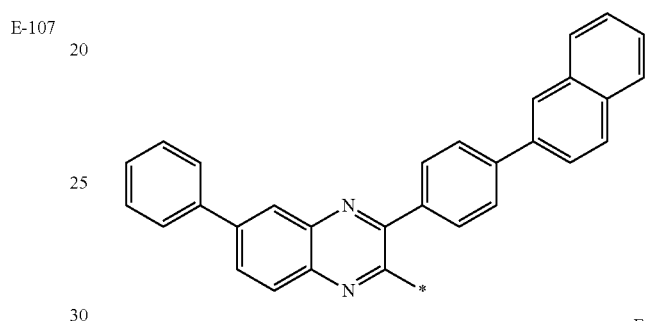
E-112
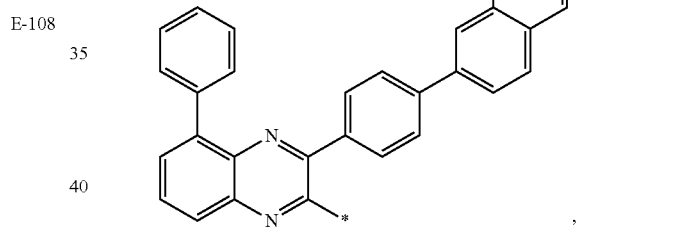
E-113
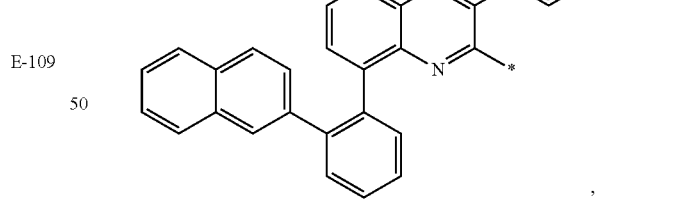
E-114
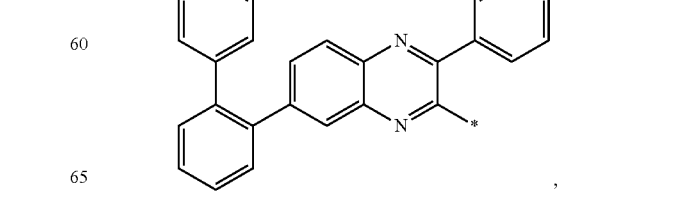

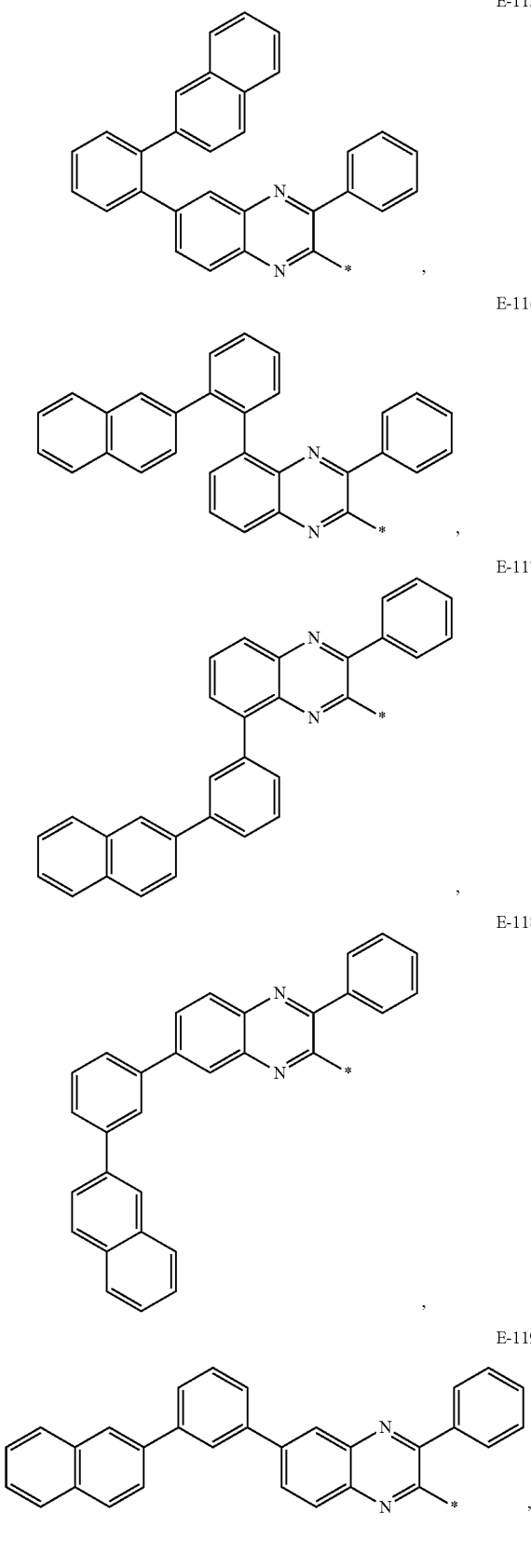
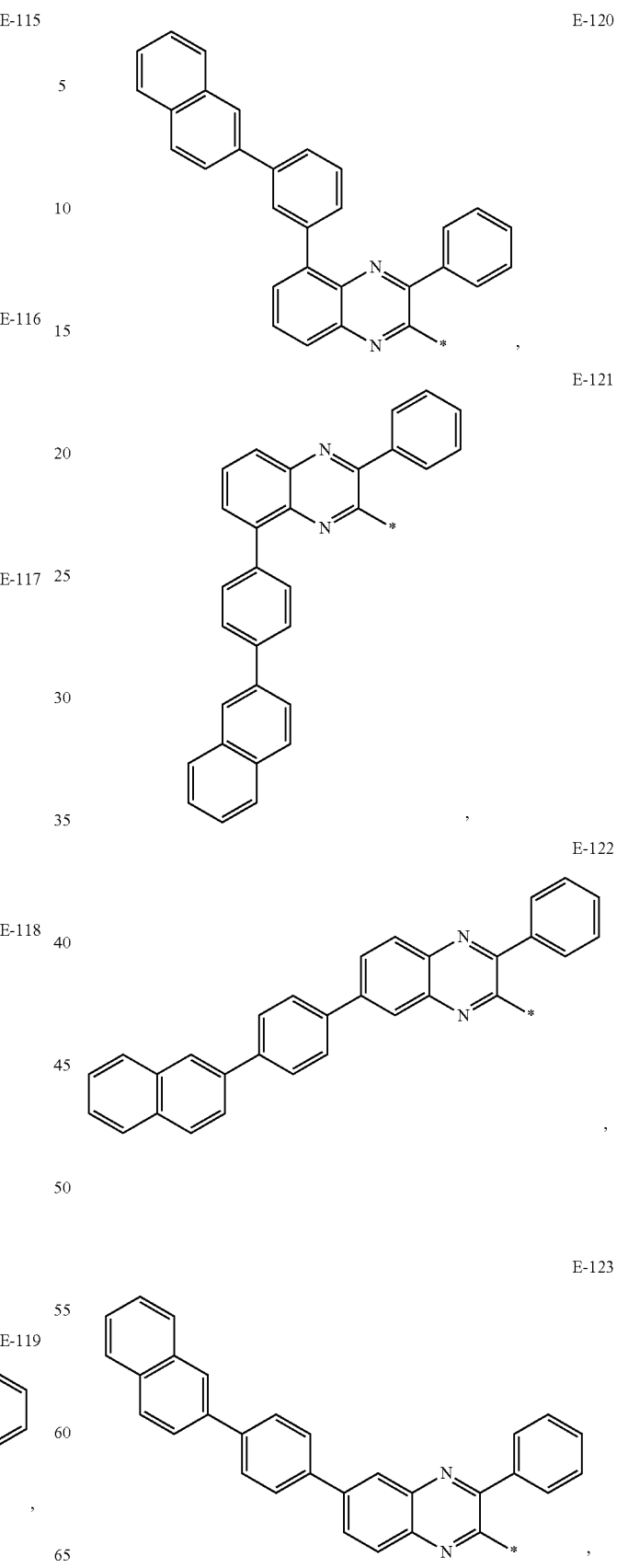

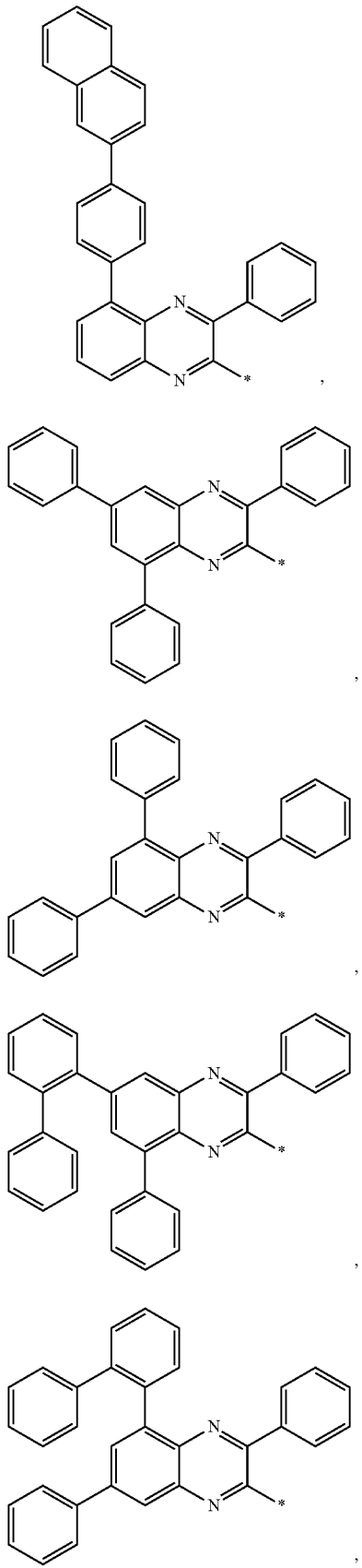
E-124
E-125
E-126
E-127
E-128
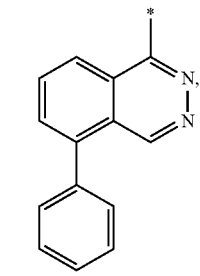
E-129
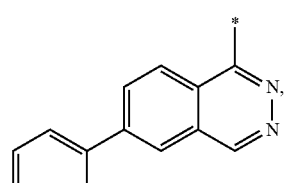
E-130
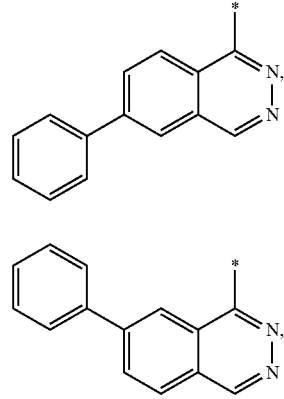
E-131
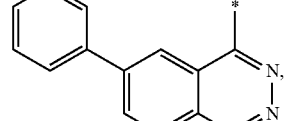
E-132
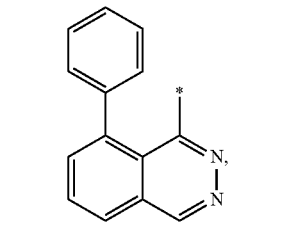
E-133
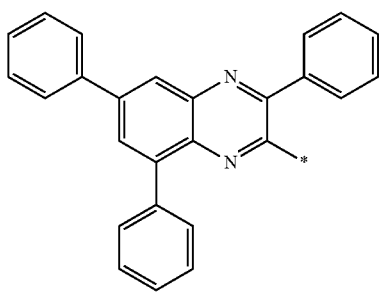
E-134
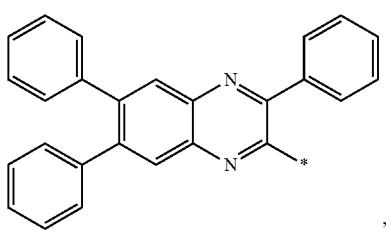

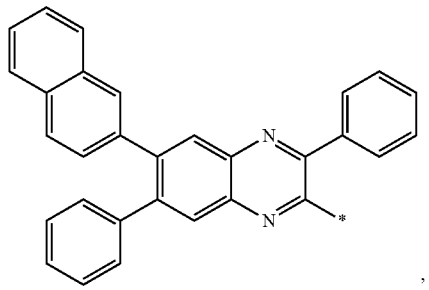
E-135
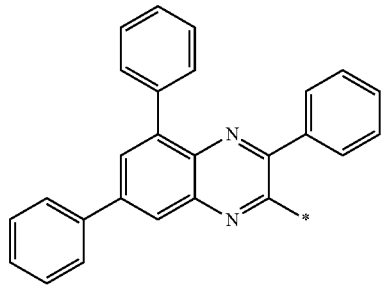
E-136
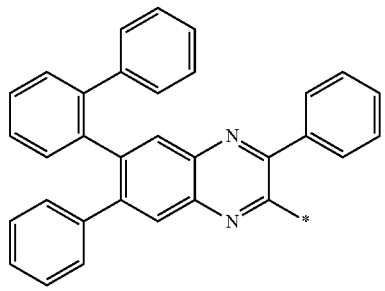
E-137
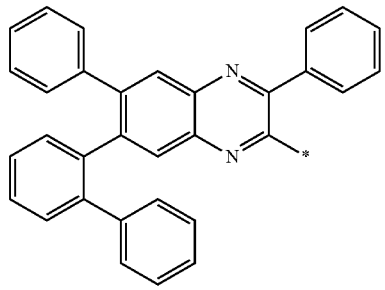
E-138
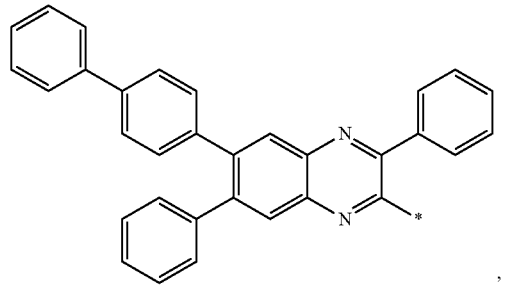
E-139
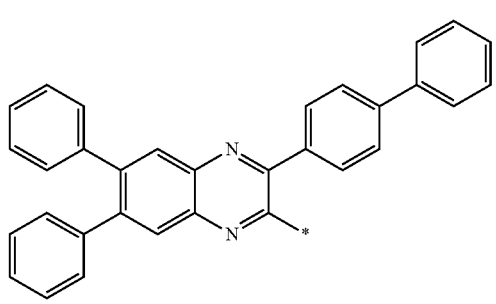
E-140
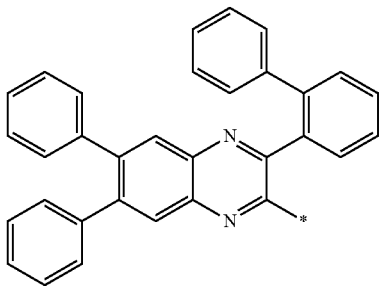
E-141
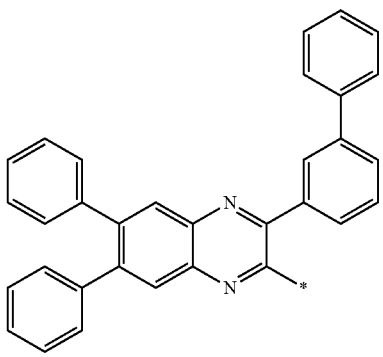
E-142
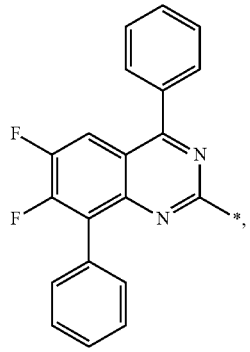
E-143

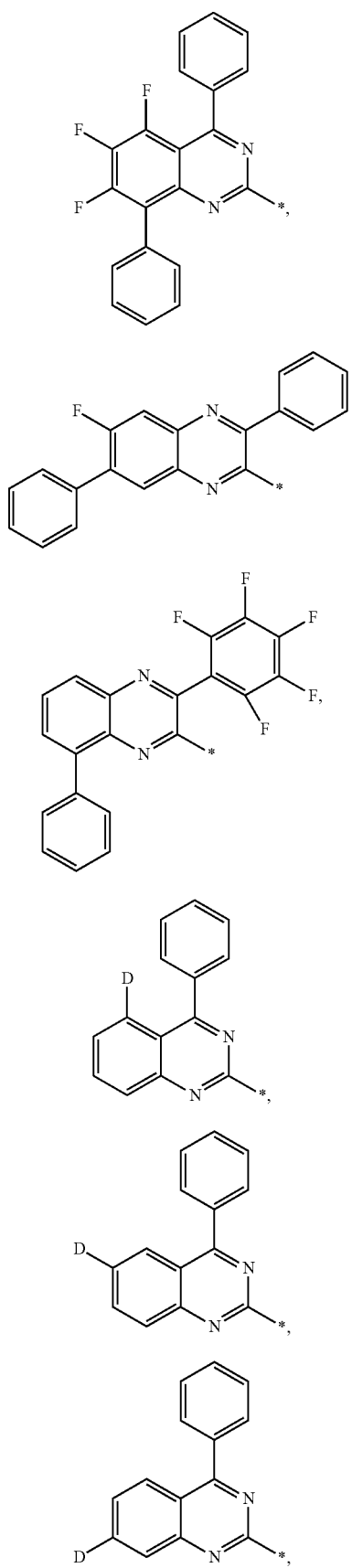
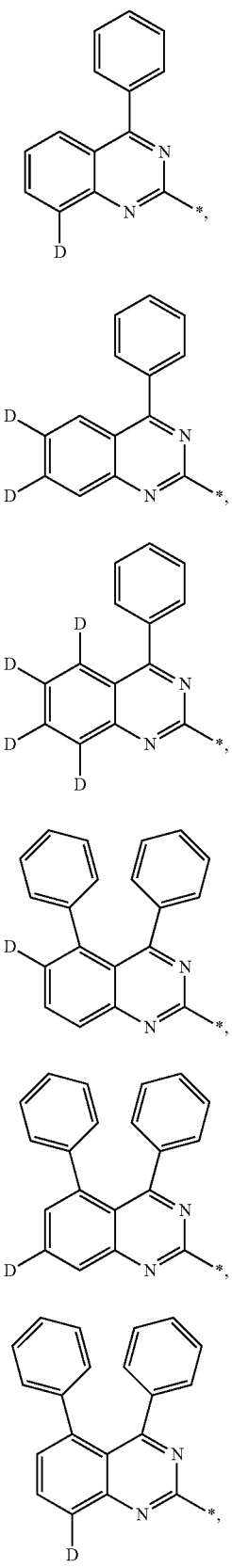

E-156
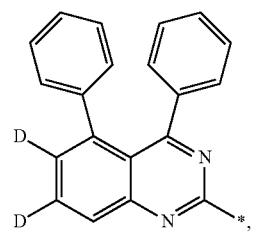
E-157
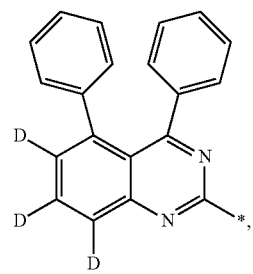
E-158
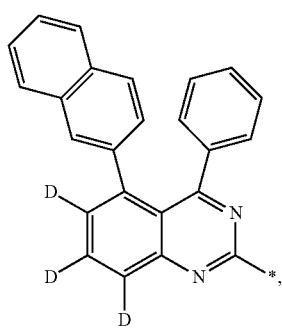
E-159
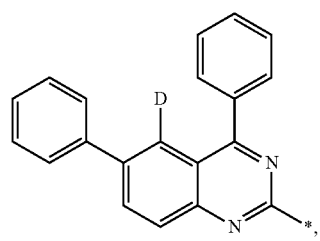
E-160
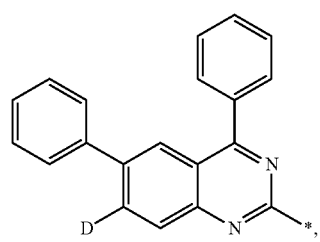
E-161
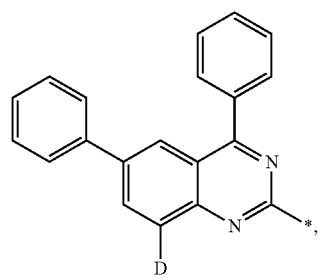
E-162
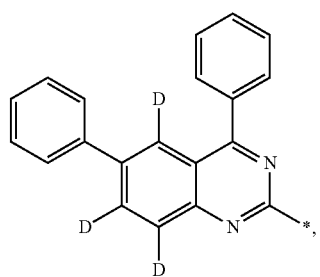
E-163
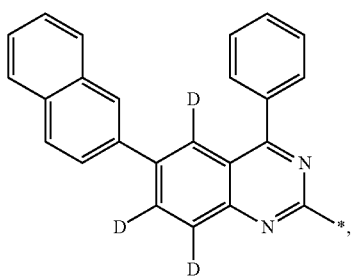
E-164
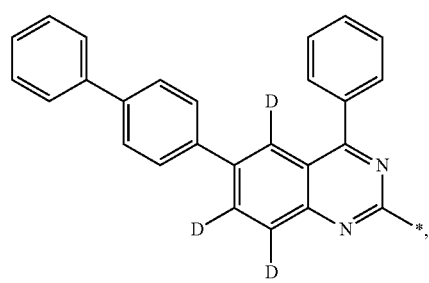
E-165
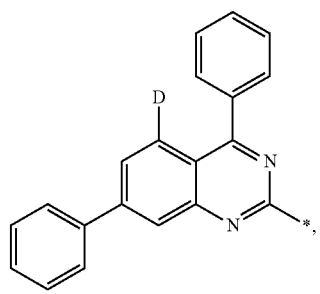
E-166
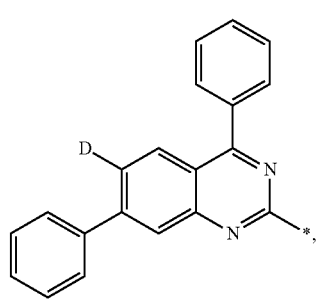

E-167
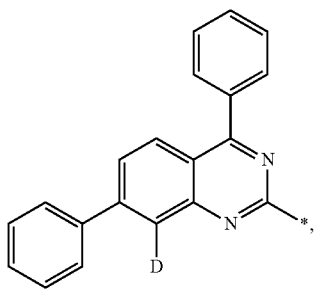
E-168
E-169
E-170
E-171
E-172
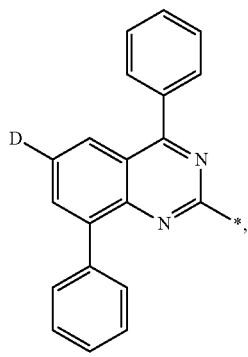
E-173
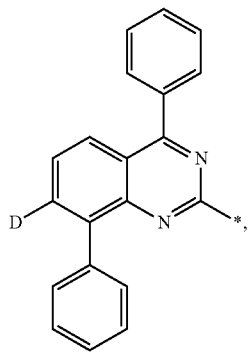
E-174
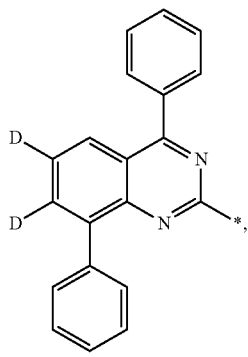
E-175
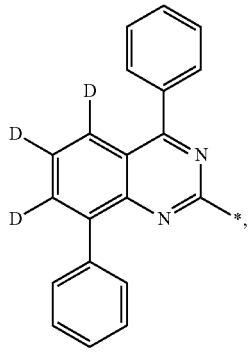

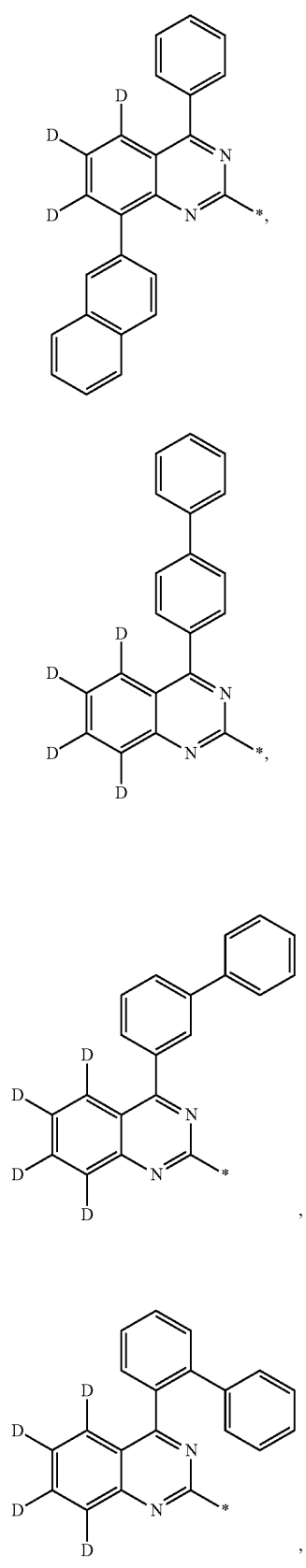

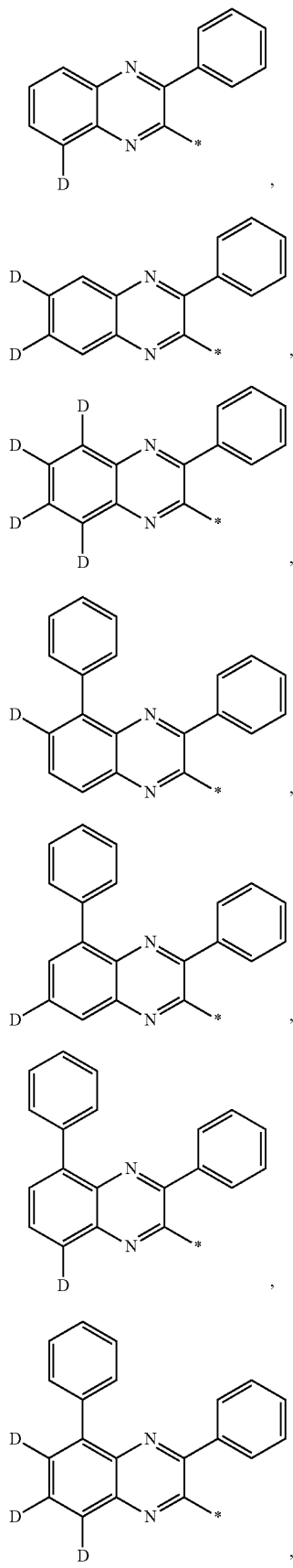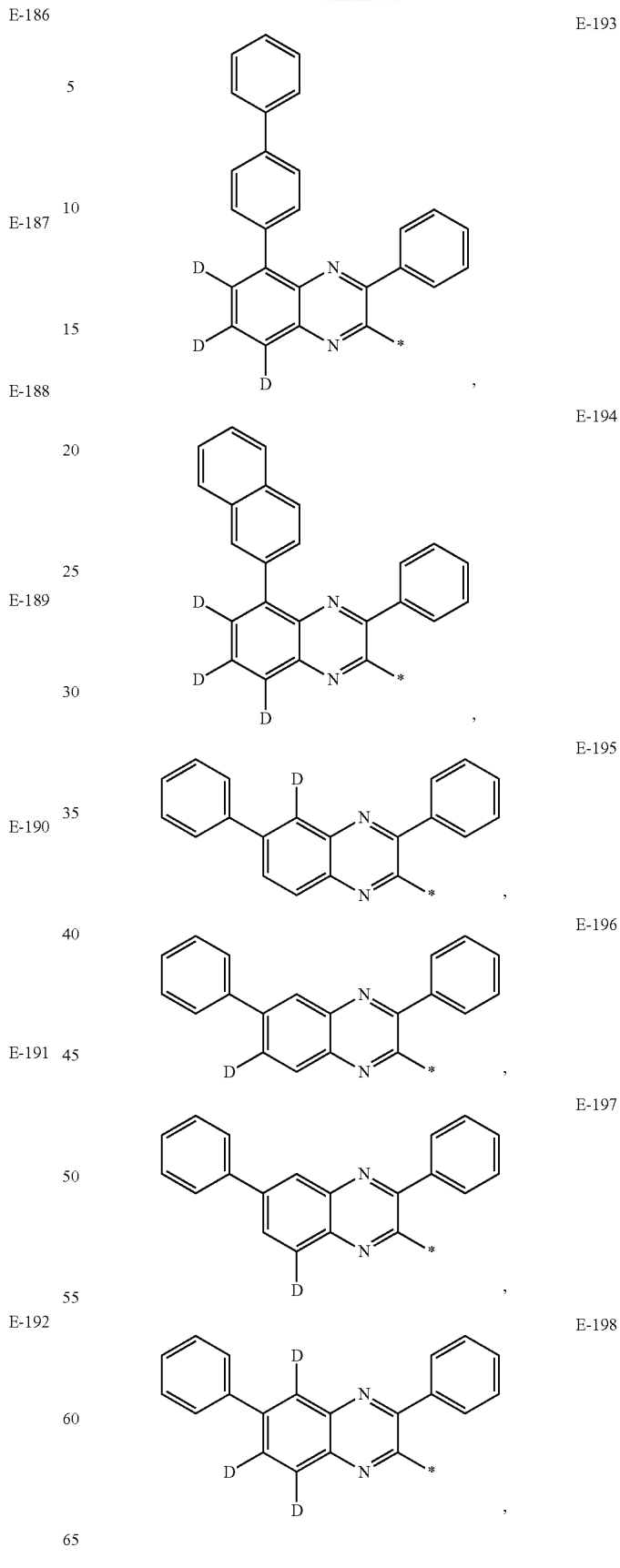

E-199
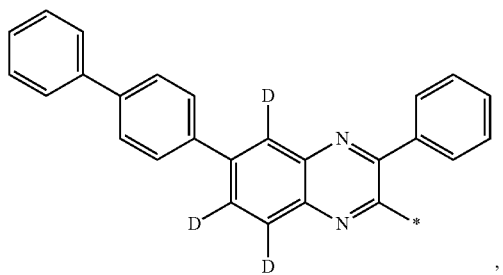
E-200
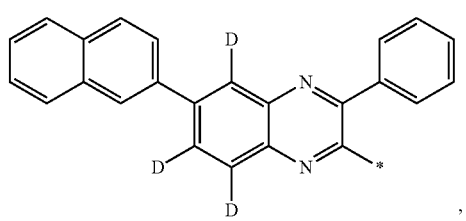
E-201
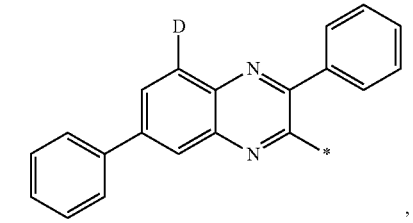
E-202
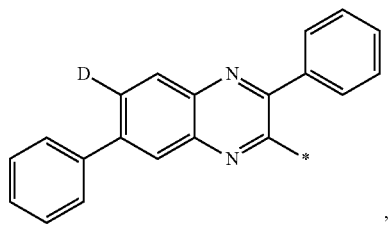
E-203
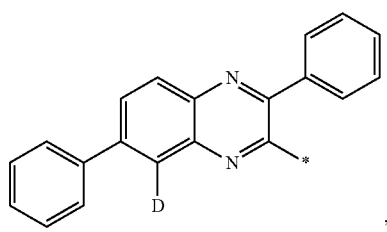
E-204
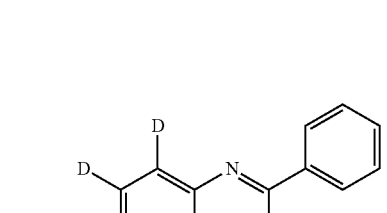
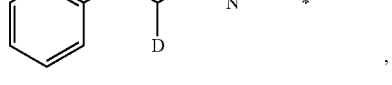
E-205
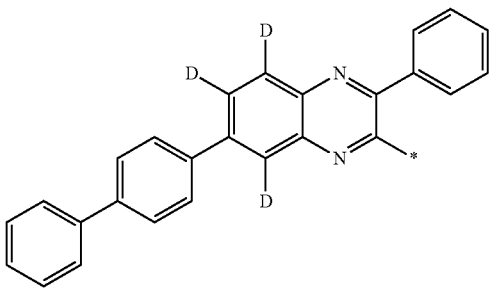
E-206
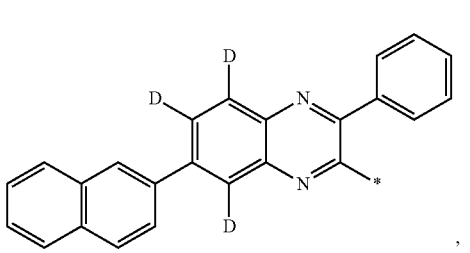
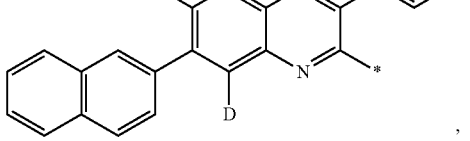
E-207
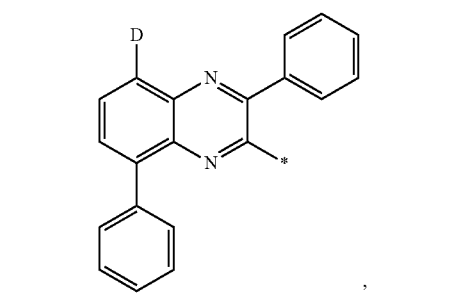
E-208
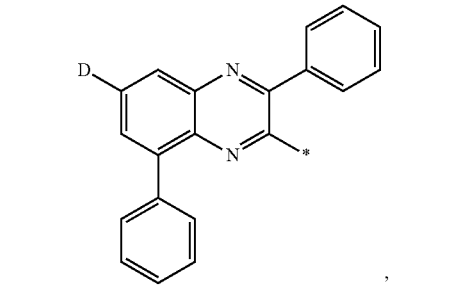
E-209
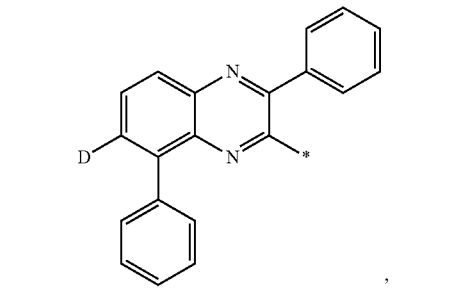

E-210 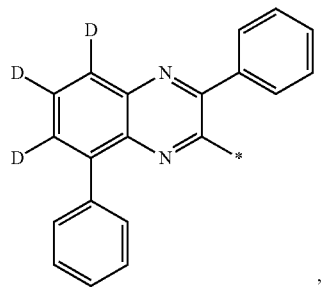,

E-211 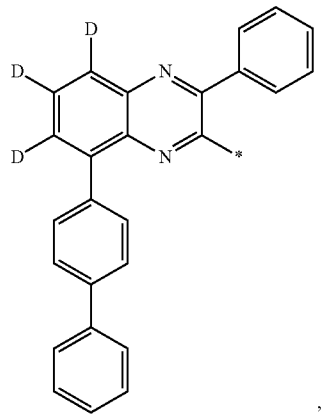,

E-212 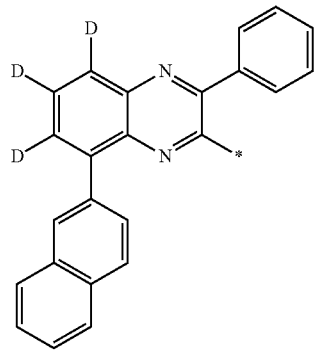,

E-213 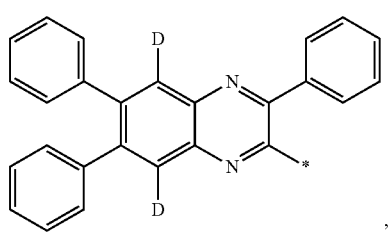,

E-214 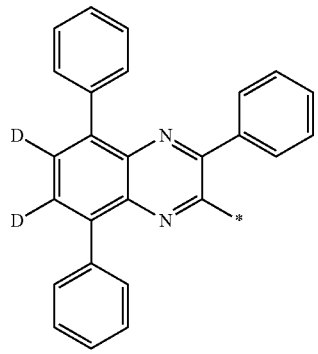,

E-215 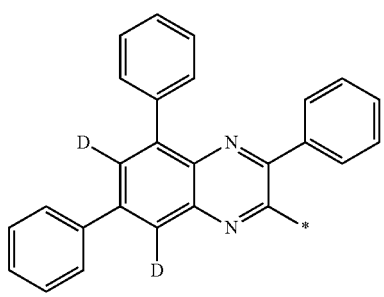, and

E-216 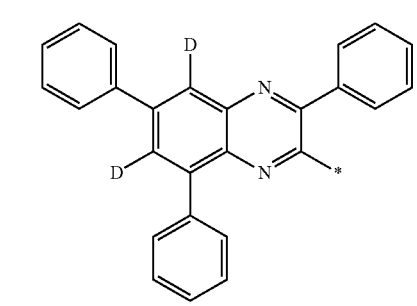.

According to an embodiment of the present disclosure, wherein hydrogens in the above structures E-1 to E-216 may be partially or fully substituted by deuterium.

According to an embodiment of the present disclosure, wherein the L is selected from the group consisting of: a single bond, phenylene, naphthylene, biphenylene, terphenylene, triphenylenylene, dibenzofuranylene, dibenzothiophenylene, pyridylene, thienylene, and combinations thereof.

According to an embodiment of the present disclosure, wherein the L is selected from the group consisting of the following structures:

a single bond, L-0

L-1
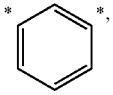,

L-2
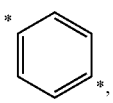,

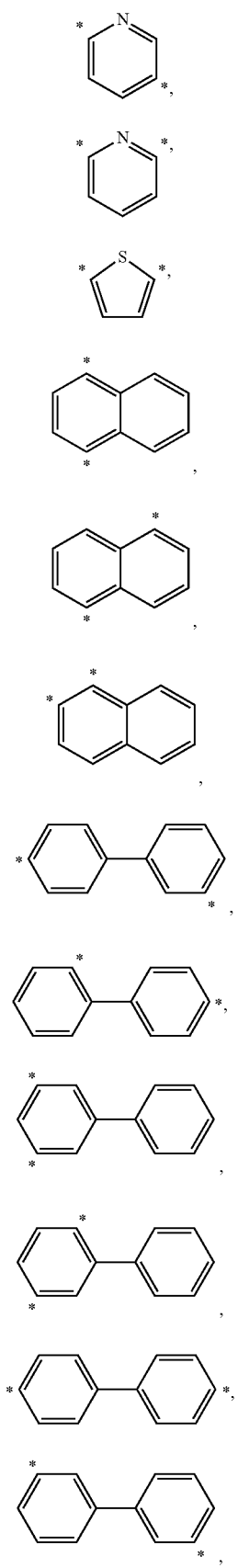
L-3
L-4
L-5
L-6
L-7
L-8
L-9
L-10
L-11
L-12
L-13
L-14
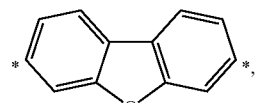
L-15
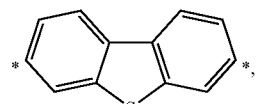
L-16
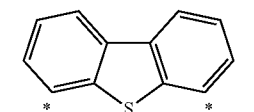
L-17
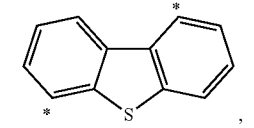
L-18
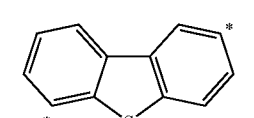
L-19
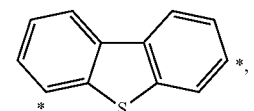
L-20
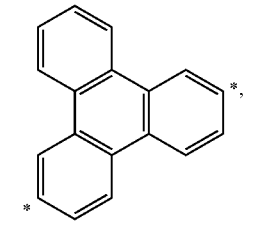
L-21
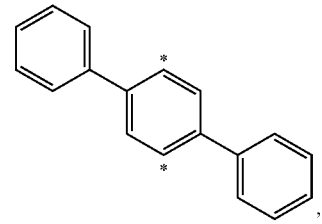
L-22
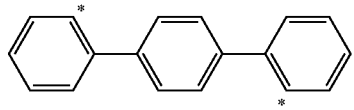
L-23
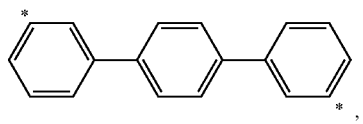
L-24

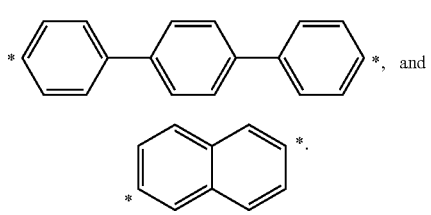

According to an embodiment of the present disclosure, wherein hydrogens in the above structures L-1 to L-26 may be partially or fully substituted by deuterium.

According to an embodiment of the present disclosure, wherein the compound having a structure of H-L-E is selected from the group consisting of Compound 1 to Compound 1116. For specific structures of Compound 1 to Compound 1116, reference is made to claim 12.

According to an embodiment of the present disclosure, wherein hydrogens in Compound 1 to Compound 1116 may be partially or fully substituted by deuterium.

According to an embodiment of the present disclosure, further disclosed is an electroluminescent device, comprising:
 an anode,
 a cathode, and
 an organic layer disposed between the anode and the cathode, wherein the organic layer includes a compound having a structure of H-L-E;
wherein H has a structure represented by Formula 1:

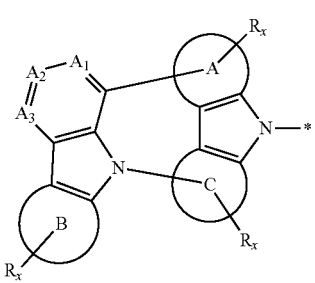

Formula 1 wherein in Formula 1, $A_1$, $A_2$, and $A_3$ are, at each occurrence identically or differently, selected from N or CR, and ring A, ring B, and ring C are, at each occurrence identically or differently, selected from a carbon ring having 5 to 18 carbon atoms or a heterocyclic ring having 3 to 18 carbon atoms;

$R_x$ represents, at each occurrence identically or differently, mono-substitution, multiple substitutions or non-substitution;

wherein E has a structure represented by Formula 2:

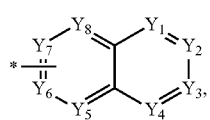

Formula 2 wherein $Y_1$ to $Y_4$ are, at each occurrence identically or differently, selected from N, $CR_y$ or $CR_z$, any two of $Y_5$ to $Y_8$ are selected from N, the other two of $Y_5$ to $Y_8$ are respectively selected from C or $CR_y$, and at least one of $Y_1$ to $Y_4$ is selected from $CR_z$;

L is selected from a single bond, substituted or unsubstituted arylene having 6 to 30 carbon atoms, substituted or unsubstituted heteroarylene having 3 to 30 carbon atoms, and combinations thereof;

wherein R, $R_x$, and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

wherein $R_z$ is, at each occurrence identically or differently, selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof, wherein adjacent substituents R, $R_x$ can be optionally joined to form a ring;

wherein adjacent substituents $R_y$ can be optionally joined to form a ring.

According to an embodiment of the present disclosure, in the device, the organic layer is an emissive layer, and the compound is a host material.

According to an embodiment of the present disclosure, in the device, the emissive layer further includes at least one phosphorescent material.

According to an embodiment of the present disclosure, in the device, the phosphorescent material is a metal complex including at least one ligand, wherein the ligand includes any one of the following structures:

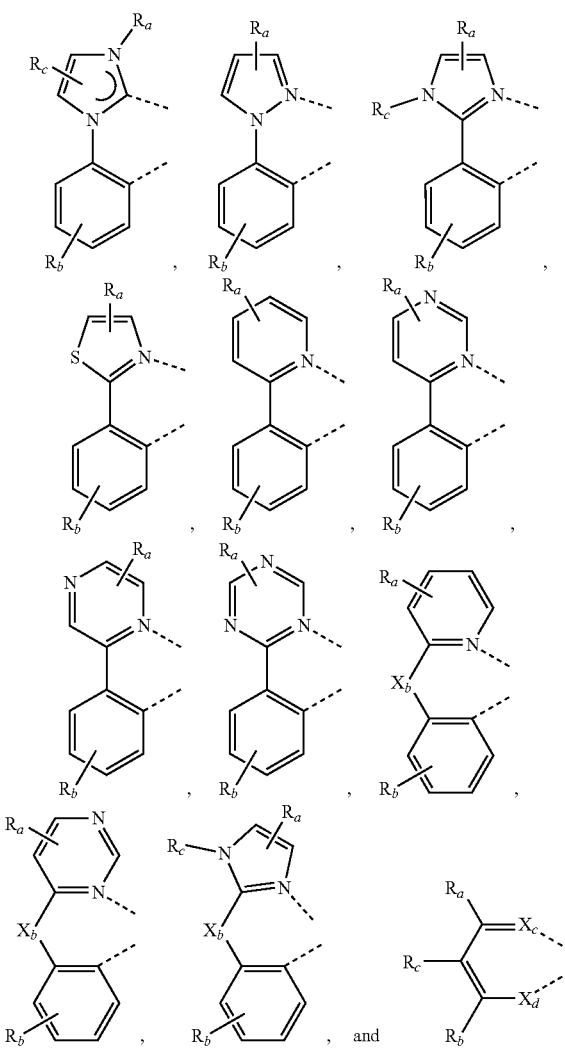

wherein,

R$_a$, R$_b$, and R$_c$, at each occurrence identically or differently, represent mono-substitution, multiple substitutions or non-substitution;

X$_b$ is, at each occurrence identically or differently, selected from the group consisting of: O, S, Se, NR$_{N1}$, and CR$_{C1}$R$_{C2}$;

X$_c$ and X$_d$ are, at each occurrence identically or differently, selected from the group consisting of: O, S, Se, and NR$_{N2}$;

R$_a$, R$_b$, R$_c$, R$_{N1}$, R$_{N2}$, R$_{C1}$, and R$_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

in the structure of the ligand, adjacent substituents can be optionally joined to form a ring.

In this embodiment, the expression that adjacent substituents can be optionally joined to form a ring is intended to mean that for groups of adjacent substituents, for example, two substituents R$_a$, two substituents R$_b$, two substituents R$_c$, substituents R$_a$ and R$_b$, substituents R$_a$ and R$_c$, substituents R$_b$ and R$_c$, substituents R$_a$ and R$_{N1}$, substituents R$_b$ and R$_{N1}$, substituents R$_a$ and R$_{C1}$, substituents R$_a$ and R$_{C2}$, substituents R$_b$ and R$_{C1}$, substituents R$_b$ and R$_{C2}$, substituents R$_a$ and R$_{N2}$, substituents R$_b$ and R$_{N2}$, and substituents R$_{C1}$ and R$_{C2}$, any one or more groups of these groups of substituents may be joined to form a ring. Obviously, these substituents may not be joined to form a ring.

According to an embodiment of the present disclosure, in the device, the phosphorescent material is a metal complex including at least one ligand, wherein the ligand has the following structure:

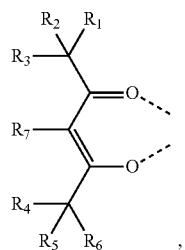

wherein R$_1$ to R$_7$ are each independently selected from the group consisting of hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

According to an embodiment of the present disclosure, in the device, the phosphorescent material is a metal complex including at least one ligand, wherein the ligand has the following structure:

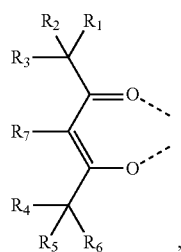

wherein at least one of $R_1$ to $R_3$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof; and/or at least one of $R_4$ to $R_6$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

According to an embodiment of the present disclosure, in the device, the phosphorescent material is a metal complex including at least one ligand, wherein the ligand has the following structure:

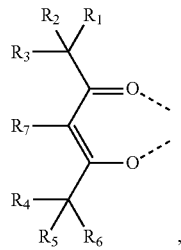

wherein at least two of $R_1$ to $R_3$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof; and/or at least two of $R_4$ to $R_6$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

According to an embodiment of the present disclosure, in the device, the phosphorescent material is a metal complex including at least one ligand, wherein the ligand has the following structure:

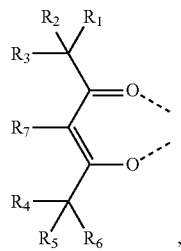

wherein at least two of $R_1$ to $R_3$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms, or combinations thereof; and/or at least two of $R_4$ to $R_6$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms, or combinations thereof.

According to an embodiment of the present disclosure, in the device, the phosphorescent material is an Ir complex, a Pt complex or an Os complex.

According to an embodiment of the present disclosure, in the device, the phosphorescent material is an Ir complex and has a structure of $Ir(L_a)(L_b)(L_c)$;

wherein $L_a$, $L_b$, and $L_c$ are, at each occurrence identically or differently, selected from any one of the group consisting of the following structures:

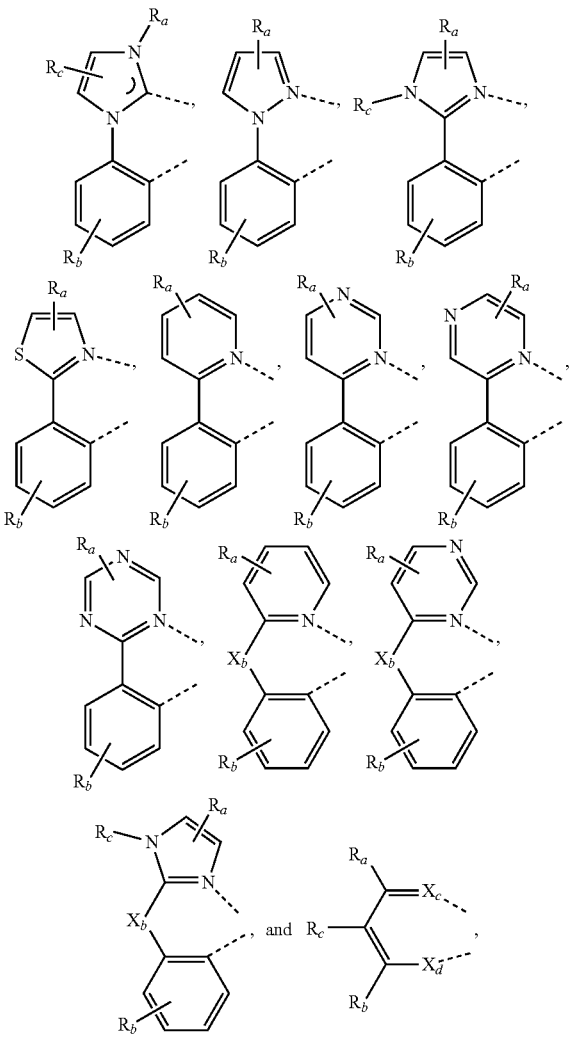

wherein
$R_a$, $R_b$, and $R_c$, at each occurrence identically or differently, represent mono-substitution, multiple substitutions or non-substitution;

$X_b$ is, at each occurrence identically or differently, selected from the group consisting of: O, S, Se, $NR_{N1}$, and $CR_{C1}R_{C2}$;

$X_c$ and $X_d$ are, at each occurrence identically or differently, selected from the group consisting of: O, S, Se, and $NR_{N2}$;

$R_a$, $R_b$, $R_c$, $R_{N1}$, $R_{N2}$, $R_{C1}$, and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;

in the structure of the ligand, adjacent substituents can be optionally joined to form a ring.

In this embodiment, the expression that adjacent substituents can be optionally joined to form a ring is intended to mean that for groups of adjacent substituents, for example, two substituents $R_a$, two substituents $R_b$, two substituents $R_c$, substituents $R_a$ and $R_b$, substituents $R_a$ and $R_c$, substituents $R_b$ and $R_c$, substituents $R_a$ and $R_{N1}$, substituents $R_b$ and $R_{N1}$, substituents $R_a$ and $R_{C1}$, substituents $R_a$ and $R_{C2}$, substituents $R_b$ and $R_{C1}$, substituents $R_b$ and $R_{C2}$, substituents $R_a$ and $R_{N2}$, substituents $R_b$ and $R_{N2}$, and substituents $R_{C1}$ and $R_{C2}$, any one or more groups of these groups of substituents may be joined to form a ring. Obviously, these substituents may not be joined to form a ring.

According to an embodiment of the present disclosure, in the device, the Ir complex is selected from the group consisting of the following structures:

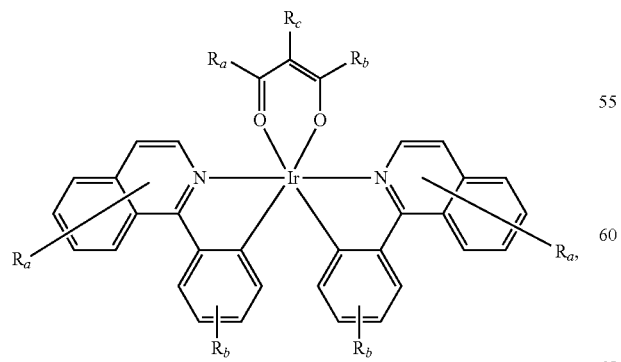

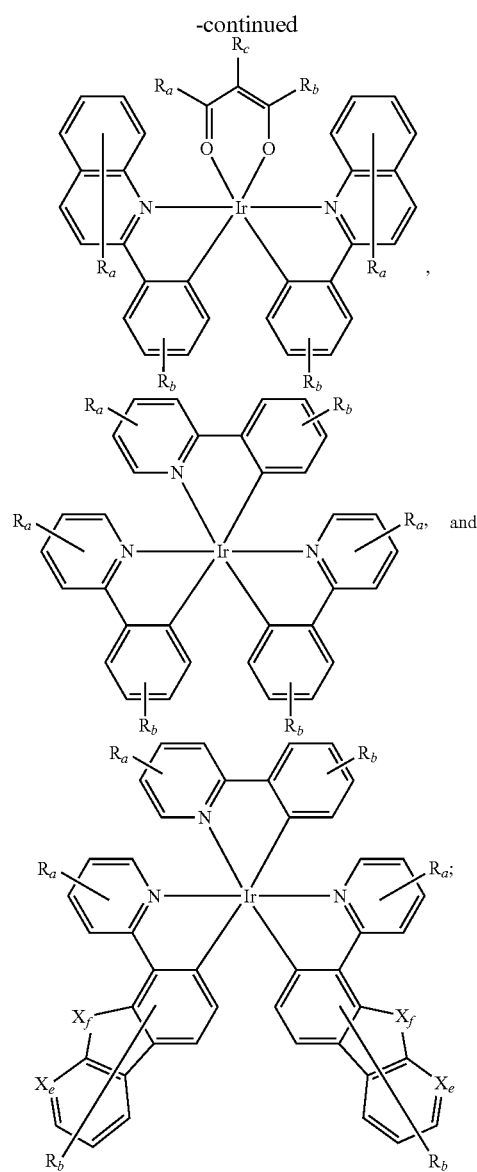

wherein $X_f$ is, at each occurrence identically or differently, selected from the group consisting of O, S, Se, $NR_{N3}$, and $CR_{C3}R_{C4}$;

wherein $X_e$ is, at each occurrence identically or differently, selected from $CR_d$ or N;

$R_a$, $R_b$, and $R_c$, at each occurrence identically or differently, represent mono-substitution, multiple substitutions or non-substitution;

$R_a$, $R_b$, $R_c$, $R_d$, $R_{N3}$, $R_{C3}$, and $R_{C4}$ are, at each occurrence identically or differently, selected from the group consisting of hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof.

According to another embodiment of the present disclosure, further disclosed is a compound formulation, comprising the compound having a structure of H-L-E. The specific structure of the compound is shown in any one of the foregoing embodiments.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, compounds disclosed herein may be used in combination with a wide variety of hosts, emissive dopants, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this present disclosure.

Material Synthesis Example

The method for preparing the compound of the present disclosure is not limited herein. Typically, the following compounds are used as examples without limitations, and synthesis routes and preparation methods thereof are described below.

Synthesis Example 1: Synthesis of Compound 1

Step 1: Synthesis of Intermediate 1

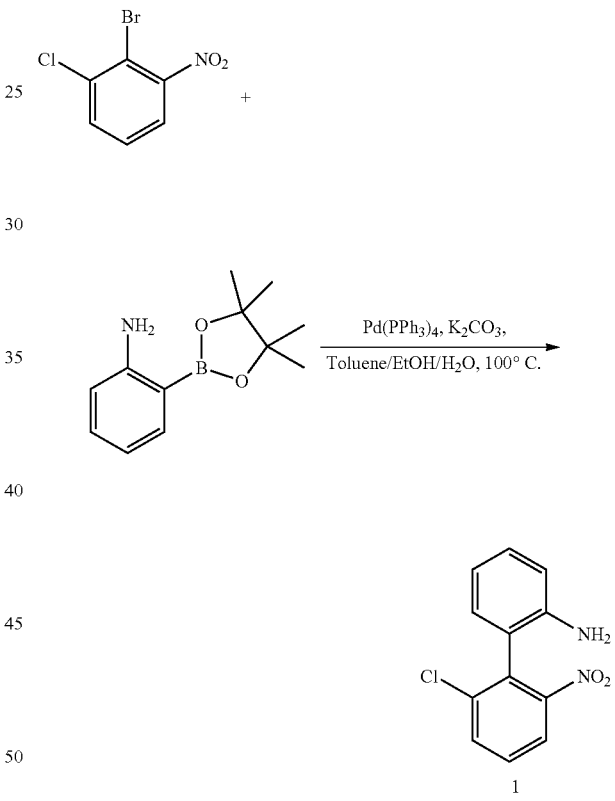

Under nitrogen protection, 2-bromo-3-chloronitrobenzene (100 g, 425.5 mmol), 2-aminophenylboronic acid pinacol ester (102 g, 468.1 mmol), tetrakis(triphenylphosphine)palladium (4.9 g, 4.25 mmol), potassium carbonate (115 g, 852 mmol), toluene (1000 mL), water (200 mL), and ethanol (200 mL) were added to a three-necked flask and reacted at 100° C. for 48 hours. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove solvents, and purified by column chromatography (PE/EA=4:1) to obtain Intermediate 1 as a yellow oil (90 g, with a yield of 85%).

Step 2: Synthesis of Intermediate 2

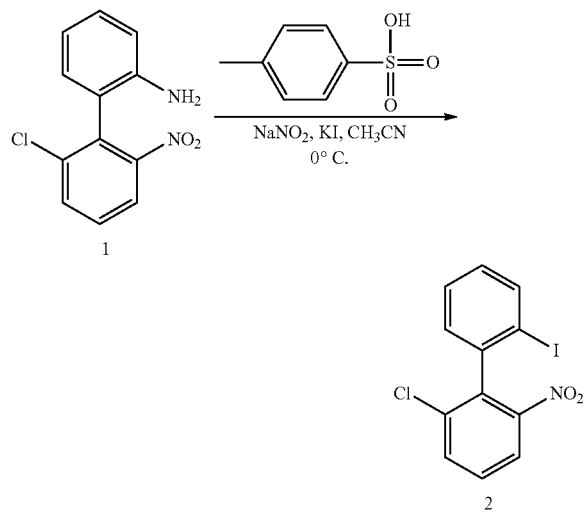

Intermediate 1 (90 g, 363 mmol) and acetonitrile (1000 mL) were separately put into a three-necked flask. p-Toluenesulfonic acid (193.2 g, 1088 mmol) was added in portions at 0° C. and stirred for 30 minutes. At this temperature, a mixed aqueous solution of sodium nitrite (69 g, 726 mmol) and potassium iodide (150.6 g, 907 mmol) was slowly added dropwise. After the dropwise addition was complete, the mixture was slowly heated to room temperature and reacted for 12 hours. After the reaction was complete, a saturated aqueous solution of sodium thiosulfate was added dropwise to quench the reaction. The reaction solution was concentrated and diluted with water. The mixed solution was extracted three times with ethyl acetate. The organic phases were dried over anhydrous sodium sulfate and concentrated to remove solvents. The mixture was isolated by column chromatography (PE/DCM=10/1) to obtain Intermediate 2 as a yellow solid (85 g, with a yield of 65%).

Step 3: Synthesis of Intermediate 4

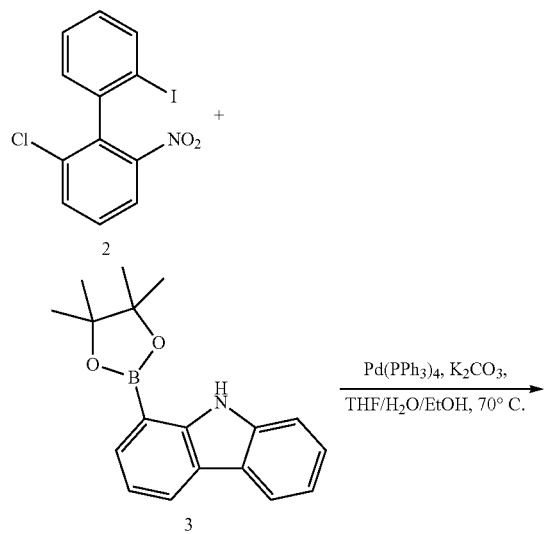

Under nitrogen protection, Intermediate 2 (20 g, 55.7 mmol), Intermediate 3 (24.5 g, 83.6 mmol), tetrakis(triphenylphosphine)palladium (1.9 g, 1.67 mmol), potassium carbonate (15.4 g, 111.4 mmol), tetrahydrofuran (500 mL), water (100 mL), and ethanol (100 mL) were added to a three-necked flask and reacted at 70° C. for 48 hours. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove solvents, and purified by column chromatography (PE/EA=4:1) to obtain Intermediate 4 as a yellow solid (12 g, with a yield of 55%).

Step 4: Synthesis of Intermediate 5

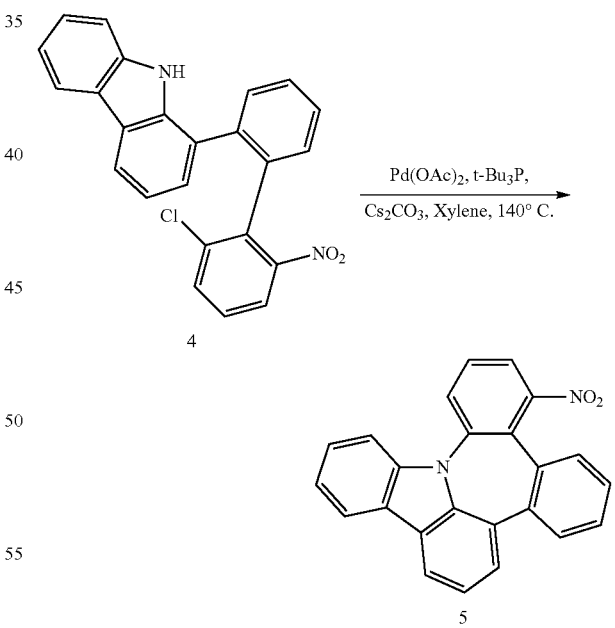

Under nitrogen protection, Intermediate 4 (12 g, 30.15 mmol), palladium acetate (338 mg, 1.5 mmol), tri-t-butylphosphine (606 mg, 3.0 mmol), cesium carbonate (20 g, 60.3 mmol), and xylene (230 mL) were added to a three-necked flask and reacted at 140° C. for 10 hours. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove solvents, and purified by column chromatography (PE/EA=6:1) to obtain Intermediate 5 as a yellow solid (9 g, with a yield of 80%).

Step 5: Synthesis of Intermediate 6

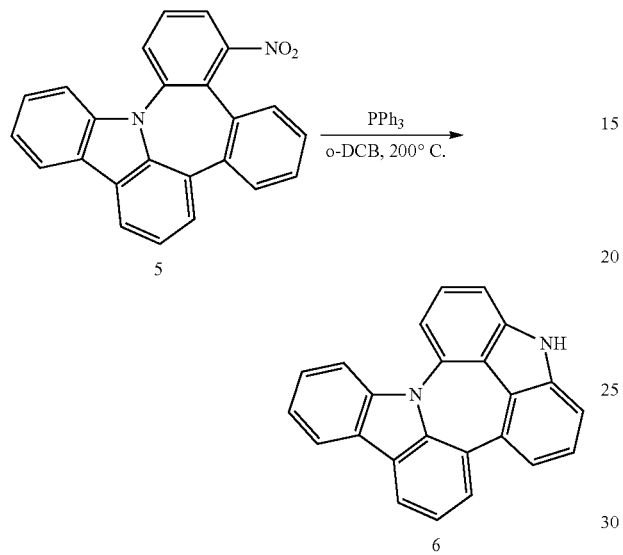

Under nitrogen protection, Intermediate 5 (9 g, 24.9 mmol), triphenylphosphine (19.6 g, 74.7 mmol) and o-dichlorobenzene (o-DCB) (100 mL) were added to a three-necked flask and reacted at 200° C. for 12 hours. After the reaction was complete, the reaction solution was concentrated to remove solvents. The crude product was isolated by column chromatography to obtain Intermediate 6 as a yellow solid (7 g, with a yield of 85%).

Step 6: Synthesis of Compound 1

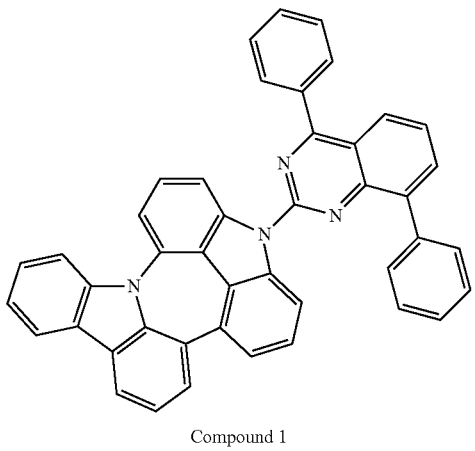

Compound 1

Under nitrogen protection, Intermediate 7 (2.8 g, 9.1 mmol), cesium carbonate (4.9 g, 15.2 mmol), and Intermediate 6 (2.5 g, 7.6 mmol) were added to a 250 mL round-bottom flask, then 50 mL of DMF was added, and the mixture was heated to 130° C. and stirred overnight. After the reaction was complete, 200 mL of distilled water was added into the reaction solution, stirred for 1 hour to precipitate solids, and filtered to obtain a crude product. The crude product was washed with distilled water, ethanol, ethyl acetate, and dichloromethane sequentially. The crude product was recrystallized from xylene/tetrahydrofuran to obtain Compound 1 as a yellow solid (2.5 g, with a yield of 45%). The product was confirmed as the target product with a molecular weight of 610.2.

Synthesis Example 2: Synthesis of Compound 2

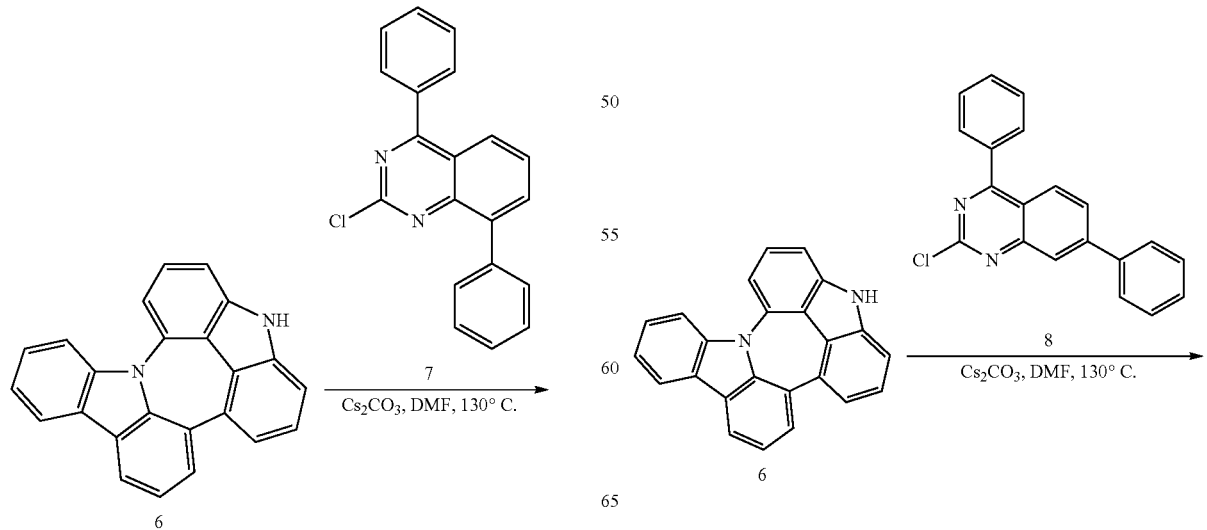

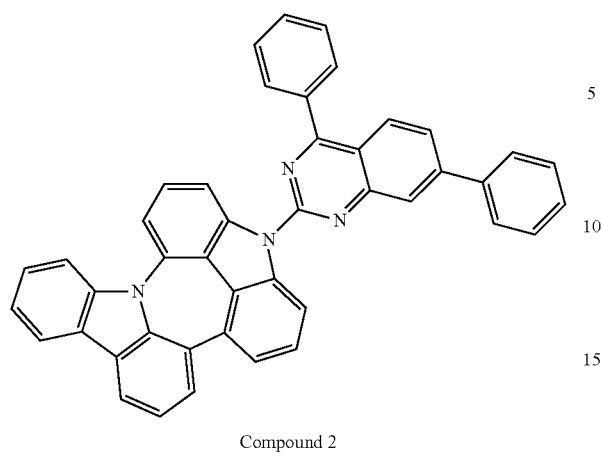

Compound 2

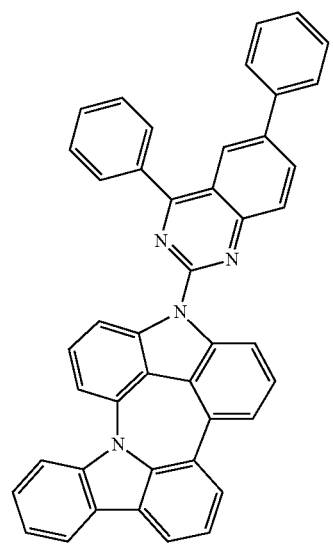

Compound 3

Under nitrogen protection, Intermediate 8 (2.8 g, 9.1 mmol), cesium carbonate (4.9 g, 15.2 mmol), and Intermediate 6 (2.5 g, 7.6 mmol) were added to a 250 mL round-bottom flask, then 50 mL of DMF was added, and the mixture was heated to 130° C. and stirred overnight. After the reaction was complete, 200 mL of distilled water was added into the reaction solution, stirred for 1 hour to precipitate solids, and filtered to obtain a crude product. The crude product was washed with distilled water, ethanol, ethyl acetate, and dichloromethane sequentially. The crude product was recrystallized from xylene/tetrahydrofuran to obtain Compound 2 as a yellow solid (2.5 g, with a yield of 45%). The product was confirmed as the target product with a molecular weight of 610.2.

Synthesis Example 3: Synthesis of Compound 3

Under nitrogen protection, Intermediate 6 (1.6 g, 4.8 mmol), Intermediate 9 (1.5 g, 4.8 mmol), DMAP (576 mg, 4.8 mmol), cesium carbonate (3.1 g, 9.6 mmol), and DMF (50 mL) were added to a three-necked flask and reacted at 80° C. for 16 hours. After the reaction was complete, the reaction solution was cooled to room temperature, added with distilled water, and filtered to obtain a crude product. The crude product was recrystallized from xylene to obtain Compound 3 as a yellow solid (2.4 g, with a yield of 83%). The product was confirmed as the target product with a molecular weight of 610.2.

Synthesis Example 4: Synthesis of Compound 57

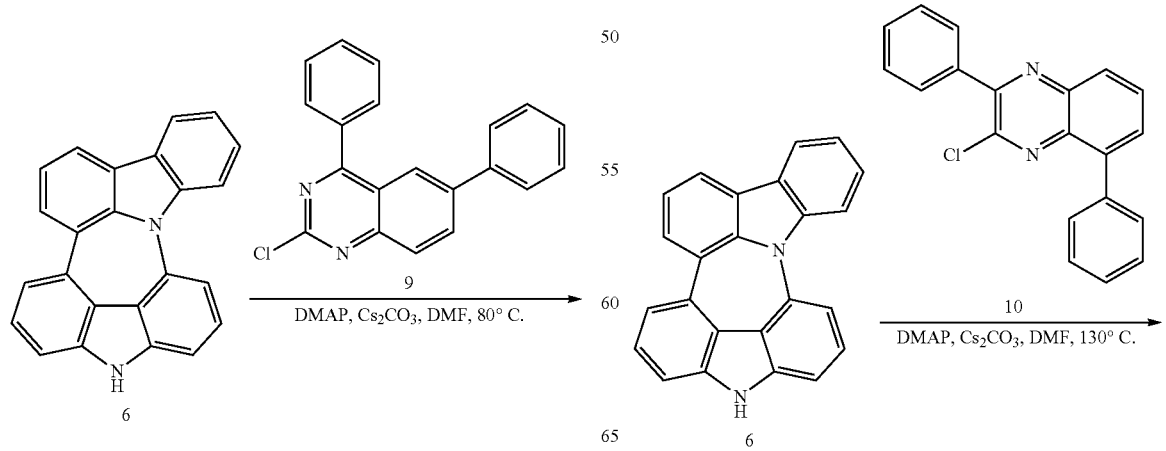

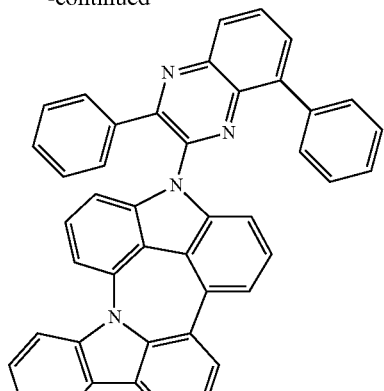

Compound 57

Under nitrogen protection, Intermediate 6 (3 g, 9.1 mmol), Intermediate 10 (3.17 g, 10 mmol), DMAP (1.1 g, 9.1 mmol), and cesium carbonate (4.9 g, 15.2 mmol) were added to a three-necked flask, and then 100 mL of DMF was added. The mixture was reacted at 130° C. for 12 hours. After the reaction was complete, the reaction solution was cooled to room temperature, added with distilled water, and filtered to obtain solids. The solids were purified by column chromatography (PE/DCM=2:1) and recrystallized from n-hexane to obtain Compound 57 as a yellow solid (3.5 g, with a yield of 63%). The product was confirmed as the target product with a molecular weight of 610.2.

Synthesis Example 5: Synthesis of Compound 58

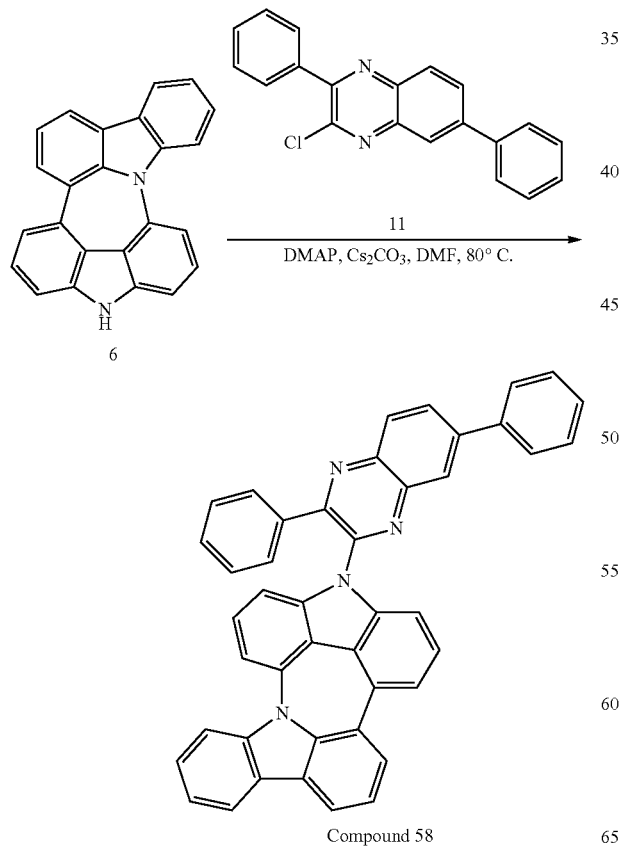

Compound 58

Under nitrogen protection, Intermediate 6 (3 g, 9.1 mmol), Intermediate 11 (3.17 g, 10 mmol), DMAP (1.1 g, 9.1 mmol), and cesium carbonate (4.9 g, 15.2 mmol) were added to a three-necked flask, and then 100 mL of DMF was added. The mixture was reacted at 80° C. for 12 hours. After the reaction was complete, the reaction solution was cooled to room temperature, added with distilled water, and filtered to obtain solids. The solids were purified by column chromatography (PE/EA=20:1) to obtain Compound 58 as a yellow solid (2 g, with a yield of 36.2%). The product was confirmed as the target product with a molecular weight of 610.2.

Synthesis Example 6: Synthesis of Compound 59

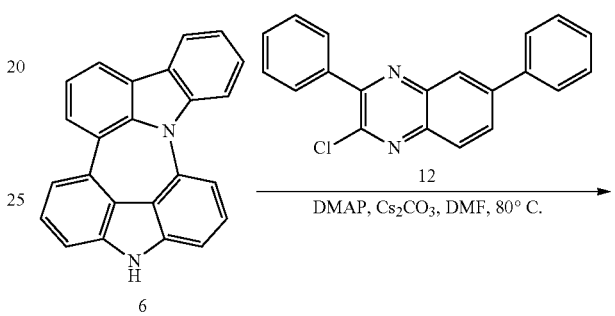

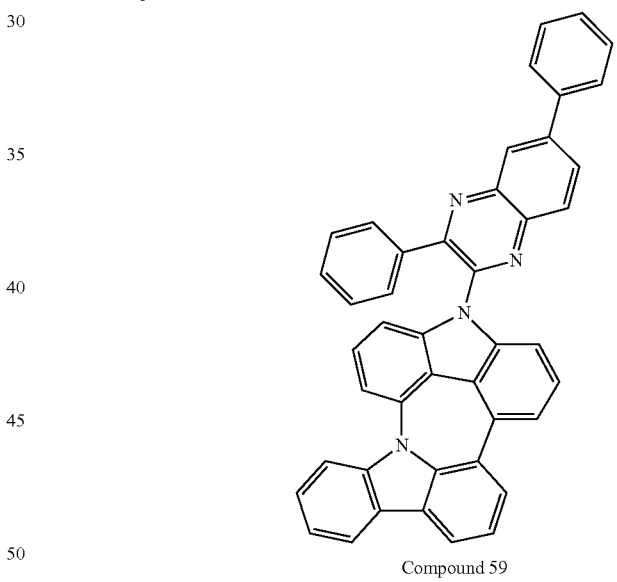

Compound 59

Under nitrogen protection, Intermediate 6 (3 g, 9.1 mmol), Intermediate 12 (3.17 g, 10 mmol), DMAP (1.1 g, 9.1 mmol), and cesium carbonate (4.9 g, 15.2 mmol) were added to a three-necked flask, and then 100 mL of DMF was added. The mixture was reacted at 80° C. for 12 hours. After the reaction was complete, the reaction solution was cooled to room temperature, added with distilled water, and filtered to obtain solids. The solids were purified by column chromatography (PE/EA=20:1) to obtain Compound 59 as a yellow solid (1.0 g, with a yield of 18.12%). The product was confirmed as the target product with a molecular weight of 610.2.

Synthesis Example 7: Synthesis of Compound 60

Synthesis Example 8: Synthesis of Compound 188

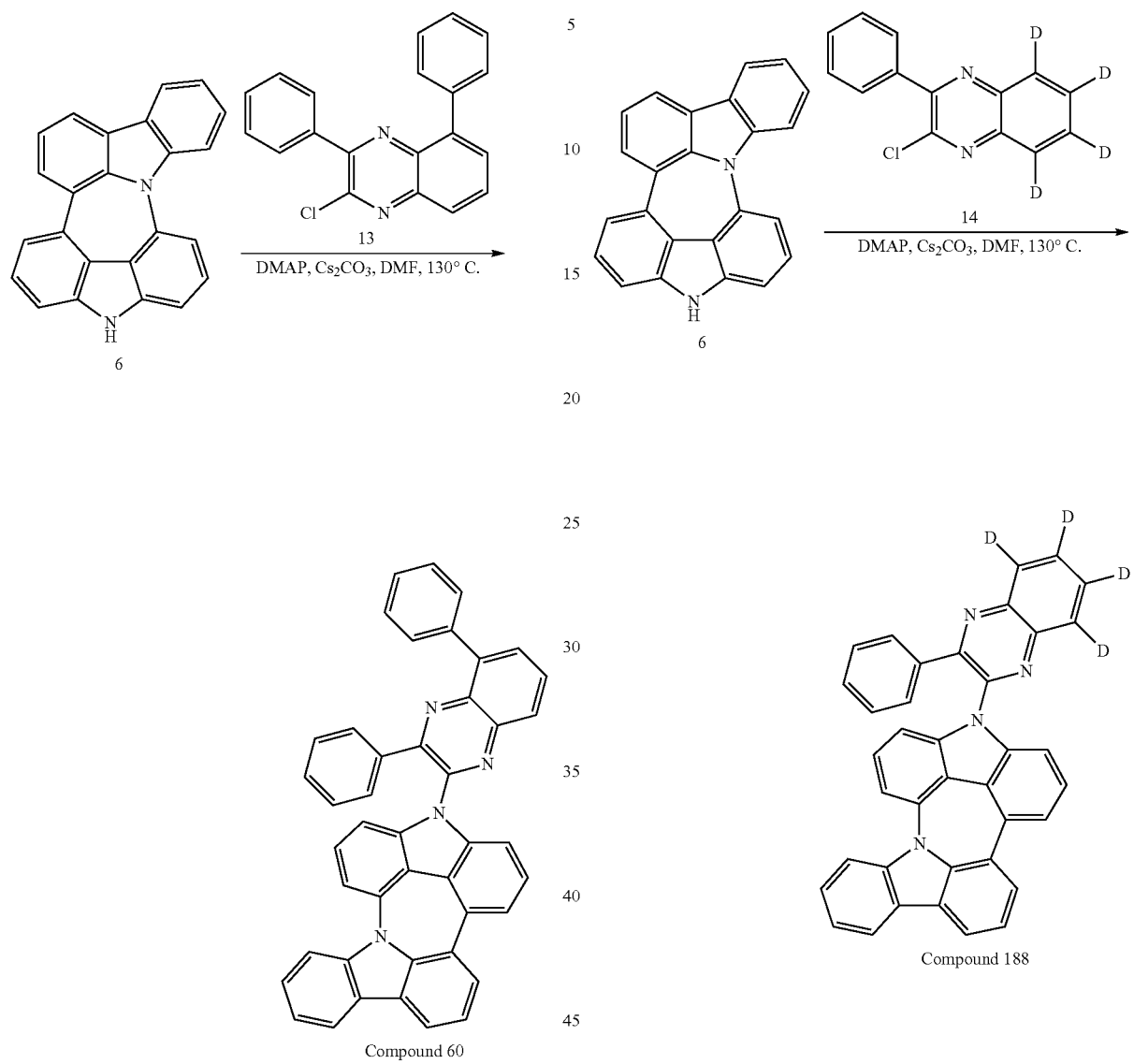

Compound 60

Compound 188

Under nitrogen protection, Intermediate 6 (3 g, 9.1 mmol), Intermediate 13 (3.17 g, 10 mmol), DMAP (1.1 g, 9.1 mmol), and cesium carbonate (4.9 g, 15.2 mmol) were added to a three-necked flask, and then 100 mL of DMF was added. The mixture was reacted at 130° C. for 12 hours. After the reaction was complete, the reaction solution was cooled to room temperature, added with distilled water, and filtered to obtain solids. The solids were purified by column chromatography (PE/DCM=2:1) and recrystallized from n-hexane to obtain Compound 60 as a yellow solid (2.15 g, with a yield of 38%). The product was confirmed as the target product with a molecular weight of 610.2.

Under nitrogen protection, Intermediate 6 (3 g, 9.1 mmol), Intermediate 14 (2.44 g, 10 mmol), DMAP (1.1 g, 9.1 mmol), and cesium carbonate (4.9 g, 15.2 mmol) were added to a three-necked flask, and then 100 mL of DMF was added. The mixture was reacted at 130° C. for 12 hours. After the reaction was complete, the reaction solution was cooled to room temperature, added with distilled water, and filtered to obtain solids. The solids were purified by column chromatography (PE/DCM=2:1) and recrystallized from n-hexane to obtain Compound 188 as a yellow solid (3.80 g, with a yield of 71.4%). The product was confirmed as the target product with a molecular weight of 538.2.

Those skilled in the art will appreciate that the above preparation method is merely illustrative. Those skilled in the art can obtain other compound structures of the present disclosure through the modifications of the preparation method.

Device Example

Device Example 1

First, a glass substrate having an Indium Tin Oxide (ITO) anode having a thickness of 120 nm was cleaned and then treated with UV ozone and oxygen plasma. After the treatment, the substrate was dried in a nitrogen-filled glovebox to remove moisture and then mounted on a substrate holder and placed in a vacuum chamber. Organic layers specified below were sequentially deposited through vacuum thermal evaporation on the ITO anode at a rate of 0.01 to 5 Angstroms per second (Å/s) at a vacuum degree of about $10^{-8}$ torr. Compound HI was used as a hole injection layer (HIL) with a thickness of 100 Angstroms (Å). Compound HT was used as a hole transporting layer (HTL) with a thickness of 400 Å. Compound EB was used as an electron blocking layer (EBL) with a thickness of 50 Å. Then, Compound 1 of the present disclosure as a host and Compound RD as a dopant were co-deposited as an emissive layer (EML) with a thickness of 400 Å. Compound HB was used as a hole blocking layer (HBL) with a thickness of 50 Å. On the HBL, Compound ET and 8-hydroxyquinolinolato-lithium (Liq) were co-deposited as an electron transporting layer (ETL) with a thickness of 350 Å. Finally, 8-hydroxyquinolinolato-lithium (Liq) with a thickness of 10 Å was deposited as an electron injection layer (EIL), and Al with a thickness of 1200 Å was deposited as a cathode. The device was transferred back to the glovebox and encapsulated with a glass lid to complete the device.

Device Comparative Example 1

The implementation mode in Device Comparative Example 1 was the same as that in Device Example 1, except that in the emissive layer (EML), Compound 1 of the present disclosure was replaced with Compound A as the host.

Detailed structures and thicknesses of layers of the devices are shown in the following table. The layers using more than one material were obtained by doping different compounds at weight ratios as recorded in the following table.

The structures of the materials used in the devices are shown as follows:

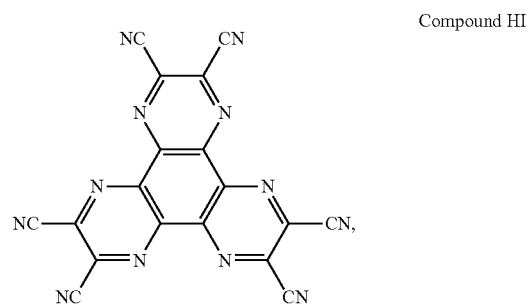

Compound HI

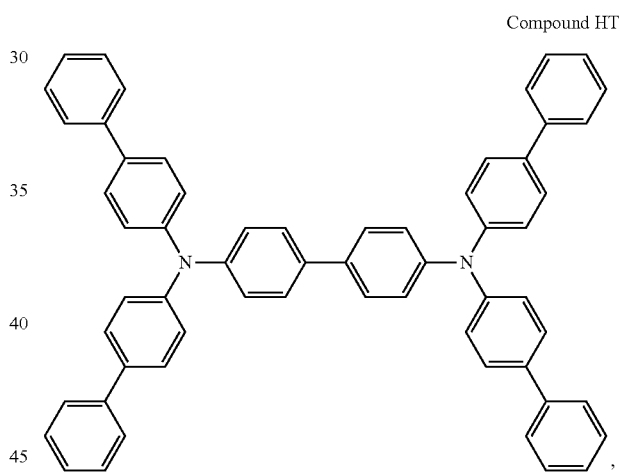

Compound HT

TABLE 1

Device structures in Device Example and Device Comparative Example

| Device ID | HIL | HTL | EBL | EML (400 Å) Host | EML (400 Å) Dopant | HBL | ETL |
|---|---|---|---|---|---|---|---|
| Example 1 | Compound HI (100 Å) | Compound HT (400 Å) | Compound EB (50 Å) | Compound 1 (97%) | Compound RD (3%) | Compound HB (50 Å) | Compound ET:Liq (40:60) (350 Å) |
| Comparative Example 1 | Compound HI (100 Å) | Compound HT (400 Å) | Compound EB (50 Å) | Compound A (97%) | Compound RD (3%) | Compound HB (50 Å) | Compound ET:Liq (40:60) (350 Å) |

-continued
Compound EB
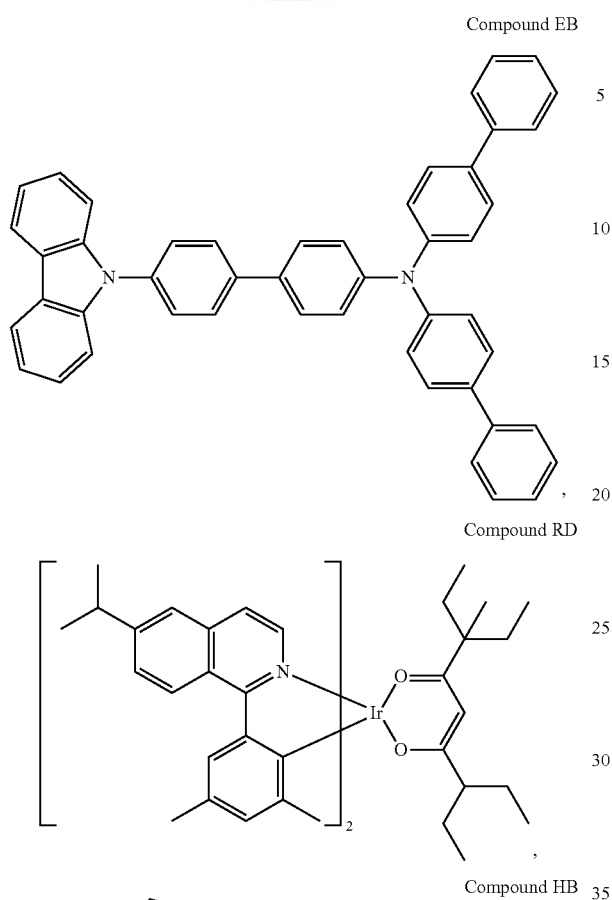
Compound RD
Compound HB
Compound ET
-continued
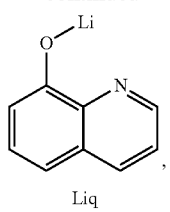
Liq
Compound A
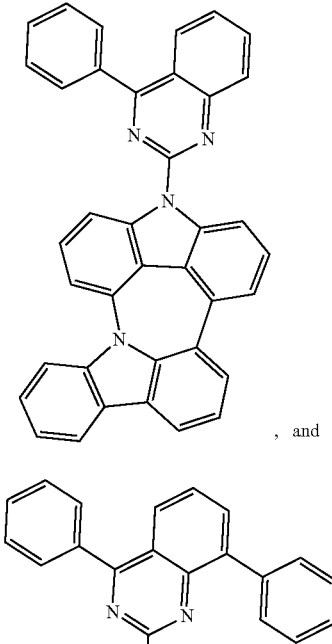
, and
Compound 1
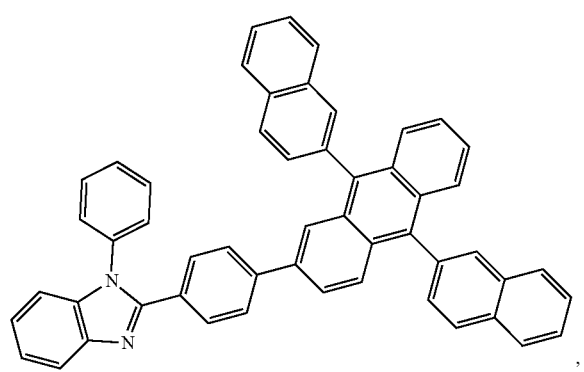
.
Table 2 lists the maximum wavelength ($\lambda_{max}$), driving voltage (V), and power efficiency (PE, lm/W) measured at the constant current of 15 mA/cm².
TABLE 2
| | Device data | | |
|---|---|---|---|
| | At 15 mA/cm² | | |
| Device ID | $\lambda_{max}$ [nm] | Voltage [V] | PE [lm/W] |
| Example 1 | 627 | 4.0 | 14 |
| Comparative Example 1 | 627 | 4.0 | 12 |

As shown in Table 2, the power efficiency (14 lm/W) of Example 1 measured at the constant current was improved by 16.7% compared with the power efficiency (12 lm/W) of Comparative Example 1. The compound in the present disclosure has a hole transporting unit formed of an indole- and pyrrole-fused azamacrocycle which is bonded to an electron transporting unit formed of substituted quinazoline or a derived structure thereof. Compared with the host compound used in Comparative Example, the compound of the present disclosure further introduces a substitution on the specific ring of the electron transporting unit, which allows the hole transport and electron transport in the emissive layer to reach a more balanced state. The light-emitting device made of the compound of the present disclosure can greatly improve the light-emitting efficiency.

Device Example 2

The implementation mode in Device Example 2 was the same as that in Device Example 1, except that in the emissive layer (EML), Compound 1 of the present disclosure was replaced with Compound 58 of the present disclosure as the host, and Compound 58 was co-deposited with Compound RD (at a weight ratio of 98:2).

Device Example 3

The implementation mode in Device Example 3 was the same as that in Device Example 1, except that in the emissive layer (EML), Compound 1 of the present disclosure was replaced with Compound 59 of the present disclosure as the host, and Compound 59 was co-deposited with Compound RD (at a weight ratio of 98:2).

Device Example 4

The implementation mode in Device Example 4 was the same as that in Device Example 1, except that in the emissive layer (EML), Compound 1 of the present disclosure was replaced with Compound 60 of the present disclosure as the host, and Compound 60 was co-deposited with Compound RD (at a weight ratio of 98:2).

Device Example 5

The implementation mode in Device Example 5 was the same as that in Device Example 1, except that in the emissive layer (EML), Compound 1 of the present disclosure was replaced with Compound 188 of the present disclosure as the host, and Compound 188 was co-deposited with Compound RD (at a weight ratio of 98:2).

Device Comparative Example 2

The implementation mode in Device Comparative Example 2 was the same as that in Device Example 1, except that in the emissive layer (EML), Compound 1 of the present disclosure was replaced with Compound B as the host, and Compound B was co-deposited with Compound RD (at a weight ratio of 98:2).

Detailed structures and thicknesses of layers of the devices are shown in the following table. The layers using more than one material were obtained by doping different compounds at weight ratios as recorded in the following table.

TABLE 3

Device structures in Device Examples and Device Comparative Example

| Device ID | HIL | HTL | EBL | EML (400 Å) Host | Dopant | HBL | ETL |
|---|---|---|---|---|---|---|---|
| Example 2 | Compound HI (100 Å) | Compound HT (400 Å) | Compound EB (50 Å) | Compound 58 (98%) | Compound RD (2%) | Compound HB (50 Å) | Compound ET:Liq (40:60) (350 Å) |
| Example 3 | Compound HI (100 Å) | Compound HT (400 Å) | Compound EB (50 Å) | Compound 59 (98%) | Compound RD (2%) | Compound HB (50 Å) | Compound ET:Liq (40:60) (350 Å) |
| Example 4 | Compound HI (100 Å) | Compound HT (400 Å) | Compound EB (50 Å) | Compound 60 (98%) | Compound RD (2%) | Compound HB (50 Å) | Compound ET:Liq (40:60) (350 Å) |
| Example 5 | Compound HI (100 Å) | Compound HT (400 Å) | Compound EB (50 Å) | Compound 188 (98%) | Compound RD (2%) | Compound HB (50 Å) | Compound ET:Liq (40:60) (350 Å) |
| Comparative Example 2 | Compound HI (100 Å) | Compound HT (400 Å) | Compound EB (50 Å) | Compound B (98%) | Compound RD (2%) | Compound HB (50 Å) | Compound ET:Liq (40:60) (350 Å) |

Structures of the new materials used in the devices are shown as follows:

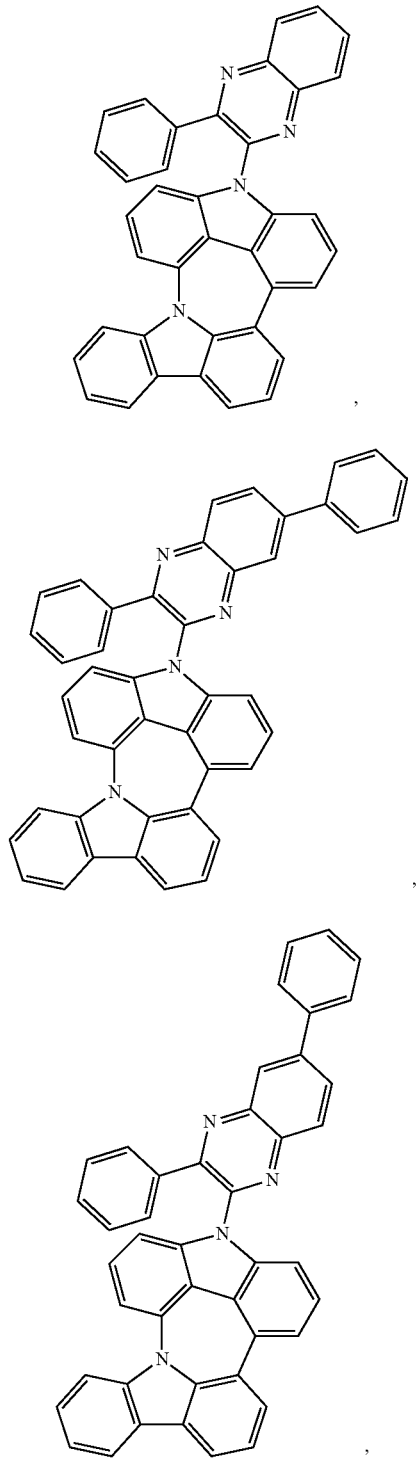

Compound B

Compound 58

Compound 59

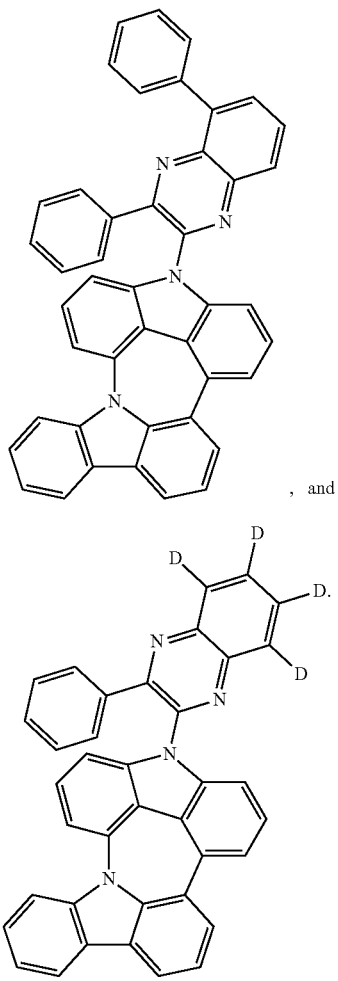

Compound 60

, and

Compound 188

Table 4 lists the maximum wavelength ($\lambda_{max}$), driving voltage (V), and power efficiency (PE, lm/W) measured under the condition of 1000 cd/m².

TABLE 4

| | Device data | | |
| --- | --- | --- | --- |
| | At 1000 cd/m² | | |
| Device ID | $\lambda_{max}$ [nm] | Voltage [V] | PE [lm/W] |
| Example 2 | 625 | 2.80 | 21 |
| Example 3 | 628 | 2.75 | 22 |
| Example 4 | 626 | 3.29 | 20 |
| Example 5 | 626 | 3.28 | 20 |
| Comparative Example 2 | 626 | 3.37 | 19 |

As shown in Table 4, the driving voltages of Examples 2 to 5 measured at a constant brightness of 1000 cd/m² were reduced by 16.9%, 18.4%, 2.4%, and 2.6%, respectively, compared with Comparative Example 2 in which the driving voltage measured was 3.37 V. The driving voltage of Comparative Example 2 was excellent compared with the same kind of materials, but the driving voltages of the compounds of Examples 2 to 5 could be further reduced, indicating that the compounds of the present disclosure had unique advantages. In terms of power efficiency, the power efficiency in Examples 2 to 5 was improved by 10%, 16%, 5%, and 5%, respectively, compared with Comparative Example 2 (19 lm/w). In terms of device lifetime (LT97), the device lifetime in Example 5 (62 h, at a constant current density of 80 mA/cm$^2$) was increased by 44% compared with Comparative Example 2 (43 h, at a constant current density of 80 mA/cm$^2$). The compound in the present disclosure has a hole transporting unit formed of an indole- and pyrrole-fused azamacrocycle which is bonded to an electron transporting unit formed of substituted quinazoline or a derived structure thereof. Compared with the host compound used in Comparative Examples, the compounds of the present disclosure further introduce substitution on the specific ring of the electron transporting unit, which strengthens the stability of electron transport and allows the hole transport and electron transport in the emissive layer to reach a more balanced state. Therefore, the light-emitting devices using the compounds of the present disclosure can significantly reduce the driving voltage and greatly improve the efficiency, and more importantly, significantly prolong the service lifetime.

In summary, the compound disclosed in the present disclosure has a hole transporting unit formed of an indole- and pyrrole-fused azamacrocycle which is bonded to an electron transporting unit formed of substituted quinazoline, quinoxaline or a similar structure thereof. The further introduction of a substitution on the specific ring of the electron transporting unit segment strengthens the stability of electron transport and allows the hole transport and electron transport in the emissive layer to reach a more balanced state. The compound, when used as the emissive layer host material in the electroluminescent device, can achieve a low driving voltage, significantly improve the device efficiency, and greatly prolong the device lifetime, which fully proves that the compounds disclosed in the present disclosure have unique properties and great application prospects.

It should be understood that various embodiments described herein are embodiments and not intended to limit the scope of the present disclosure. Therefore, it is apparent to those skilled in the art that the present disclosure as claimed may include variations of specific embodiments and preferred embodiments described herein. Many of the materials and structures described herein may be replaced with other materials and structures without departing from the spirit of the present disclosure. It should be understood that various theories as to why the present disclosure works are not intended to be limitative.

The invention claimed is:

1. A compound, having a structure of H-L-E;
   wherein H has a structure represented by Formula 1-a:

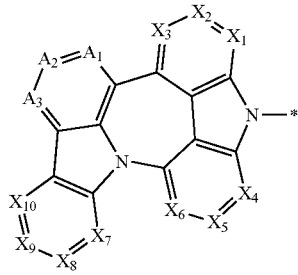

Formula 1-a wherein $A_1$ to $A_3$ are, at each occurrence identically or differently, selected from CR, and $X_1$ to $X_{10}$ are, at each occurrence identically or differently, selected from $CR_x$;

wherein E has a structure represented by Formula 2-a, or Formula 2-c:

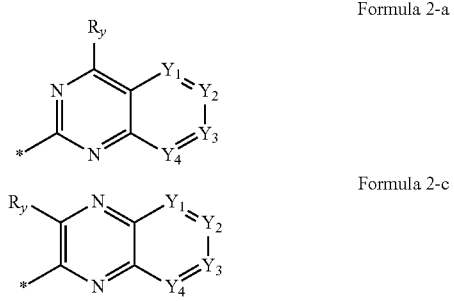

Formula 2-a

Formula 2-c wherein in Formula 2-a, $Y_1$ to $Y_3$ are, at each occurrence identically or differently, selected from $CR_y$, and $Y_4$ is selected from $CR_z$;

wherein in Formula 2-c, $Y_1$ to $Y_4$ are, at each occurrence identically or differently, selected from $CR_y$ or $CR_z$, and at least one of $Y_1$, $Y_2$ and $Y_4$ is selected from $CR_z$;

L is a single bond;

wherein R, $R_x$, and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, a cyano group, and combinations thereof;

wherein $R_z$ is, at each occurrence identically or differently, selected from substituted or unsubstituted aryl having 6 to 30 carbon atoms.

2. The compound according to claim 1, wherein the H has a structure represented by Formula 1-a:

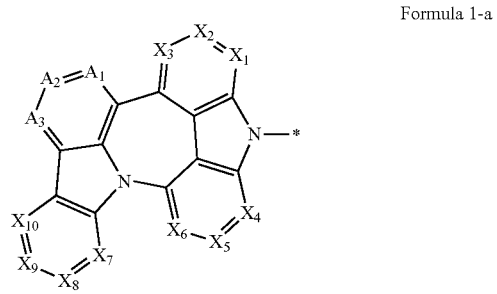

Formula 1-a wherein $A_1$ to $A_3$ are, at each occurrence identically or differently, selected from CR, and X to $X_{10}$ are, at each occurrence identically or differently, selected from $CR_x$;

wherein R and $R_x$ are, at each occurrence identically or differently, selected from the group consisting of: hydrogen, deuterium, halogen, substituted or unsubstituted aryl having 6 to 30 carbon atoms, substituted or unsubstituted heteroaryl having 3 to 30 carbon atoms, and combinations thereof.

3. The compound according to claim 2, wherein R and $R_y$ are, at each occurrence identically or differently, selected from the group consisting of: hydrogen, deuterium, substituted or unsubstituted aryl having 6 to 20 carbon atoms, substituted or unsubstituted heteroaryl having 3 to 20 carbon atoms, and combinations thereof.

4. The compound according to claim 2, wherein at least one of R and $R_x$ is selected from deuterium, substituted or unsubstituted aryl having 6 to 30 carbon atoms, or substituted or unsubstituted heteroaryl having 3 to 30 carbon atoms.

5. The compound according to claim 1, wherein the His selected from the group consisting of the following structures:

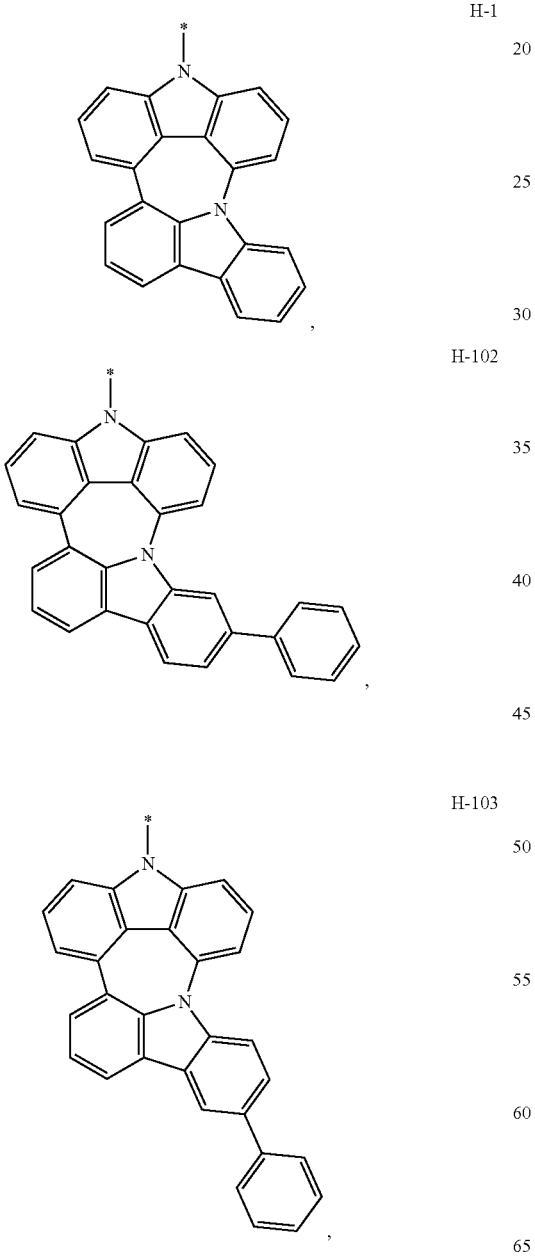

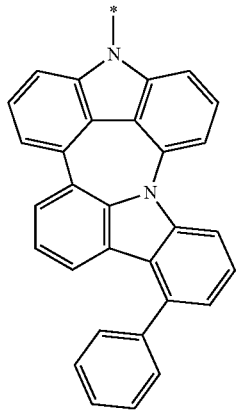

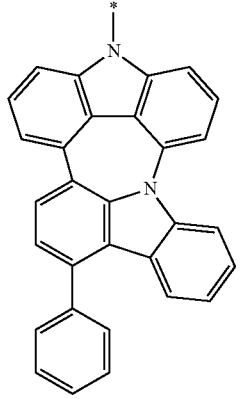

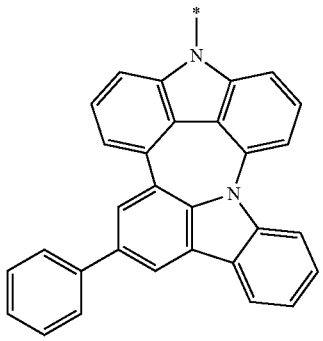

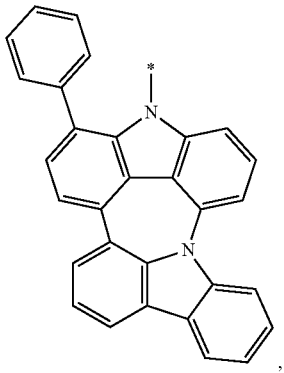

H-108
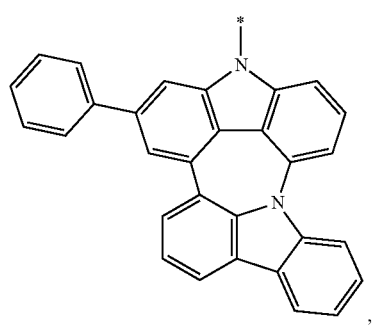
H-109
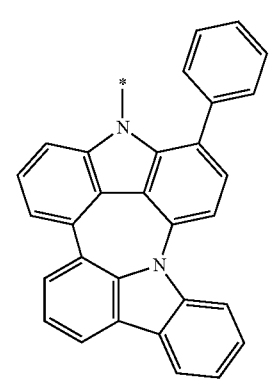
H-110
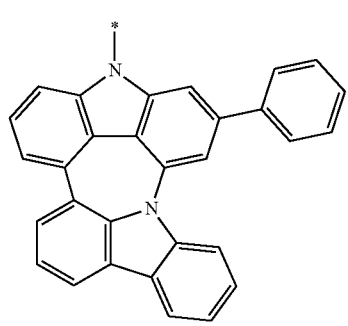
H-111
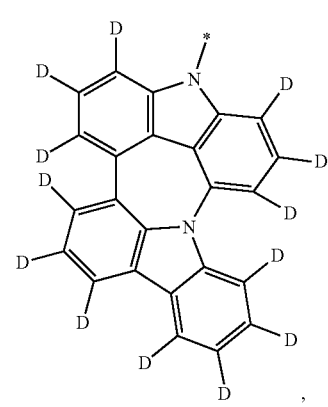
H-112
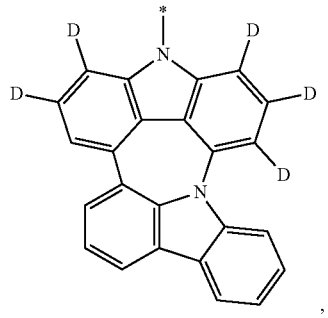
H-113
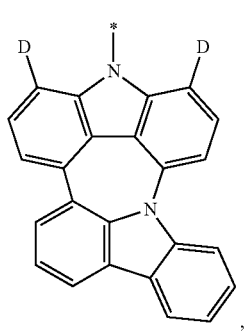
H-114
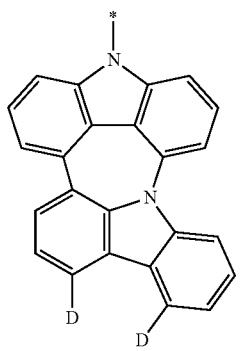
H-115
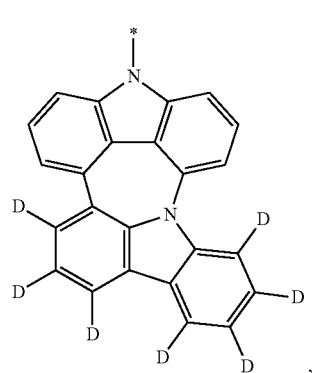

-continued

H-116

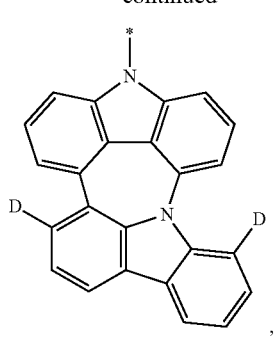
,

H-117

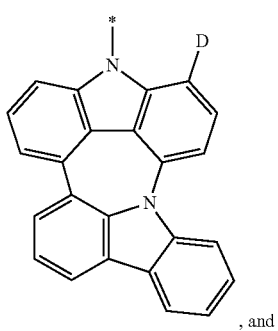
, and

H-118

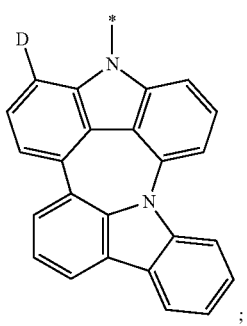
;

wherein optionally, hydrogens in the above structures can be partially or fully substituted with deuterium.

6. The compound according to claim 1, wherein the E has a structure represented by Formula 2-a or Formula 2-c:

Formula 2-a

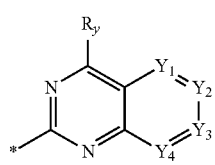

Formula 2-c

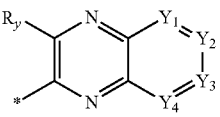

wherein in Formula 2-a, $Y_1$ to $Y_3$ are, at each occurrence identically or differently, selected from $CR_y$, and $Y_4$ is selected from $CR_z$;

wherein in Formula 2-c, $Y_1$, $Y_3$, and $Y_4$ are, at each occurrence identically or differently, selected from $CR_y$, and $Y_2$ is selected from $CR_z$;

wherein $R_y$ is, at each occurrence identically or differently, selected from the group consisting of: hydrogen, deuterium, halogen, substituted or unsubstituted aryl having 6 to 30 carbon atoms, substituted or unsubstituted heteroaryl having 3 to 30 carbon atoms, and combinations thereof;

wherein $R_z$ is, at each occurrence identically or differently, selected from substituted or unsubstituted aryl having 6 to 30 carbon atoms.

7. The compound according to claim 6, wherein in the structures represented by Formula 2-a or Formula 2-c, the $R_y$ connected to the aza six-membered ring is selected from substituted or unsubstituted aryl having 6 to 30 carbon atoms.

8. The compound according to claim 5, wherein the E is selected from the group consisting of the following structures:

E-1

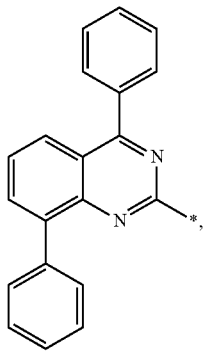

E-5

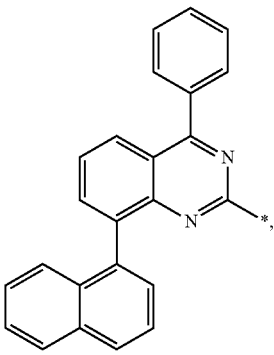

E-9

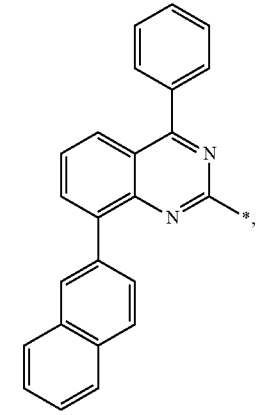

-continued
E-13
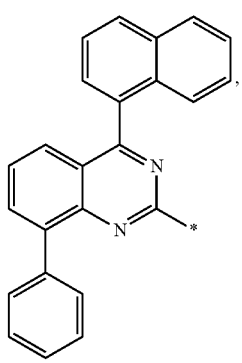
E-17
E-21
E-25
-continued
E-29
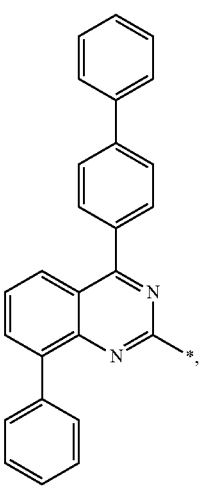
E-33
E-37
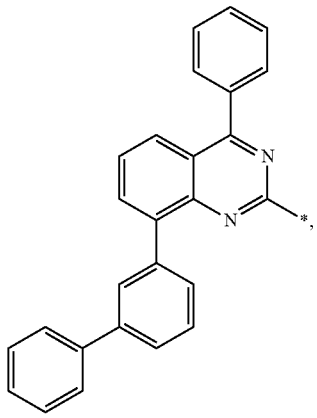

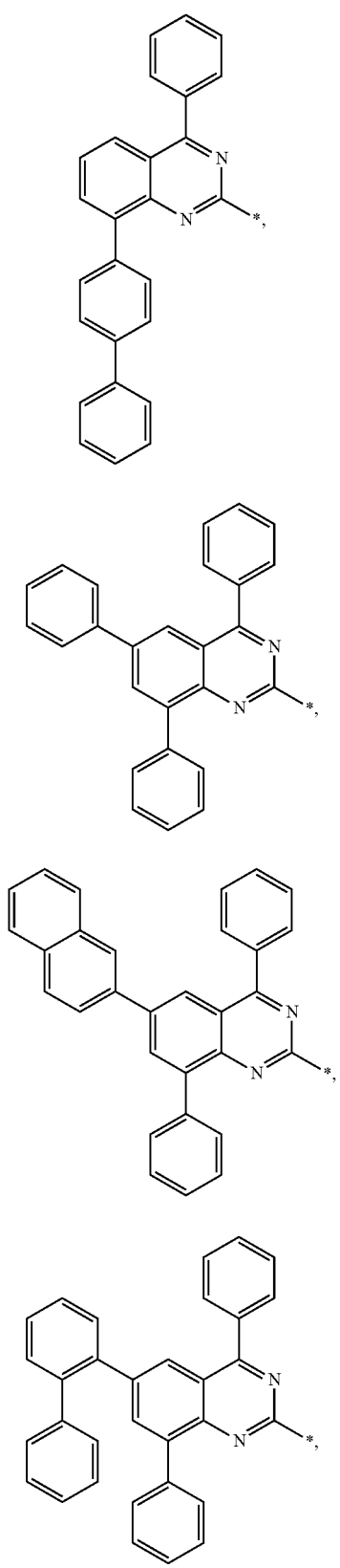
E-41
E-45
E-47
E-49
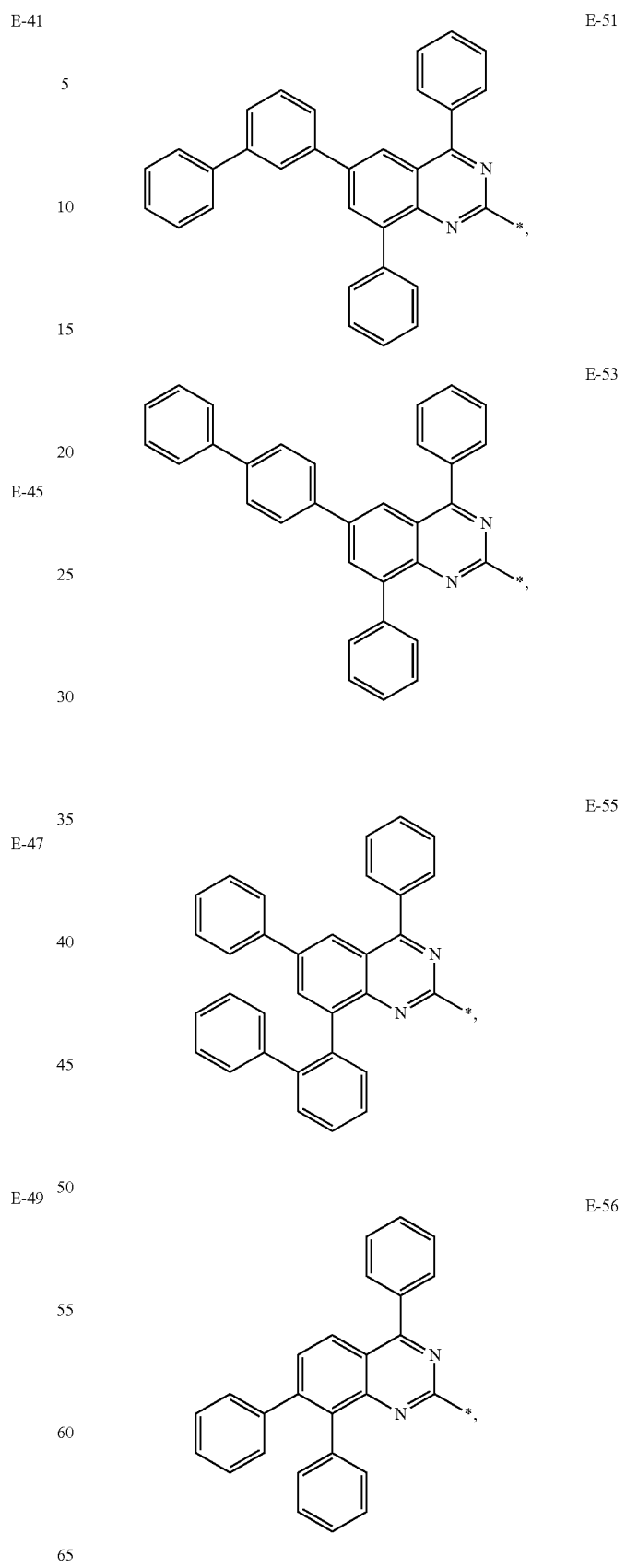
E-51
E-53
E-55
E-56

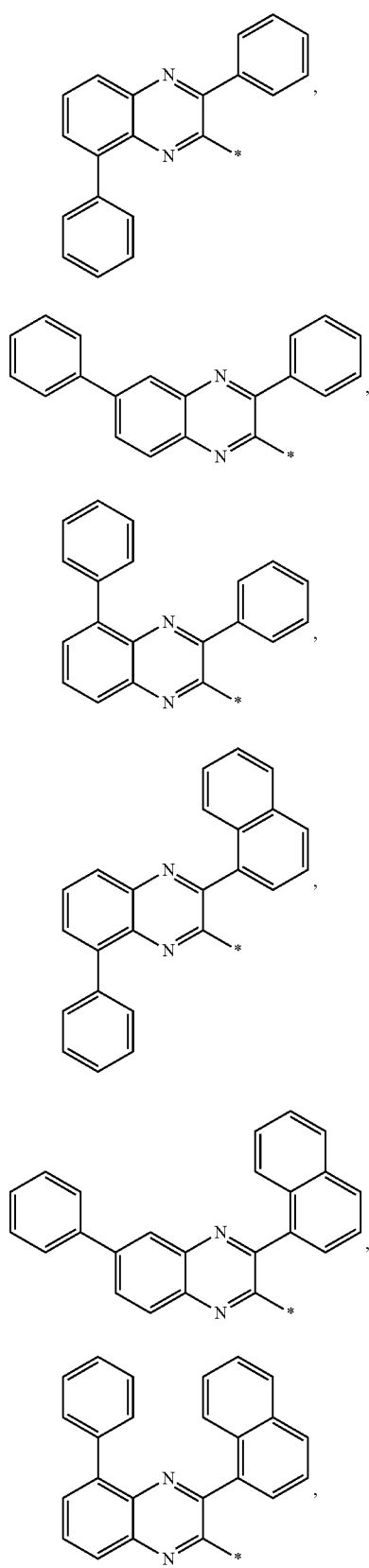
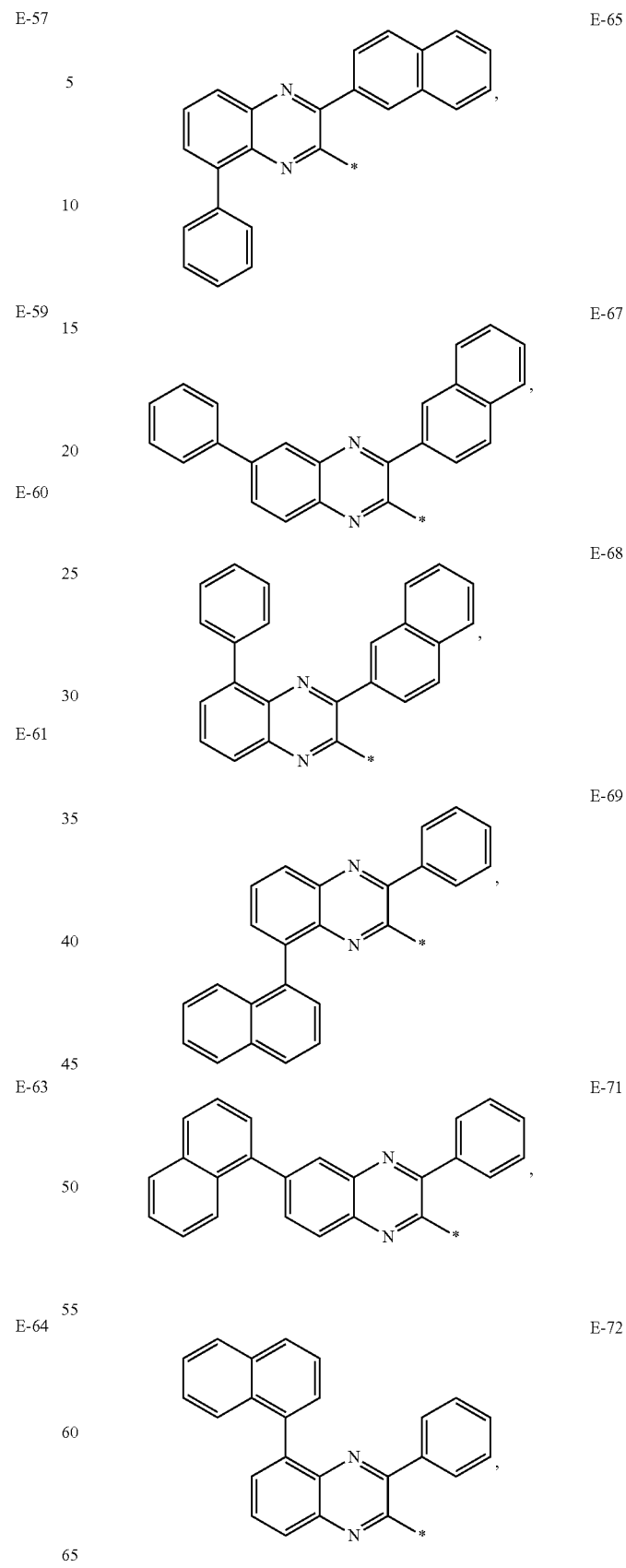

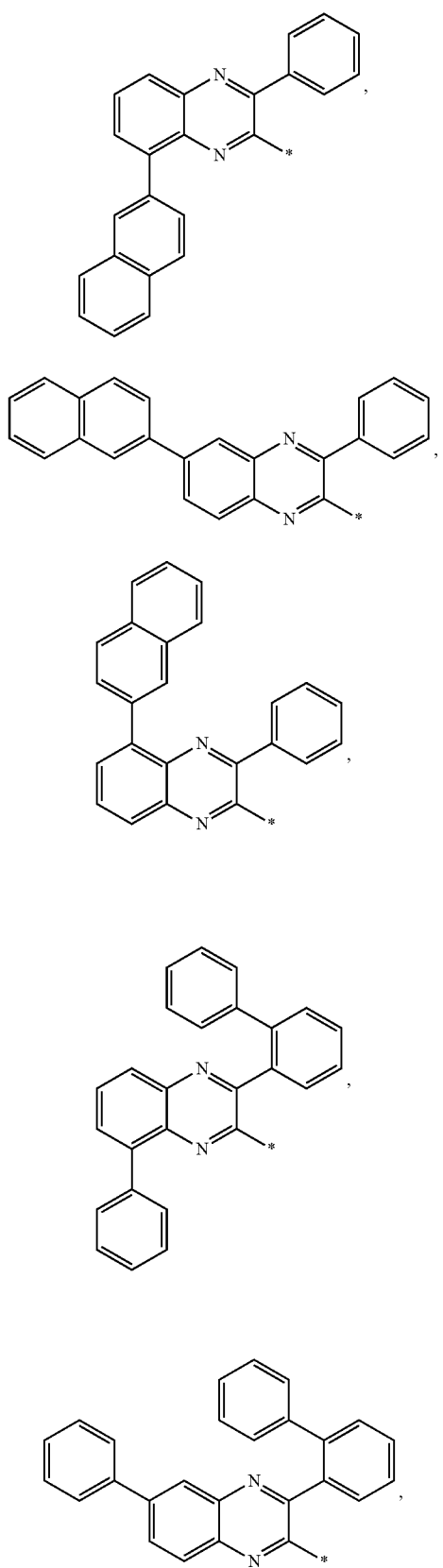
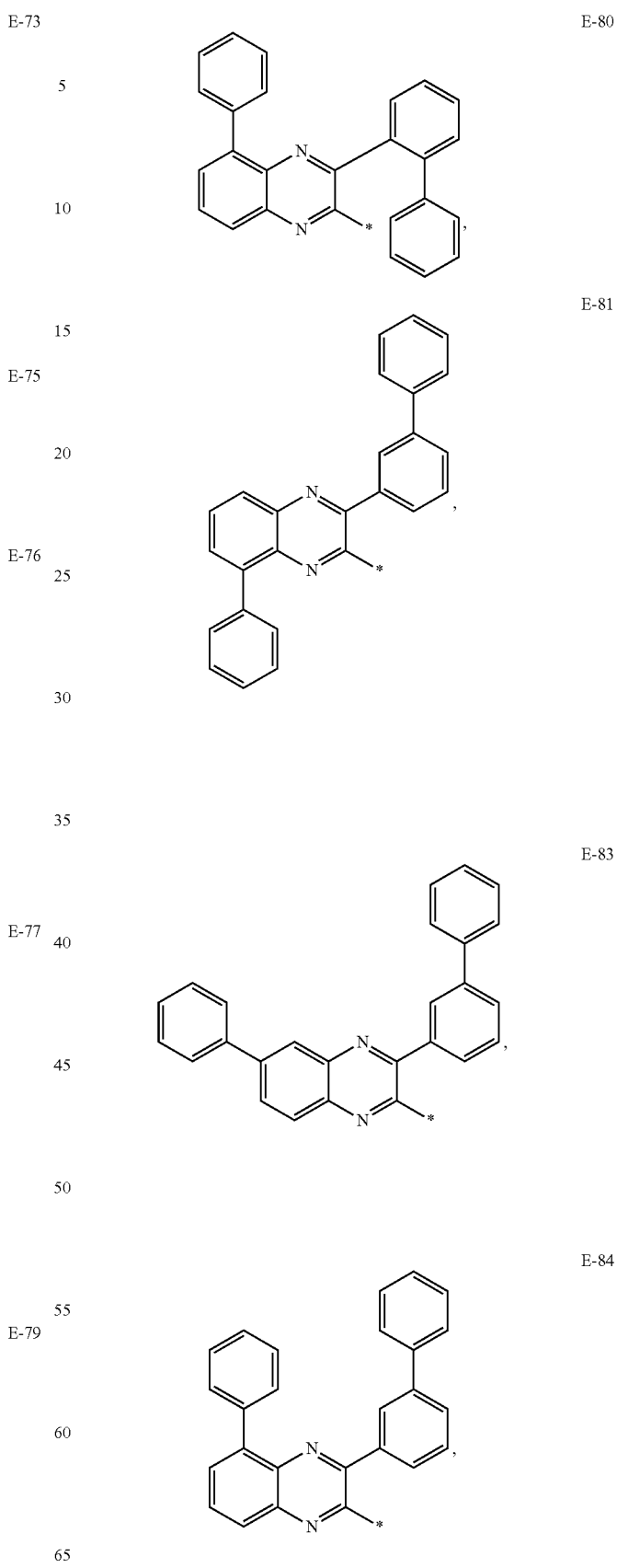

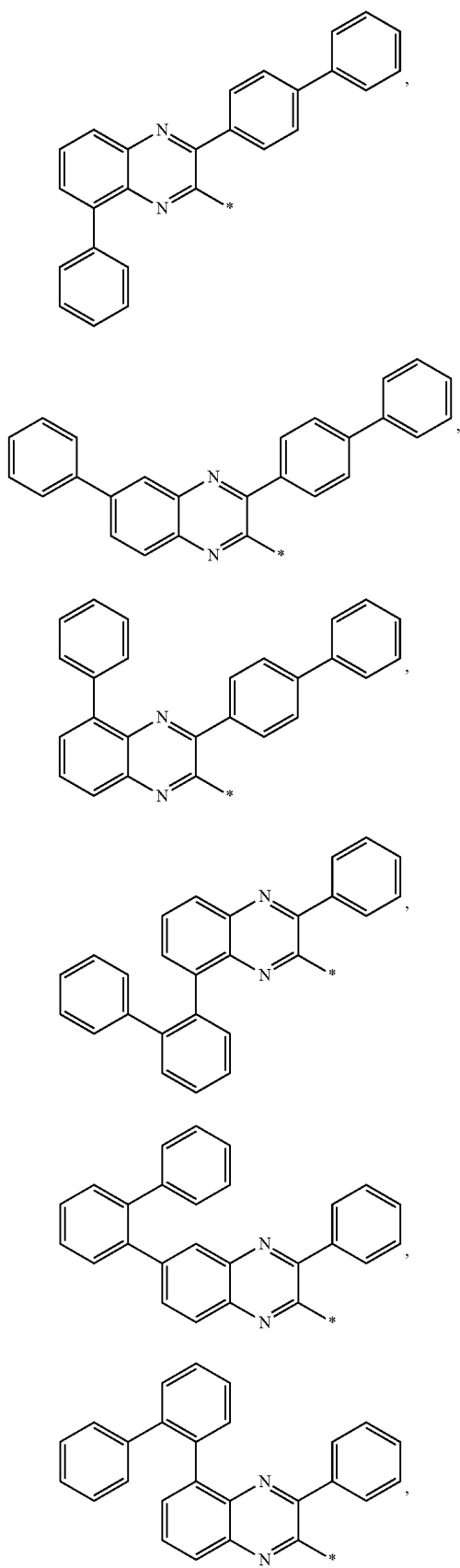
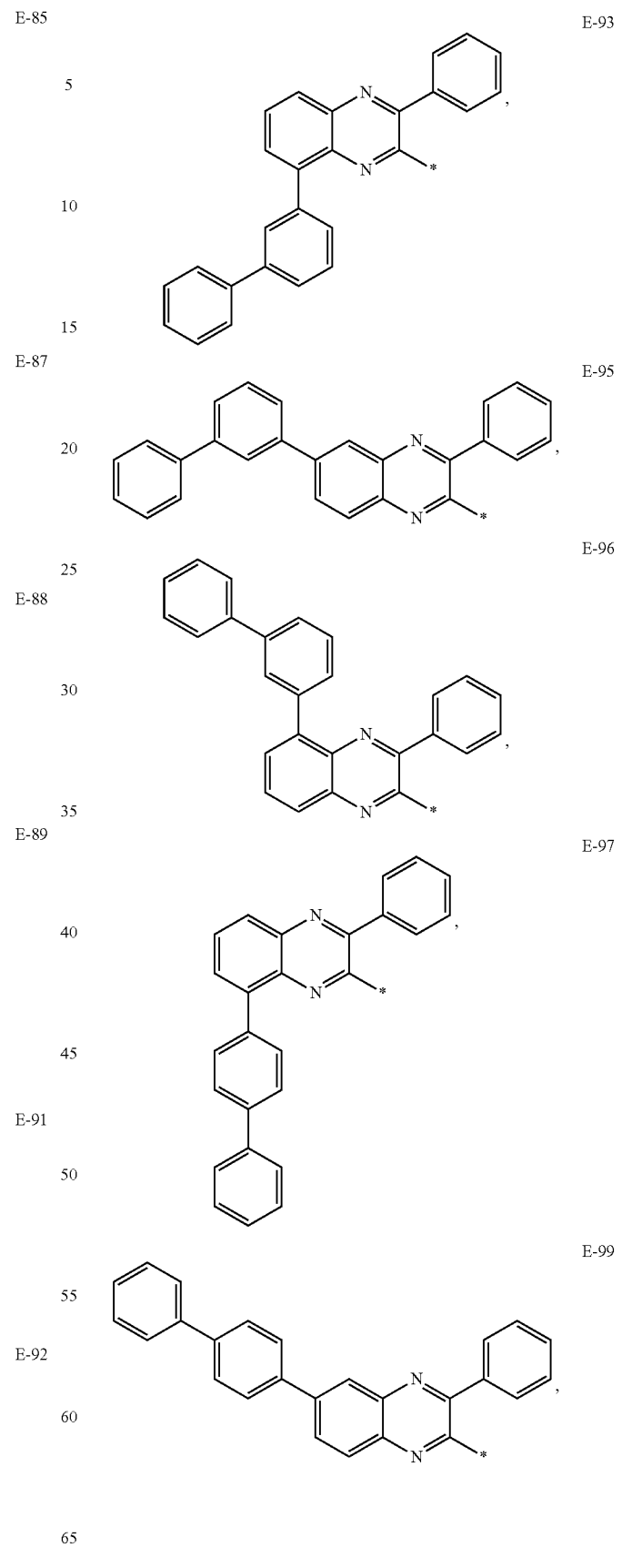

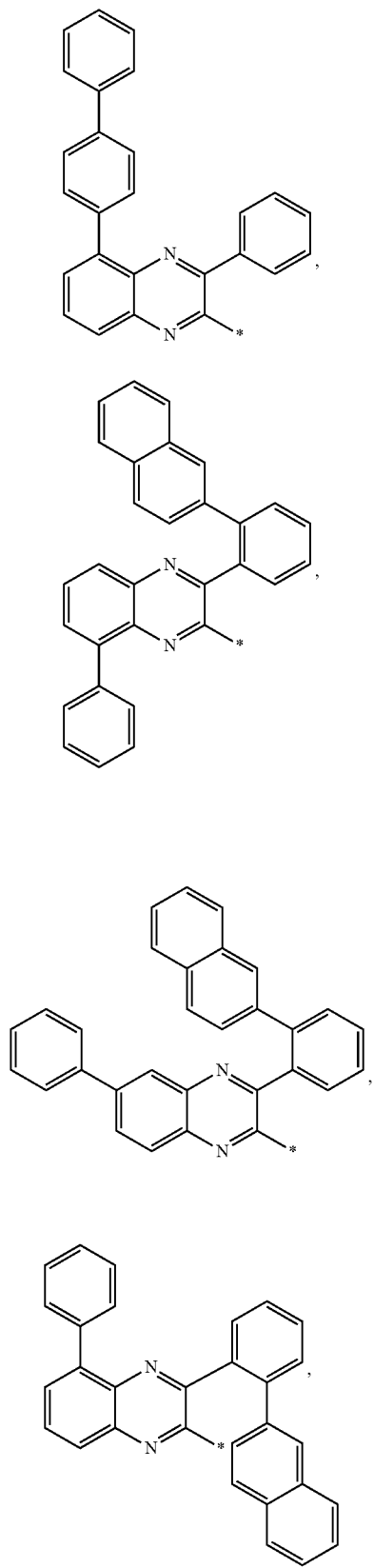
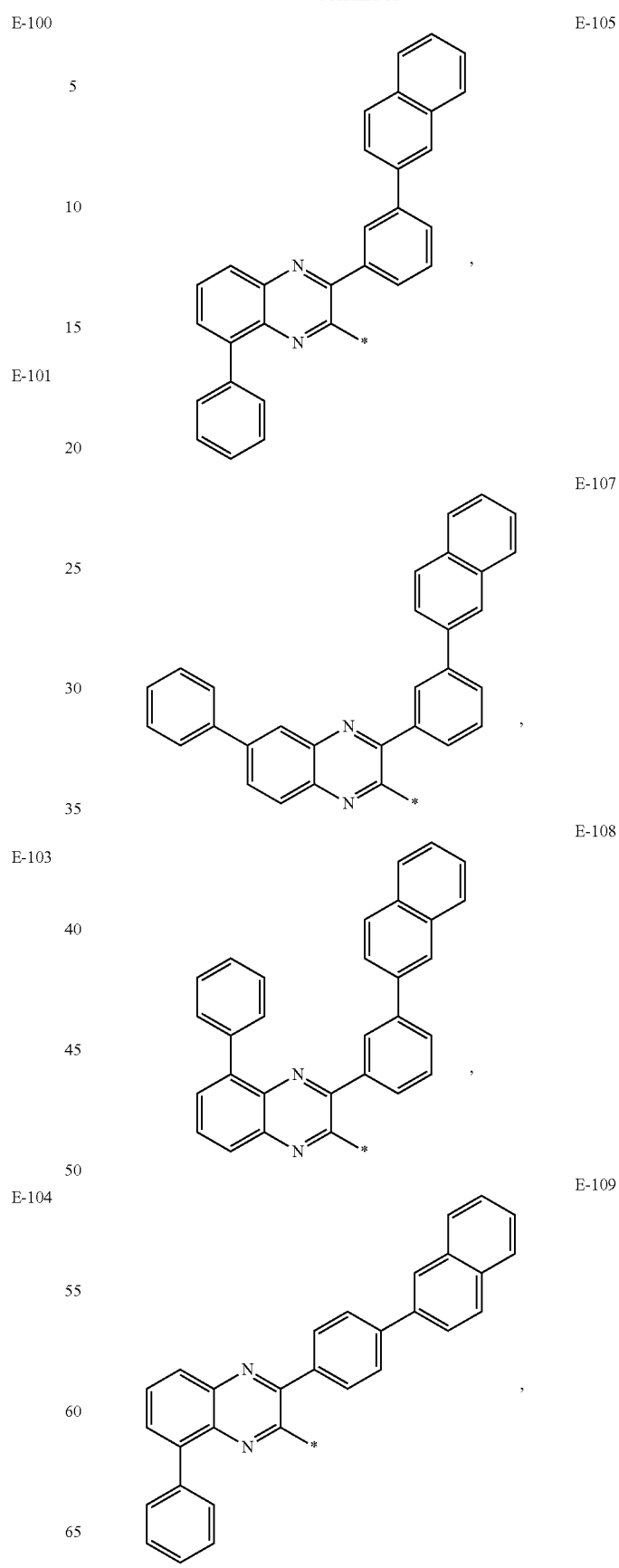

-continued

E-111

E-112

E-113

E-115

E-116

E-117

E-119

E-120

E-121

E-123
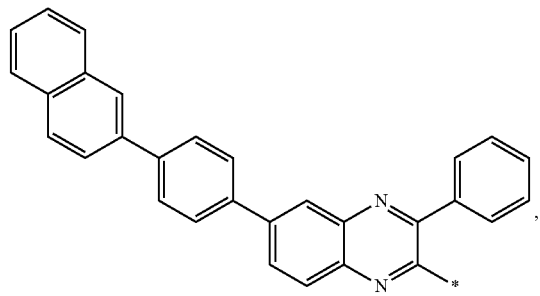
E-124
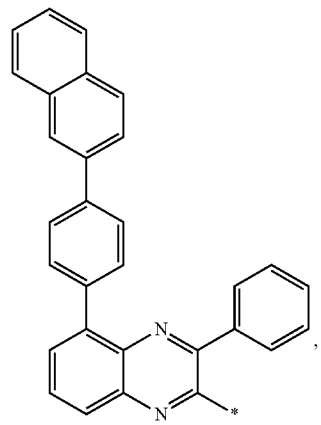
E-125
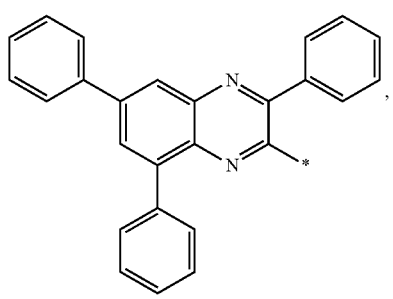
E-126
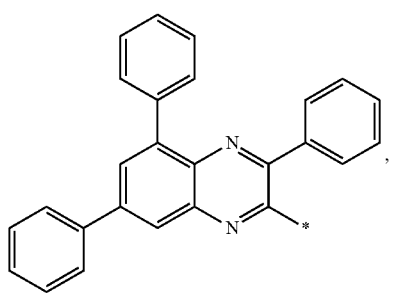
E-127
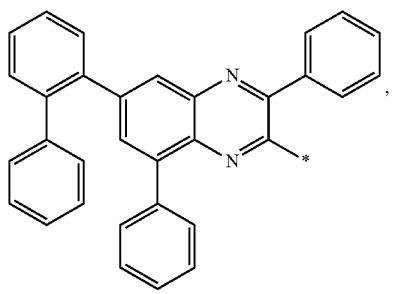
E-128
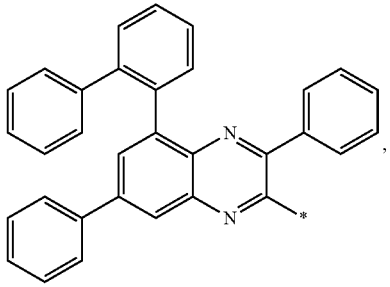
E-129
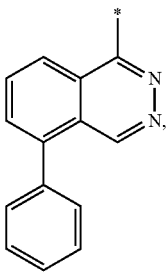
E-130
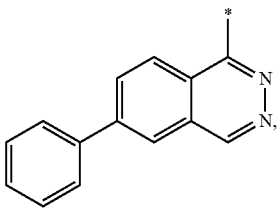
E-131
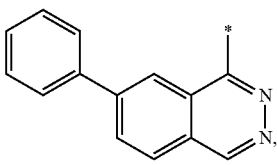
E-132
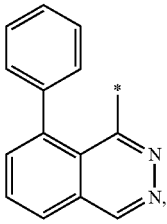
E-133
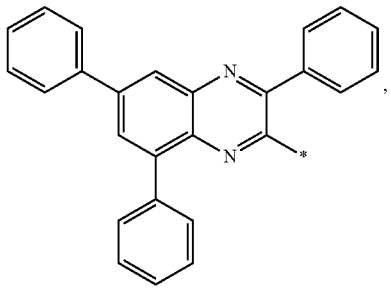

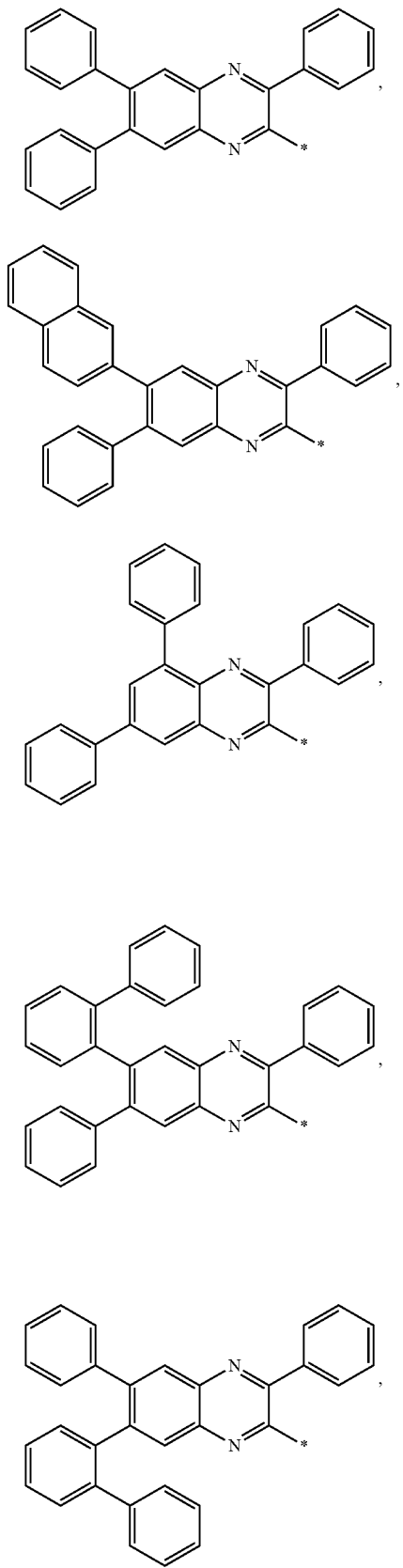
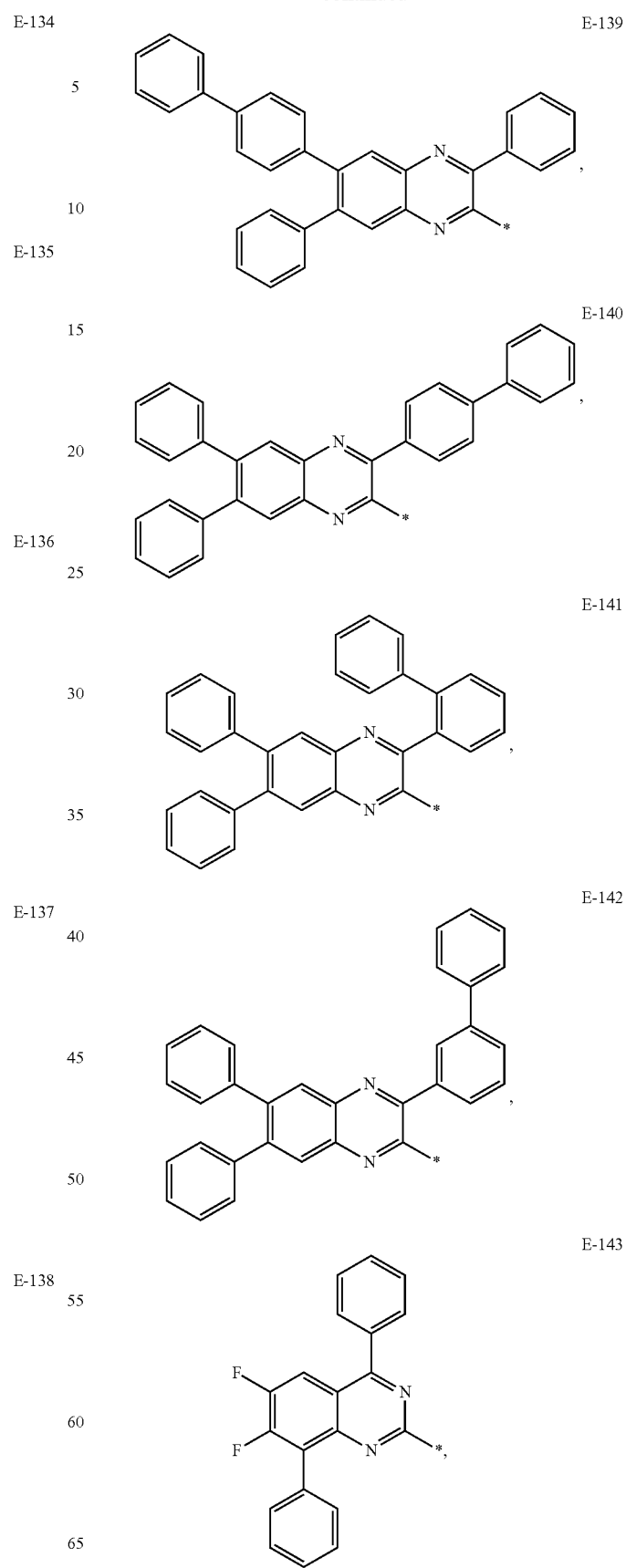

E-144
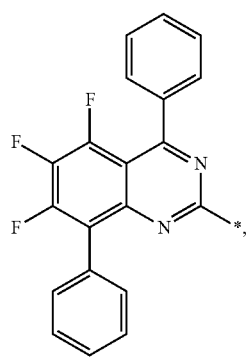
E-146
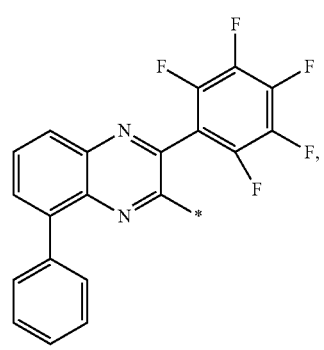
E-171
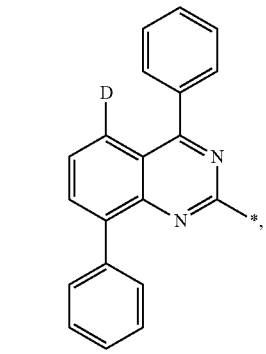
E-172
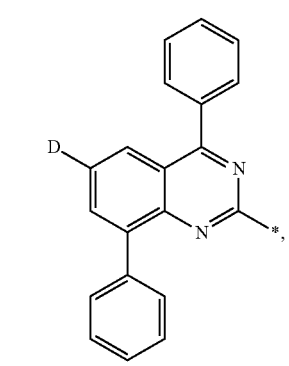
E-173
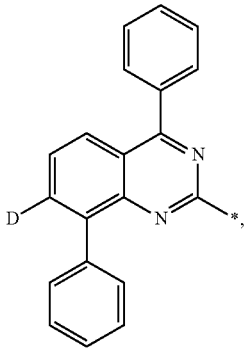
E-174
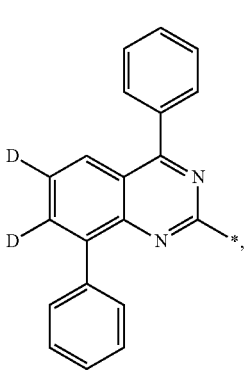
E-175
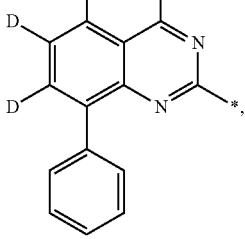
E-176
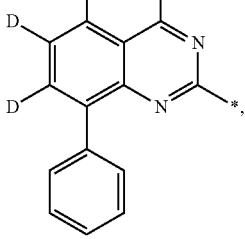

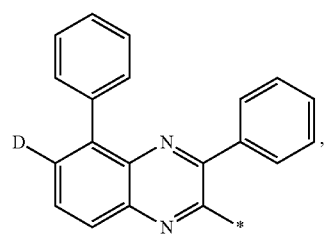
E-189
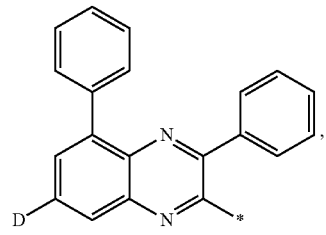
E-190
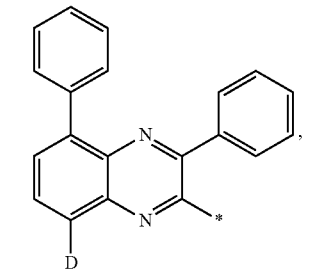
E-191
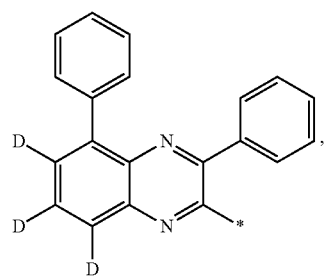
E-192
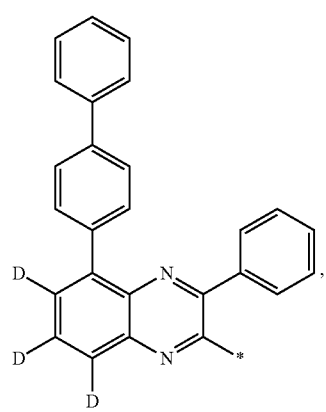
E-193
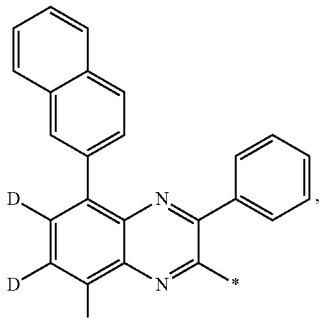
E-194
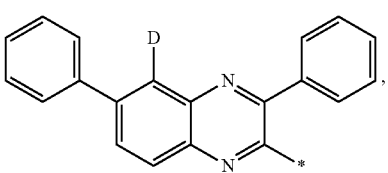
E-195
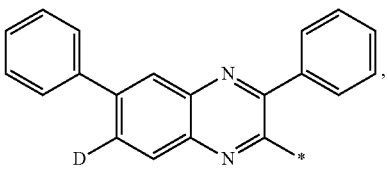
E-196
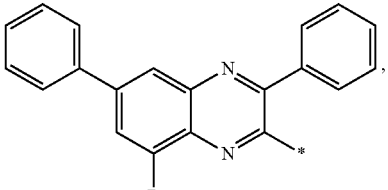
E-197
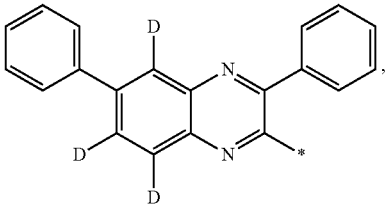
E-198
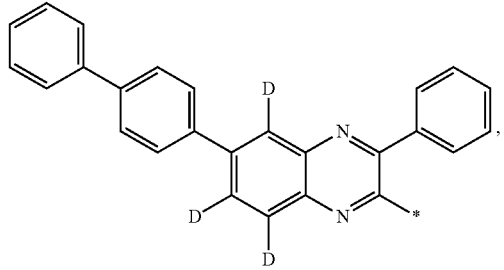
E-199
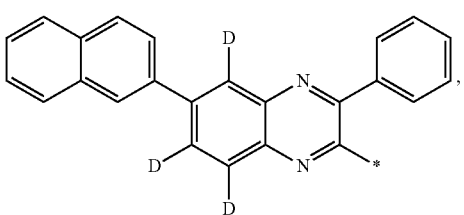
E-200

E-207 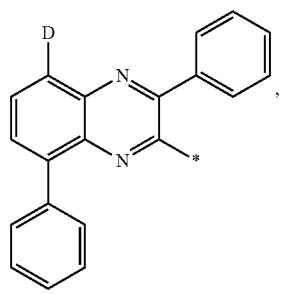
E-208 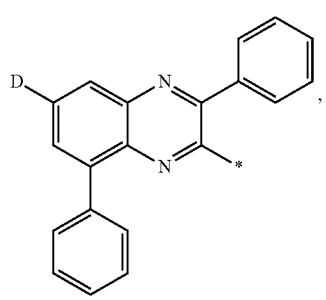
E-209 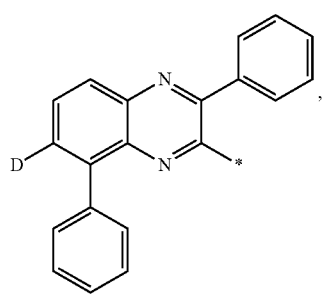
E-210 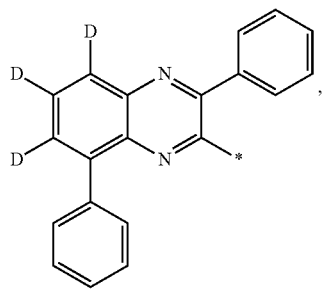
E-211 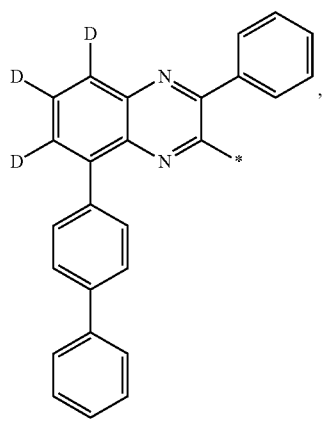
E-212 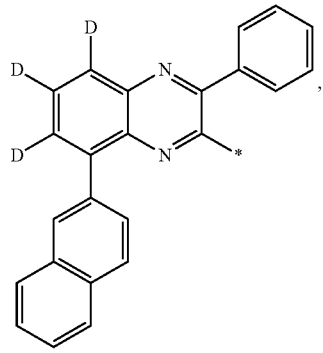
E-213 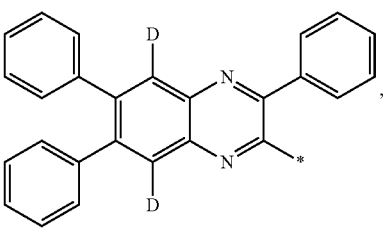
E-214 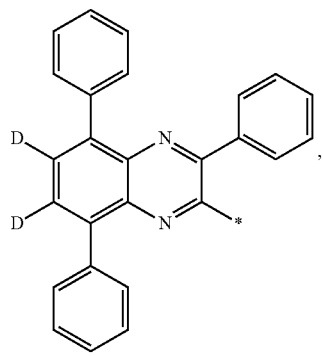
E-215 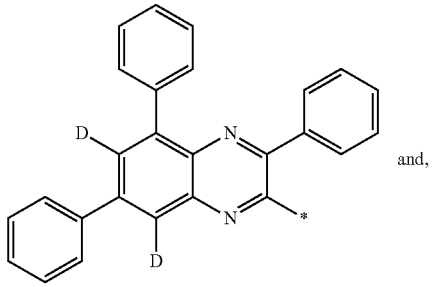
and,
E-216 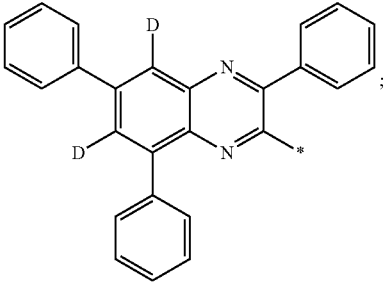
;
wherein optionally, hydrogens in the above structures can be partially or fully substituted with deuterium.
9. The compound according to claim 8, wherein the compound is selected from the group consisting of the following Compounds, wherein the following Compound each has a structure of H-L-E, wherein H, L, and E are selected from structures in the following table, respectively, wherein L-0 is a single bond:

| Compound | H | L | E |
|---|---|---|---|
| 1 | H-1 | L-0 | E-1 |
| 5 | H-1 | L-0 | E-5 |
| 9 | H-1 | L-0 | E-9 |
| 13 | H-1 | L-0 | E-13 |
| 17 | H-1 | L-0 | E-17 |
| 21 | H-1 | L-0 | E-21 |
| 25 | H-1 | L-0 | E-25 |
| 29 | H-1 | L-0 | E-29 |
| 33 | H-1 | L-0 | E-33 |
| 37 | H-1 | L-0 | E-37 |
| 41 | H-1 | L-0 | E-41 |
| 45 | H-1 | L-0 | E-45 |
| 47 | H-1 | L-0 | E-47 |
| 49 | H-1 | L-0 | E-49 |
| 51 | H-1 | L-0 | E-51 |
| 53 | H-1 | L-0 | E-53 |
| 55 | H-1 | L-0 | E-55 |
| 56 | H-1 | L-0 | E-56 |
| 57 | H-1 | L-0 | E-57 |
| 59 | H-1 | L-0 | E-59 |
| 60 | H-1 | L-0 | E-60 |
| 61 | H-1 | L-0 | E-61 |
| 63 | H-1 | L-0 | E-63 |
| 64 | H-1 | L-0 | E-64 |
| 65 | H-1 | L-0 | E-65 |
| 67 | H-1 | L-0 | E-67 |
| 68 | H-1 | L-0 | E-68 |
| 69 | H-1 | L-0 | E-69 |
| 71 | H-1 | L-0 | E-71 |
| 72 | H-1 | L-0 | E-72 |
| 73 | H-1 | L-0 | E-73 |
| 75 | H-1 | L-0 | E-75 |
| 76 | H-1 | L-0 | E-76 |
| 77 | H-1 | L-0 | E-77 |
| 79 | H-1 | L-0 | E-79 |
| 80 | H-1 | L-0 | E-80 |
| 81 | H-1 | L-0 | E-81 |
| 83 | H-1 | L-0 | E-83 |
| 84 | H-1 | L-0 | E-84 |
| 85 | H-1 | L-0 | E-85 |
| 87 | H-1 | L-0 | E-87 |
| 88 | H-1 | L-0 | E-88 |
| 89 | H-1 | L-0 | E-89 |
| 91 | H-1 | L-0 | E-91 |
| 92 | H-1 | L-0 | E-92 |
| 93 | H-1 | L-0 | E-93 |
| 95 | H-1 | L-0 | E-95 |
| 96 | H-1 | L-0 | E-96 |
| 97 | H-1 | L-0 | E-97 |
| 99 | H-1 | L-0 | E-99 |
| 100 | H-1 | L-0 | E-100 |
| 101 | H-1 | L-0 | E-101 |
| 103 | H-1 | L-0 | E-103 |
| 104 | H-1 | L-0 | E-104 |
| 105 | H-1 | L-0 | E-105 |
| 107 | H-1 | L-0 | E-107 |
| 108 | H-1 | L-0 | E-108 |
| 109 | H-1 | L-0 | E-109 |
| 111 | H-1 | L-0 | E-111 |
| 112 | H-1 | L-0 | E-112 |
| 113 | H-1 | L-0 | E-113 |
| 115 | H-1 | L-0 | E-115 |
| 116 | H-1 | L-0 | E-116 |
| 117 | H-1 | L-0 | E-117 |
| 119 | H-1 | L-0 | E-119 |
| 120 | H-1 | L-0 | E-120 |
| 121 | H-1 | L-0 | E-121 |
| 123 | H-1 | L-0 | E-123 |
| 124 | H-1 | L-0 | E-124 |
| 125 | H-1 | L-0 | E-125 |
| 126 | H-1 | L-0 | E-126 |
| 127 | H-1 | L-0 | E-127 |
| 128 | H-1 | L-0 | E-128 |
| 129 | H-1 | L-0 | E-129 |
| 130 | H-1 | L-0 | E-130 |
| 131 | H-1 | L-0 | E-131 |
| 132 | H-1 | L-0 | E-132 |
| 133 | H-1 | L-0 | E-133 |
| 134 | H-1 | L-0 | E-134 |
| 135 | H-1 | L-0 | E-135 |
| 136 | H-1 | L-0 | E-136 |
| 137 | H-1 | L-0 | E-137 |
| 138 | H-1 | L-0 | E-138 |
| 139 | H-1 | L-0 | E-139 |
| 140 | H-1 | L-0 | E-140 |
| 141 | H-1 | L-0 | E-141 |
| 142 | H-1 | L-0 | E-142 |
| 143 | H-1 | L-0 | E-143 |
| 144 | H-1 | L-0 | E-144 |
| 146 | H-1 | L-0 | E-146 |
| 171 | H-1 | L-0 | E-171 |
| 172 | H-1 | L-0 | E-172 |
| 173 | H-1 | L-0 | E-173 |
| 174 | H-1 | L-0 | E-174 |
| 175 | H-1 | L-0 | E-175 |
| 176 | H-1 | L-0 | E-176 |
| 189 | H-1 | L-0 | E-189 |
| 190 | H-1 | L-0 | E-190 |
| 191 | H-1 | L-0 | E-191 |
| 192 | H-1 | L-0 | E-192 |
| 193 | H-1 | L-0 | E-193 |
| 194 | H-1 | L-0 | E-194 |
| 195 | H-1 | L-0 | E-195 |
| 196 | H-1 | L-0 | E-196 |
| 197 | H-1 | L-0 | E-197 |
| 198 | H-1 | L-0 | E-198 |
| 199 | H-1 | L-0 | E-199 |
| 200 | H-1 | L-0 | E-200 |
| 207 | H-1 | L-0 | E-207 |
| 208 | H-1 | L-0 | E-208 |
| 209 | H-1 | L-0 | E-209 |
| 210 | H-1 | L-0 | E-210 |
| 211 | H-1 | L-0 | E-211 |
| 212 | H-1 | L-0 | E-212 |
| 213 | H-1 | L-0 | E-213 |
| 214 | H-1 | L-0 | E-214 |
| 215 | H-1 | L-0 | E-215 |
| 216 | H-1 | L-0 | E-216 |
| 749 | H-102 | L-0 | E-1 |
| 750 | H-103 | L-0 | E-1 |
| 751 | H-104 | L-0 | E-1 |
| 752 | H-105 | L-0 | E-1 |
| 753 | H-106 | L-0 | E-1 |
| 754 | H-107 | L-0 | E-1 |
| 755 | H-108 | L-0 | E-1 |
| 756 | H-109 | L-0 | E-1 |
| 757 | H-110 | L-0 | E-1 |
| 758 | H-111 | L-0 | E-1 |
| 759 | H-112 | L-0 | E-1 |
| 760 | H-113 | L-0 | E-1 |
| 761 | H-114 | L-0 | E-1 |
| 762 | H-115 | L-0 | E-1 |
| 763 | H-116 | L-0 | E-1 |
| 764 | H-117 | L-0 | E-1 |
| 765 | H-118 | L-0 | E-1 |
| 983 | H-102 | L-0 | E-134 |
| 984 | H-103 | L-0 | E-134 |
| 985 | H-104 | L-0 | E-134 |
| 986 | H-105 | L-0 | E-134 |
| 987 | H-106 | L-0 | E-134 |
| 988 | H-107 | L-0 | E-134 |
| 989 | H-108 | L-0 | E-134 |
| 990 | H-109 | L-0 | E-134 |
| 991 | H-110 | L-0 | E-134 |
| 992 | H-111 | L-0 | E-134 |
| 993 | H-112 | L-0 | E-134 |
| 994 | H-113 | L-0 | E-134 |
| 995 | H-114 | L-0 | E-134 |
| 996 | H-115 | L-0 | E-134 |
| 997 | H-116 | L-0 | E-134 |

-continued

| Compound | H | L | E |
|---|---|---|---|
| 998 | H-117 | L-0 | E-134 |
| 999 | H-118 | L-0 | E-134 | wherein optionally, hydrogens in the above structures can be partially or fully substituted with deuterium.

10. An electroluminescent device, comprising:
an anode,
a cathode, and
an organic layer disposed between the anode and the cathode, wherein the organic layer comprises the compound according to claim 1.

11. The electroluminescent device according to claim 10, wherein the organic layer is an emissive layer, and the compound is a host material.

12. The electroluminescent device according to claim 11, wherein the emissive layer further comprises at least one phosphorescent material.

13. The electroluminescent device according to claim 12, wherein the phosphorescent material is a metal complex comprising at least one ligand, wherein the ligand comprises any one of the following structures:

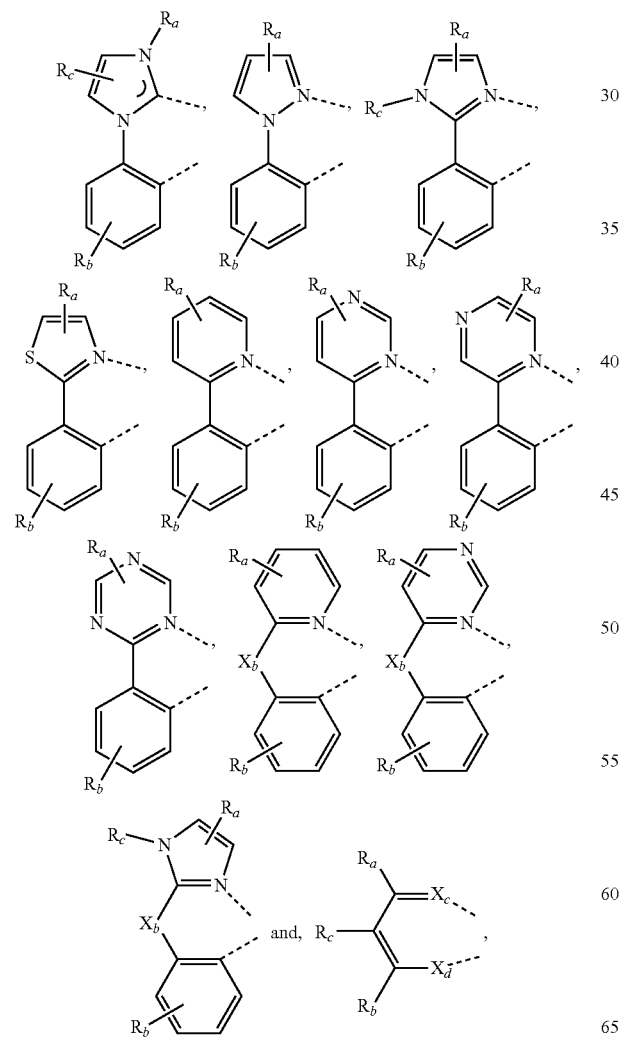

wherein
$R_a$, $R_b$, and $R_c$, at each occurrence identically or differently, represent mono-substitution, multiple substitutions or non-substitution;
$X_b$ is, at each occurrence identically or differently, selected from the group consisting of: O, S, Se, $NR_{N1}$, and $CR_{C1}R_{C2}$;
$X_c$ and $X_d$ are, at each occurrence identically or differently, selected from the group consisting of: O, S, Se, and $NR_{N2}$;
$R_a$, $R_b$, $R_c$, $R_{N1}$, $R_{N2}$, $R_{C1}$, and $R_{C2}$ are, at each occurrence identically or differently, selected from the group consisting of, hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof;
in the structure of the ligand, adjacent substituents can be optionally joined to form a ring.

14. The electroluminescent device according to claim 12, wherein the phosphorescent material is a metal complex comprising at least one ligand, wherein the ligand is represented by the following structure:

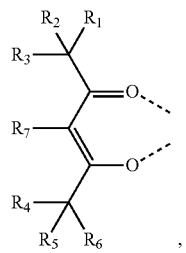

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof.

15. The electroluminescent device according to claim 13, wherein the phosphorescent material is an Ir complex, a Pt complex or an Os complex.

16. A compound formulation, comprising the compound according to claim 1.

17. The compound according to claim 4, wherein at least one of R and $R_x$ is selected from deuterium, phenyl, biphenyl or pyridyl.

18. The compound according to claim 1, wherein in Formula 2-c, $Y_2$ is selected from $CR_z$, and $Y_1$, $Y_3$ and $Y_4$ are each independently selected from $CR_y$; or $Y_1$ and $Y_4$ are selected from $CR_z$, and $Y_2$ and $Y_3$ are each independently selected from $CR_y$.

19. The compound according to claim 1, wherein the $R_y$ is, at each occurrence identically or differently, selected from the group consisting of: hydrogen, deuterium, halogen, substituted or unsubstituted aryl having 6 to 30 carbon atoms, and combinations thereof;

the $R_z$ is, at each occurrence identically or differently, selected from substituted or unsubstituted aryl having 6 to 18 carbon atoms.

20. The compound according to claim 1, wherein the $R_y$ is, at each occurrence identically or differently, selected from the group consisting of: hydrogen, deuterium, fluorine, phenyl, biphenyl, naphthyl, and combinations thereof;

the $R_z$ is, at each occurrence identically or differently, selected from phenyl, biphenyl, naphthyl, or combinations thereof.

21. The compound according to claim 1, wherein the $R_y$ is selected from deuterium, phenyl, biphenyl, naphthyl, 4-cyanophenyl, dibenzofuryl, dibenzothienyl, triphenylene, carbazolyl, 9-phenylcarbazolyl, 9,9-dimethylfluorenyl, pyridyl or phenylpyridyl.

22. The electroluminescent device according to claim 15, wherein the phosphorescent material is an Ir complex and has a structure of $Ir(L_a)(L_b)(L_c)$;

wherein $L_a$, $L_b$, and $L_c$ are, at each occurrence identically or differently, selected from any one of the above ligands.

23. The electroluminescent device according to claim 15, wherein the Ir complex is selected from the group consisting of the following structures:

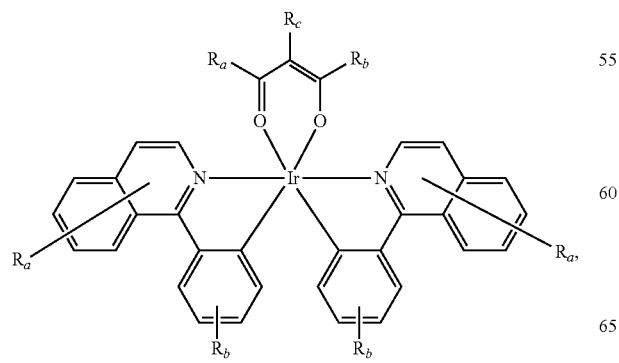

-continued

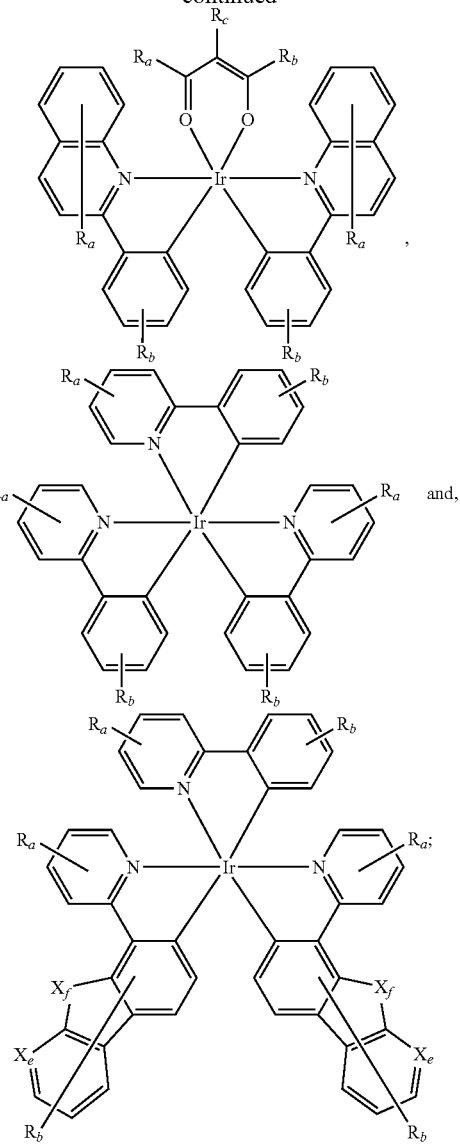

wherein $X_f$ is, at each occurrence identically or differently, selected from the group consisting of: O, S, Se, $NR_{N3}$, and $CR_{C3}R_{C4}$;

wherein $X_e$ is, at each occurrence identically or differently, selected from $CR_d$ or N;

$R_a$, $R_b$, and $R_c$, at each occurrence identically or differently, represent mono-substitution, multiple substitutions or non-substitution;

$R_a$, $R_b$, $R_c$, $R_d$, $R_{N3}$, $R_{C3}$, and $R_{C4}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof.

24. The compound according to claim 1, wherein E has a structure represented by Formula 2-a.

* * * * *